US007998688B2

(12) United States Patent
Shaaban et al.

(10) Patent No.: US 7,998,688 B2
(45) Date of Patent: Aug. 16, 2011

(54) INHIBITION OF EMT INDUCTION IN TUMOR CELLS BY ANTI-CANCER AGENTS

(75) Inventors: Salam A. Shaaban, Westborough, MA (US); Jonathan A. Pachter, Setauket, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 0 days.

(21) Appl. No.: 12/381,101

(22) Filed: Mar. 6, 2009

(65) Prior Publication Data

US 2009/0286850 A1 Nov. 19, 2009

Related U.S. Application Data

(60) Provisional application No. 61/068,566, filed on Mar. 7, 2008.

(51) Int. Cl.
*G01N 33/53* (2006.01)
*C12Q 1/68* (2006.01)
(52) U.S. Cl. ............................................ 435/7.1; 435/6
(58) Field of Classification Search .................. None
See application file for complete search history.

(56) References Cited

U.S. PATENT DOCUMENTS

| | | | |
|---|---|---|---|
| 5,518,911 A | 5/1996 | Abo | |
| 5,863,532 A | 1/1999 | Traugh | |
| 6,383,734 B1 | 5/2002 | Marshall | |
| 6,599,726 B2 | 7/2003 | Traugh | |
| 7,118,854 B2 * | 10/2006 | Liao et al. | 435/4 |
| 7,514,207 B2 * | 4/2009 | Jacks et al. | 435/4 |
| 2002/0052308 A1 | 5/2002 | Rosen | |
| 2004/0006083 A1 | 1/2004 | Hirst | |
| 2004/0092546 A1 | 5/2004 | Wei | |
| 2004/0102623 A1 | 5/2004 | Monica | |
| 2004/0186160 A1 | 9/2004 | Tang | |
| 2005/0009876 A1 | 1/2005 | Bhagwat | |
| 2005/0043347 A1 | 2/2005 | Betschmann | |
| 2005/0080002 A1 | 4/2005 | Jacks | |
| 2005/0085531 A1 | 4/2005 | Hodge | |
| 2006/0004043 A1 | 1/2006 | Bhagwat | |
| 2006/0009460 A1 | 1/2006 | Dickson | |
| 2006/0052416 A1 | 3/2006 | Dickson | |
| 2006/0211060 A1 | 9/2006 | Haley | |
| 2007/0212738 A1 | 9/2007 | Haley | |
| 2007/0213352 A1 | 9/2007 | Zhang | |
| 2009/0092596 A1 | 4/2009 | Haley | |

FOREIGN PATENT DOCUMENTS

| | | |
|---|---|---|
| WO | 0019205 A1 | 4/2000 |
| WO | 0060062 A2 | 10/2000 |
| WO | 02081638 A2 | 10/2002 |
| WO | 2004024883 A2 | 3/2004 |
| WO | 2006029337 A2 | 3/2006 |
| WO | 2006106326 A1 | 10/2006 |
| WO | 2006106326 C1 | 10/2006 |

OTHER PUBLICATIONS

Acconcia, F. et al. (2007) Proc Natl Acad Sci USA 104(16): 6782-6787.
Aigner, K. et al. (2007) Oncogene 26(49): 6929-6988.
Arias-Romero, L.E. and Chernoff, J. (2008) Biol Cell 100:97-108.
Bagrodia, S. and Cerione, R. A. (1999) Cell Biology 9:350-355.
Barrallo-Gimeno, A. and Nieto, M.A. (2005) Development 132: 3151-3161. Published by The Company of Biologists.
Bates, R. C. et al. (2003) Current Biology 13:1721-1727.
Besser, A. et al. (2005) The Journal of Biological Chemistry 280 (44): 36609-36615.
Buck, E. et al. (2007) Mol Cancer Ther 6(2):532-541.
Cano, A. et al. (2000) Nature Cell Biology 2:76-83.
Cho, H.J. et al. (2007) Biochem Biopyhs Res Commun 353(2): 337-343.
Dancey, J. and Sausville, E. A. (2003) Nature 2:296-313.
Deacon, S.W. et al. (2008) Chemistry & Biology 15: 322-331.
Debono, J.S. and Rowinsky, E.K. (2002) Trends in Molecular Medicine 8 (4): S19-S26.
Frederick, B.A. et al. (2007) Mol Cancer Ther 6(6): 1683-1691.
Goeckeler, Z. (2000) J Biol Chem 277(12): 10394-10399.
Grille, S. J. et al. (2003) Cancer Research 63: 2172-2178.
Grotegut, S. et al. (2006) EMBO J 25(15): 3534-3545.
Guaita, S. et al. (2002) J. Biol. Chem. 277(42): 39209-39216.
Guo, D. et al. (2007) Cell 128: 341-355.
Huber, M.A. et al. (2005) 17:548-558.
Jaffar, Z. and Chernoff,J. (2002) The International Journal of Biochemistry & Cell Biology 34:713-717.
Jung, J. and Traugh, J. A. (2005) The Journal of Biological Chemistry 280 (48): 40025-40031.
Kang, Y. and Massague, J. (2004) Cell 118:277-279.
Kiemer, A.K. et al. (2001) Oncogene 20: 6679-6688.
Kissil, J. (2002) J Biol Chem 277(12): 10394-10399.
Kumar, R. and Vadlamudi (2002) Journal of Cellular Physiology 193: 133-144.
Kumar, R. et al. (2006) Nature Reviews/Cancer 6:459-471.
Lee, J.M. et al. (2006) The Journal of Cell Biology 172(7): 973-981.
Li, F.L. (2002) EMBO Reports 3(8): 767-773.
Li, Q.F. et al. (2006) J Biol Chem 281(45): 34716-34724.
Li, X. et al. (2006) Oncogene 25(4): 609-621.
Lu, W. et al. (1997) Current Biology 7(2):85-94.
Lu, Z. et al. (2003) Cancer Cell 4:499-515.

(Continued)

*Primary Examiner* — Suzanne M. Noakes
(74) *Attorney, Agent, or Firm* — Alexander A. Stewart; OSI Pharmaceuticals, LLC

(57) ABSTRACT

The present invention provides methods of identifying an agents that inhibit tumor cells from undergoing an epithelial to mesenchymal transition, impair tumor cell mobility, and thus inhibit tumorigenicity. The present invention also provides compositions comprising said agents, and methods for their preparation and use. The present invention also provides methods for inhibiting tumor cells in a patient from undergoing an epithelial to mesenchymal transition by administration of inhibitors of PAK2 kinase, that optionally also inhibit PAK1 kinase. Such methods may be employed in combination with other anti-cancer agents such as EGFR or IGF-1R kinase inhibitors.

13 Claims, 10 Drawing Sheets

OTHER PUBLICATIONS

Lu, W. and Mayer, B.J. (1999) Oncogene 18: 797-806.
Meng, Q. et al. (2007) Proc Natl Acad Sci USA 104(14): 5866-5871.
Moody, S.E. et al. (2005) Cancer Cell 8: 197-209.
Park, E.R. et al. (2007) Cellular Signalling 19: 1488-1496.
Pienado, H. (2007) Nature Reviews/Cancer 7: 415-428.
Porchia, L.M. et al. (2007) Molecular Pharmacology Fast Forward, MOL #37556, pp. 1-32.
Rennefahrt, U.E.E. et al. (2007) The Journal of Biological Chemistry 282(21): 15667-15678.
Rong, R. et al. (2004) Oncogene 23: 8447-8454.
Savanger, P. (2001) BioEssays 23: 912-923.
Somasiri, A. et al. (2001) J Cell Sci 114(Pt 6): 1125-1136.
Sundberg-Smith, L. J. et al. (2005) The Journal of Biological Chemistry 280(3): 2055-2064.
Suzuki, K. et al. (2007) Cancer Res 67(8):3673-3682.
Thiery, J.P. (2002) Nature 2: 442-454.
Thomson, S. et al. (2005) Cancer Res 65(20): 9455-9462.
Venkov, C.D. et al. (2007) J Clin Invest 117(2): 482-491.
Wilkes, M.C. (2003) Molecular and Cellular Biology 23(23): 8878-8889.
Yang, Z. et al. (2005) Cancer Res 65(8): 3179-3184.
Yauch, R. L. (2005) Clin Cancer Res 11(24): 8686-8698.
Yook, J.I. et al. (2006) Nat Cell Biol 8(12): 1398-1406.
Zhao, Z. and Manser, E. (2005) Biochem J 386:201-214.
Zhou, B.P. et al. (2004) Nat Cell Biol 6(10): 931-940.

* cited by examiner

Figure 9

MSDNGELEDKPPAPPVRMSSTIFSTGGKDPLSANHSLKPLPSVPEEKKP
RHKIISIFSGTEKGSKKKEKERPEISPPSDFEHTIHVGFDAVTGEFTGM
PEQWARLLQTSNITKLEQKKNPQAVLDVLKFYDSNTVKQKYLSFTPPEK
DGFPSGTPALNAKGTEAPAVVTEEEDDDEETAPPVIAPRPDHTKSIYTR
SVIDPVPAPVGDSHVDGAAKSLDKQKKKTKMTDEEIMEKLRTIVSIGDP
KKKYTRYEKIGQGASGTVFTATDVALGQEVAIKQINLQKQPKKELIINE
ILVMKELKNPNIVNFLDSYLVGDELFVVMEYLAGGSLTDVVTETCMDEA
QIAAVCRECLQALEFLHANQVIHRDIKSDNVLLGMEGSVKLTDFGFCAQ
ITPEQSKRSTMVGTPYWMAPEVVTRKAYGPKVDIWSLGIMAIEMVEGEP
PYLNENPLRALYLIATNGTPELQNPEKLSPIFRDFLNRCLEMDVEKRGS
AKELLQHPFLKLAKPLSSLTPLIMAAKEAMKSNR

Figure 10

MSNNGLDIQDKPPAPPMRNTSTMIGAGSKDAGTLNHGSKPLPPNPEEKK
KKDRFYRSILPGDKTNKKKEKERPEISLPSDFEHTIHVGFDAVTGEFTG
MPEQWARLLQTSNITKSEQKKNPQAVLDVLEFYNSKKTSNSQKYMSFTD
KSAEDYNSSNALNVKAVSETPAVPPVSEDEDDDDDATPPPVIAPRPEH
TKSVYTRSVIEPLPVTPTRDVATSPISPTENNTTPPDALTRNTEKQKKK
PKMSDEEILEKLRSIVSVGDPKKKYTRFEKIGQGASGTVYTAMDVATGQ
EVAIKQMNLQQQPKKELIINEILVMRENKNPNIVNYLDSYLVGDELWVV
MEYLAGGSLTDVVTETCMDEGQIAAVCRECLQALEFLHSNQVIHRDIKS
DNILLGMDGSVKLTDFGFCAQITPEQSKRSTMVGTPYWMAPEVVTRKAY
GPKVDIWSLGIMAIEMIEGEPPYLNENPLRALYLIATNGTPELQNPEKL
SAIFRDFLNRCLEMDVEKRGSAKELLQHQFLKIAKPLSSLTPLIAAAKE
ATKNNH

SEQUENCE LISTING

```
<160> NUMBER OF SEQ ID NOS: 4

<210> SEQ ID NO 1
<211> LENGTH: 524
<212> TYPE: PRT
<213> ORGANISM: Homo sapiens

<400> SEQUENCE: 1

Met Ser Asp Asn Gly Glu Leu Glu Asp Lys Pro Pro Ala Pro Pro Val
1               5                   10                  15

Arg Met Ser Ser Thr Ile Phe Ser Thr Gly Gly Lys Asp Pro Leu Ser
            20                  25                  30
```

```
Ala Asn His Ser Leu Lys Pro Leu Pro Ser Val Pro Glu Glu Lys Lys
            35                  40                  45

Pro Arg His Lys Ile Ile Ser Ile Phe Ser Gly Thr Glu Lys Gly Ser
 50                  55                  60

Lys Lys Lys Glu Lys Glu Arg Pro Glu Ile Ser Pro Pro Ser Asp Phe
 65                  70                  75                  80

Glu His Thr Ile His Val Gly Phe Asp Ala Val Thr Gly Glu Phe Thr
                    85                  90                  95

Gly Met Pro Glu Gln Trp Ala Arg Leu Leu Gln Thr Ser Asn Ile Thr
                100                 105                 110

Lys Leu Glu Gln Lys Lys Asn Pro Gln Ala Val Leu Asp Val Leu Lys
            115                 120                 125

Phe Tyr Asp Ser Asn Thr Val Lys Gln Lys Tyr Leu Ser Phe Thr Pro
            130                 135                 140

Pro Glu Lys Asp Gly Phe Pro Ser Gly Thr Pro Ala Leu Asn Ala Lys
145                 150                 155                 160

Gly Thr Glu Ala Pro Ala Val Val Thr Glu Glu Asp Asp Glu
                    165                 170                 175

Glu Thr Ala Pro Pro Val Ile Ala Pro Arg Pro Asp His Thr Lys Ser
                180                 185                 190

Ile Tyr Thr Arg Ser Val Ile Asp Pro Val Pro Ala Pro Val Gly Asp
            195                 200                 205

Ser His Val Asp Gly Ala Ala Lys Ser Leu Asp Lys Gln Lys Lys Lys
            210                 215                 220

Thr Lys Met Thr Asp Glu Glu Ile Met Glu Lys Leu Arg Thr Ile Val
225                 230                 235                 240

Ser Ile Gly Asp Pro Lys Lys Lys Tyr Thr Arg Tyr Glu Lys Ile Gly
                    245                 250                 255

Gln Gly Ala Ser Gly Thr Val Phe Thr Ala Thr Asp Val Ala Leu Gly
                260                 265                 270

Gln Glu Val Ala Ile Lys Gln Ile Asn Leu Gln Lys Gln Pro Lys Lys
            275                 280                 285

Glu Leu Ile Ile Asn Glu Ile Leu Val Met Lys Glu Leu Lys Asn Pro
            290                 295                 300

Asn Ile Val Asn Phe Leu Asp Ser Tyr Leu Val Gly Asp Glu Leu Phe
305                 310                 315                 320

Val Val Met Glu Tyr Leu Ala Gly Gly Ser Leu Thr Asp Val Val Thr
                    325                 330                 335

Glu Thr Cys Met Asp Glu Ala Gln Ile Ala Ala Val Cys Arg Glu Cys
                340                 345                 350

Leu Gln Ala Leu Glu Phe Leu His Ala Asn Gln Val Ile His Arg Asp
            355                 360                 365

Ile Lys Ser Asp Asn Val Leu Leu Gly Met Glu Gly Ser Val Lys Leu
            370                 375                 380

Thr Asp Phe Gly Phe Cys Ala Gln Ile Thr Pro Glu Gln Ser Lys Arg
385                 390                 395                 400

Ser Thr Met Val Gly Thr Pro Tyr Trp Met Ala Pro Glu Val Val Thr
                    405                 410                 415

Arg Lys Ala Tyr Gly Pro Lys Val Asp Ile Trp Ser Leu Gly Ile Met
                420                 425                 430

Ala Ile Glu Met Val Glu Gly Glu Pro Pro Tyr Leu Asn Glu Asn Pro
            435                 440                 445

Leu Arg Ala Leu Tyr Leu Ile Ala Thr Asn Gly Thr Pro Glu Leu Gln
```

```
                   450                 455                 460

Asn Pro Glu Lys Leu Ser Pro Ile Phe Arg Asp Phe Leu Asn Arg Cys
465                 470                 475                 480

Leu Glu Met Asp Val Glu Lys Arg Gly Ser Ala Lys Glu Leu Leu Gln
                485                 490                 495

His Pro Phe Leu Lys Leu Ala Lys Pro Leu Ser Ser Leu Thr Pro Leu
            500                 505                 510

Ile Met Ala Ala Lys Glu Ala Met Lys Ser Asn Arg
            515                 520

<210> SEQ ID NO 2
<211> LENGTH: 25
<212> TYPE: RNA
<213> ORGANISM: Homo sapiens

<400> SEQUENCE: 2
gcgaccggau cauacgaaau caauu                                            25

<210> SEQ ID NO 3
<211> LENGTH: 545
<212> TYPE: PRT
<213> ORGANISM: Homo sapiens

<400> SEQUENCE: 3

Met Ser Asn Asn Gly Leu Asp Ile Gln Asp Lys Pro Pro Ala Pro Pro
1               5                   10                  15

Met Arg Asn Thr Ser Thr Met Ile Gly Ala Gly Ser Lys Asp Ala Gly
            20                  25                  30

Thr Leu Asn His Gly Ser Lys Pro Leu Pro Pro Asn Pro Glu Glu Lys
        35                  40                  45

Lys Lys Lys Asp Arg Phe Tyr Arg Ser Ile Leu Pro Gly Asp Lys Thr
    50                  55                  60

Asn Lys Lys Lys Glu Lys Glu Arg Pro Glu Ile Ser Leu Pro Ser Asp
65                  70                  75                  80

Phe Glu His Thr Ile His Val Gly Phe Asp Ala Val Thr Gly Glu Phe
                85                  90                  95

Thr Gly Met Pro Glu Gln Trp Ala Arg Leu Leu Gln Thr Ser Asn Ile
            100                 105                 110

Thr Lys Ser Glu Gln Lys Lys Asn Pro Gln Ala Val Leu Asp Val Leu
        115                 120                 125

Glu Phe Tyr Asn Ser Lys Lys Thr Ser Asn Ser Gln Lys Tyr Met Ser
    130                 135                 140

Phe Thr Asp Lys Ser Ala Glu Asp Tyr Asn Ser Ser Asn Ala Leu Asn
145                 150                 155                 160

Val Lys Ala Val Ser Glu Thr Pro Ala Val Pro Pro Val Ser Glu Asp
                165                 170                 175

Glu Asp Asp Asp Asp Asp Ala Thr Pro Pro Pro Val Ile Ala Pro Arg
            180                 185                 190

Arg Pro Glu His Thr Lys Ser Val Tyr Thr Arg Ser Val Ile Glu Pro
        195                 200                 205

Leu Pro Val Thr Pro Thr Arg Asp Val Ala Thr Ser Pro Ile Ser Pro
    210                 215                 220

Thr Glu Asn Asn Thr Thr Pro Pro Asp Ala Leu Thr Arg Asn Thr Glu
225                 230                 235                 240

Lys Gln Lys Lys Lys Pro Lys Met Ser Asp Glu Glu Ile Leu Glu Lys
                245                 250                 255
```

```
Leu Arg Ser Ile Val Ser Val Gly Asp Pro Lys Lys Tyr Thr Arg
            260                 265                 270

Phe Glu Lys Ile Gly Gln Gly Ala Ser Gly Thr Val Tyr Thr Ala Met
            275                 280                 285

Asp Val Ala Thr Gly Gln Glu Val Ala Ile Lys Gln Met Asn Leu Gln
            290                 295                 300

Gln Gln Pro Lys Lys Glu Leu Ile Ile Asn Glu Ile Leu Val Met Arg
305                 310                 315                 320

Glu Asn Lys Asn Pro Asn Ile Val Asn Tyr Leu Asp Ser Tyr Leu Val
                325                 330                 335

Gly Asp Glu Leu Trp Val Val Met Glu Tyr Leu Ala Gly Gly Ser Leu
            340                 345                 350

Thr Asp Val Val Thr Glu Thr Cys Met Asp Glu Gly Gln Ile Ala Ala
            355                 360                 365

Val Cys Arg Glu Cys Leu Gln Ala Leu Glu Phe Leu His Ser Asn Gln
            370                 375                 380

Val Ile His Arg Asp Ile Lys Ser Asp Asn Ile Leu Leu Gly Met Asp
385                 390                 395                 400

Gly Ser Val Lys Leu Thr Asp Phe Gly Phe Cys Ala Gln Ile Thr Pro
                405                 410                 415

Glu Gln Ser Lys Arg Ser Thr Met Val Gly Thr Pro Tyr Trp Met Ala
            420                 425                 430

Pro Glu Val Val Thr Arg Lys Ala Tyr Gly Pro Lys Val Asp Ile Trp
            435                 440                 445

Ser Leu Gly Ile Met Ala Ile Glu Met Ile Glu Gly Glu Pro Pro Tyr
            450                 455                 460

Leu Asn Glu Asn Pro Leu Arg Ala Leu Tyr Leu Ile Ala Thr Asn Gly
465                 470                 475                 480

Thr Pro Glu Leu Gln Asn Pro Glu Lys Leu Ser Ala Ile Phe Arg Asp
                485                 490                 495

Phe Leu Asn Arg Cys Leu Glu Met Asp Val Glu Lys Arg Gly Ser Ala
            500                 505                 510

Lys Glu Leu Leu Gln His Gln Phe Leu Lys Ile Ala Lys Pro Leu Ser
            515                 520                 525

Ser Leu Thr Pro Leu Ile Ala Ala Ala Lys Glu Ala Thr Lys Asn Asn
            530                 535                 540

His
545

<210> SEQ ID NO 4
<211> LENGTH: 25
<212> TYPE: RNA
<213> ORGANISM: Homo sapiens

<400> SEQUENCE: 4
gaugagaaau accagcacua ugauu                                    25
```

INHIBITION OF EMT INDUCTION IN TUMOR CELLS BY ANTI-CANCER AGENTS

CROSS-REFERENCE TO RELATED APPLICATIONS

This application claims the benefit of U.S. Provisional Application No. 61/068,566, filed Mar. 7, 2008, which is herein incorporated by reference in its entirety.

BACKGROUND OF THE INVENTION

The present invention is directed to methods for the identification of new anti-cancer agents that inhibit an epithelial-mesenchymal transition (EMT) in tumor cells, and their use in treating cancer patients, particularly in combination with other agents such as EGFR or IGF-1R kinase inhibitors that can be less effective at inhibiting tumor cells that have undergone an EMT. Cancer is a generic name for a wide range of cellular malignancies characterized by unregulated growth, lack of differentiation, and the ability to invade local tissues and metastasize. These neoplastic malignancies affect, with various degrees of prevalence, every tissue and organ in the body.

An anti-neoplastic drug would ideally kill cancer cells selectively, with a wide therapeutic index relative to its toxicity towards non-malignant cells. It would also retain its efficacy against malignant cells, even after prolonged exposure to the drug. Unfortunately, none of the current chemotherapies possess such an ideal profile. Instead, most possess very narrow therapeutic indexes. Furthermore, cancerous cells exposed to slightly sub-lethal concentrations of a chemotherapeutic agent will very often develop resistance to such an agent, and quite often cross-resistance to several other antineoplastic agents as well.

A multitude of therapeutic agents have been developed over the past few decades for the treatment of various types of cancer. The most commonly used types of anticancer agents include: DNA-alkylating agents (e.g., cyclophosphamide, ifosfamide), antimetabolites (e.g., methotrexate, a folate antagonist, and 5-fluorouracil, a pyrimidine antagonist), microtubule disrupters (e.g., vincristine, vinblastine, paclitaxel), DNA intercalators (e.g., doxorubicin, daunomycin, cisplatin), and hormone therapy (e.g., tamoxifen, flutamide). More recently, gene targeted therapies, such as protein-tyrosine kinase inhibitors have increasingly been used in cancer therapy (de Bono J. S. and Rowinsky, E. K. (2002) Trends in Mol. Medicine. 8:S19-S26; Dancey, J. and Sausville, EBA. (2003) Nature Rev. Drug Discovery 2:92-313). Such approaches, such as the EGFR kinase inhibitor erlotinib, are generally associated with reduced toxicity compared with conventional cytotoxic agents. They are therefore particularly appropriate for use in combination regimens. In pancreatic cancer, phase III trials have shown that first-line erlotinib treatment in combination with gemcitabine improves survival.

The epidermal growth factor receptor (EGFR) family comprises four closely related receptors (HER1/EGFR, HER2, HER3 and HER4) involved in cellular responses such as differentiation and proliferation. Over-expression of the EGFR kinase, or its ligand TGF-alpha, is frequently associated with many cancers, including breast, lung, colorectal, ovarian, renal cell, bladder, head and neck cancers, glioblastomas, and astrocytomas, and is believed to contribute to the malignant growth of these tumors. A specific deletion-mutation in the EGFR gene (EGFRvIII) has also been found to increase cellular tumorigenicity. Activation of EGFR stimulated signaling pathways promote multiple processes that are potentially cancer-promoting, e.g. proliferation, angiogenesis, cell motility and invasion, decreased apoptosis and induction of drug resistance. Increased HER1/EGFR expression is frequently linked to advanced disease, metastases and poor prognosis. For example, in NSCLC and gastric cancer, increased HER1/EGFR expression has been shown to correlate with a high metastatic rate, poor tumor differentiation and increased tumor proliferation.

Mutations which activate the receptor's intrinsic protein tyrosine kinase activity and/or increase downstream signaling have been observed in NSCLC and glioblastoma. However the role of mutations as a principle mechanism in conferring sensitivity to EGF receptor inhibitors, for example erlotinib (TARCEVA®) or gefitinib (IRESSA™), has been controversial. Recently, a mutant form of the full length EGF receptor has been reported to predict responsiveness to the EGF receptor tyrosine kinase inhibitor gefitinib (Paez, J. G. et al. (2004) Science 304:1497-1500; Lynch, T. J. et al. (2004) N. Engl. J. Med. 350:2129-2139). Cell culture studies have shown that cell lines which express the mutant form of the EGF receptor (i.e. H3255) were more sensitive to growth inhibition by the EGF receptor tyrosine kinase inhibitor gefitinib, and that much higher concentrations of gefitinib was required to inhibit the tumor cell lines expressing wild type EGF receptor. These observations suggests that specific mutant forms of the EGF receptor may reflect a greater sensitivity to EGF receptor inhibitors, but do not identify a completely non-responsive phenotype.

Erlotinib (e.g. erlotinib HCl, also known as TARCEVA® or OSI-774) is an orally available inhibitor of EGFR kinase. In vitro, erlotinib has demonstrated substantial inhibitory activity against EGFR kinase in many human tumor cell lines. In a phase III trial, erlotinib monotherapy significantly prolonged survival, delayed disease progression and delayed worsening of lung cancer-related symptoms in patients with advanced, treatment-refractory NSCLC (Shepherd, F. et al. (2005) N. Engl. J. Med. 353(2):123-132). In November 2004 the U.S. Food and Drug Administration (FDA) approved TARCEVA® for the treatment of patients with locally advanced or metastatic non-small cell lung cancer (NSCLC) after failure of at least one prior chemotherapy regimen.

The development for use as anti-tumor agents of compounds that directly inhibit the kinase activity of IGF-1R, as well as antibodies that reduce IGF-1R kinase activity by blocking IGF-1R activation or antisense oligonucleotides that block IGF-1R expression, are also areas of intense research effort (e.g. see Larsson, O. et al (2005) Brit. J. Cancer 92:2097-2101; Ibrahim, Y. H. and Yee, D. (2005) Clin. Cancer Res. 11:944s-950s; Mitsiades, C. S. et al. (2004) Cancer Cell 5:221-230; Camirand, A. et al. (2005) Breast Cancer Research 7:R570-R579 (DOI 10.1186/bcr1028); Camirand, A. and Pollak, M. (2004) Brit. J. Cancer 90:1825-1829; Garcia-Echeverria, C. et al. (2004) Cancer Cell 5:231-239).

IGF-1R is a transmembrane RTK that binds primarily to IGF-1 but also to IGF-II and insulin with lower affinity. Binding of IGF-1 to its receptor results in receptor oligomerization, activation of tyrosine kinase, intermolecular receptor autophosphorylation and phosphorylation of cellular substrates (major substrates are IRS1 and Shc). The ligand-activated IGF-1R induces mitogenic activity in normal cells and plays an important role in abnormal growth. A major physiological role of the IGF-1 system is the promotion of normal growth and regeneration. Overexpressed IGF-1R (type 1 insulin-like growth factor receptor) can initiate mitogenesis and promote ligand-dependent neoplastic transformation.

Furthermore, IGF-1R plays an important role in the establishment and maintenance of the malignant phenotype. Unlike the epidermal growth factor (EGF) receptor, no mutant oncogenic forms of the IGF-1R have been identified. However, several oncogenes have been demonstrated to affect IGF-1 and IGF-1R expression. The correlation between a reduction of IGF-1R expression and resistance to transformation has been seen. Exposure of cells to the mRNA antisense to IGF-1R RNA prevents soft agar growth of several human tumor cell lines. IGF-1R abrogates progression into apoptosis, both in vivo and in vitro. It has also been shown that a decrease in the level of IGF-1R below wild-type levels causes apoptosis of tumor cells in vivo. The ability of IGF-1R disruption to cause apoptosis appears to be diminished in normal, non-tumorigenic cells.

The IGF-1 pathway in human tumor development has an important role. IGF-1R overexpression is frequently found in various tumors (breast, colon, lung, sarcoma) and is often associated with an aggressive phenotype. High circulating IGF1 concentrations are strongly correlated with prostate, lung and breast cancer risk. Furthermore, IGF-1R is required for establishment and maintenance of the transformed phenotype in vitro and in vivo (Baserga R. *Exp. Cell. Res.*, 1999, 253, 1-6). The kinase activity of IGF-1R is essential for the transforming activity of several oncogenes: EGFR, PDGFR, SV40 T antigen, activated Ras, Raf, and v-Src. The expression of IGF-1R in normal fibroblasts induces neoplastic phenotypes, which can then form tumors in vivo. IGF-1R expression plays an important role in anchorage-independent growth. IGF-1R has also been shown to protect cells from chemotherapy-, radiation-, and cytokine-induced apoptosis. Conversely, inhibition of endogenous IGF-1R by dominant negative IGF-1R, triple helix formation or antisense expression vector has been shown to repress transforming activity in vitro and tumor growth in animal models.

During most cancer metastases, an important change occurs in a tumor cell known as the epithelial-mesenchymal transition (EMT) (Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515)). EMT does not occur in healthy cells except during embryogenesis. Epithelial cells, which are bound together tightly and exhibit polarity, give rise to mesenchymal cells, which are held together more loosely, exhibit a loss of polarity, and have the ability to travel. These mesenchymal cells can spread into tissues surrounding the original tumor, as well as separate from the tumor, invade blood and lymph vessels, and travel to new locations where they divide and form additional tumors. Recent research has demonstrated that epithelial cells respond well to EGFR and IGF-1R kinase inhibitors, but that after an EMT the resulting mesenchymal-like cells are much less sensitive to such inhibitors. (e.g. Thompson, S. et al. (2005) Cancer Res. 65(20):9455-9462; U.S. Patent Application 60/997,514). Thus there is a pressing need for anti-cancer agents that can prevent or reverse tumor cell EMT events (e.g. stimulate a mesenchymal to epithelial transition (MET)), or inhibit the growth of the mesenchymal-like tumor cells resulting from EMT. Such agents should be particularly useful when used in conjunction with other anti-cancer drugs such as EGFR and IGF-1R kinase inhibitors.

Snail is a Zn-finger transcriptional repressor and a master regulator of the epithelial-mesenchymal transition (EMT) in development and cancer progression [Peinado, H., D. et al. Nat Rev Cancer, 2007. 7(6): p. 415-28]. Snail has been described as a direct repressor of E-cadherin expression through binding to the conserved E-boxes in the proximal promoter region. Snail can also upregulate the expression of ZEB1, another EMT driver and E-box binding repressor of E-cadherin and other epithelial genes [Aigner, K., et al., Oncogene, 2007, 26(49):6979-88; Guaita, S., et al., J Biol Chem, 2002. 277(42): p. 39209-16]. The expression of Snail induces complete EMT and increases cellular migration and invasion in different physiological and pathological settings. Recent studies have implicated Snail expression and function with tumor recurrence of breast cancer [Moody, S. E., et al. Cancer Cell, 2005. 8(3): p. 197-209] in addition to increased metastasis and chemoresistance of pancreatic cancer [Yin, T., et al., J Surg Res, 2007. 141(2): p. 196-203].

Stimuli that induce EMT such as TGFβ, HGF, Shh, Wnt seem to do so by upregulating the expression [Cho, H. J., et al., Biochem Biophys Res Commun, 2007. 353(2): p. 337-43; Grotegut, S., et al., Embo J, 2006. 25(15): p. 3534-45; Li, X., et al., Oncogene, 2006. 25(4): p. 609-21] and stability [Yook, J. I., et al., Nat Cell Biol, 2006. 8(12): p. 1398-406] of Snail. GSK-3β phosphorylates Snail at two consensus motifs; phosphorylation of the first motif (residues 96-104) regulates Snail's ubiquitination and degradation while phosphorylation of the second motif (residues107-119) favors its exclusion from the nucleus [Zhou, B. P., et al., Nat Cell Biol, 2004. 6(10): p. 931-40]. On the other hand, it has been demonstrated that phosphorylation of Snail by the p21-activated kinase 1 (PAK1) on Ser-246 favors shuttling of Snail to the nucleus thereby enhancing its repressor function [Yang, Z., et al., Cancer Res, 2005. 65(8): p. 3179-84].

PAK1 is a group I p21-activated serine/threonine kinase and is highly homologous (~92% amino acid identity in the kinase domain) to the two other members PAK2 and PAK3. While PAK1 and PAK2 show universal expression, PAK3's expression is restricted to central nervous system tissues. PAK1-3 are generally thought to phosphorylate overlapping sets of substrates. In addition to Snail, two other EMT-related proteins have recently been identified as putative PAK1 substrates, integrin-linked kinase ILK and heterogeneous nuclear ribonucleoprotein hnRNP-A/B (a.k.a. CBF-A) [Acconcia, F., et al., Proc Natl Acad Sci USA, 2007. 104(16): p. 6782-7; Meng, Q., et al. Proc Natl Acad Sci USA, 2007. 104(14): p. 5866-71]. Both ILK and hnRNP-A/B cause full EMT upon overexpression in epithelial cells [Somasiri, A., et al., J Cell Sci, 2001. 114(Pt 6): p. 1125-36; Venkov, C. D., et al., J Clin Invest, 2007. 117(2): p. 482-91]. It has not been shown whether any of these substrates is phosphorylatable by PAK2 and hence whether PAK2 activity can impact EMT. PAK2 has however been previously linked to the TGFβ-mediated morphological transformation of fibroblasts into myofibroblasts [Wilkes, M. C., et al. Mol Cell Biol, 2003. 23(23): p. 8878-89], a process akin to EMT in epithelial cells. The mentioned study demonstrated that TGFβ activates PAK2 only in fibroblast cells and not in epithelial cells [Wilkes, M. C., et al., Mol Cell Biol, 2003. 23(23): p. 8878-89]. PAK2 kinase inhibition has also been suggested as a potential method for treating cancer (US Patent Application Publication US 2005/0080002).

The invention described herein provides methods for the identification of new anti-cancer agents that inhibit PAK2 and EMT in tumor cells, and their use in treating cancer patients. The invention described herein also provides new anti-cancer combination therapies that are an improvement on the efficacy of either EGFR kinase inhibitors or or IGF-1R kinase inhibitors when administered alone. In particular, the present invention is directed to methods of combined treatment of cancer with an epidermal growth factor receptor (EGFR) kinase inhibitor (or an IGF-1R kinase inhibitor) and an inhibitor of PAK2 kinase.

SUMMARY OF THE INVENTION

The present invention provides method of identifying an agent that inhibits tumor cells from undergoing an epithelial to mesenchymal transition, comprising: providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors and that inhibit tumor cells from undergoing an epithelial to mesenchymal transition. The present invention also provides similar methods where the identified PAK2 kinase inhibitor is also shown to inhibit PAK1 kinase. The present invention also provides compositions comprising said agents that inhibit PAK2 kinase, and methods for their preparation and use.

The present invention also provides a method of identifying an agent that inhibits tumor cells from undergoing an epithelial to mesenchymal transition, comprising: providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors, determining whether an agent that inhibits PAK2 kinase also inhibits tumor cells from undergoing an epithelial to mesenchymal transition, by contacting a sample of tumor cells with said agent, comparing in said sample of tumor cells induced to undergo EMT, the level of a biomarker whose level is indicative of the EMT status of the tumor cells to the level of the same biomarker in an identical sample of tumor cells induced to undergo EMT but not contacted with the agent that inhibits PAK2 kinase, and thus identifying the agent that inhibits PAK2 kinase as an agent that inhibits tumor cells from undergoing an epithelial to mesenchymal transition. The present invention also provides similar methods where the identified PAK2 kinase inhibitor is also shown to inhibit PAK1 kinase. The present invention also provides compositions comprising said agents that inhibit PAK2 kinase, and methods for their preparation and use. The present invention also provides methods of identifying inhibitors of PAK2 kinase that impair tumor cell mobility, and thus inhibits tumorigenicity.

The present invention also provides a method of inhibiting tumor cells from undergoing an epithelial to mesenchymal transition in a mammal in recognized need of such treatment, said method comprising administering to said mammal a pharmaceutical composition comprising an inhibitor of PAK2 kinase, wherein said administering is in an amount effective to inhibit epithelial to mesenchymal transition of tumor cells in said mammal. In one embodiment of this method the inhibitor of PAK2 kinase is also an inhibitor of PAK1 kinase.

The present invention also provides a method for treating tumors or tumor metastases in a patient, comprising administering to said patient simultaneously or sequentially a therapeutically effective amount of a combination of an anti-cancer agent that preferentially inhibits epithelial tumor cells, and an inhibitor of PAK2 kinase, wherein said administering is in an amount effective to inhibit epithelial tumor cell growth in said mammal, and to inhibit EMT in said epithelial tumor cells.

BRIEF DESCRIPTION OF THE FIGURES

FIG. 9: Deduced 524 amino acid sequence of human PAK2 kinase (SEQ ID NO:1).

FIG. 10: Deduced 545 amino acid sequence of human PAK1 kinase (SEQ ID NO:3).

DETAILED DESCRIPTION OF THE INVENTION

Figure 1:
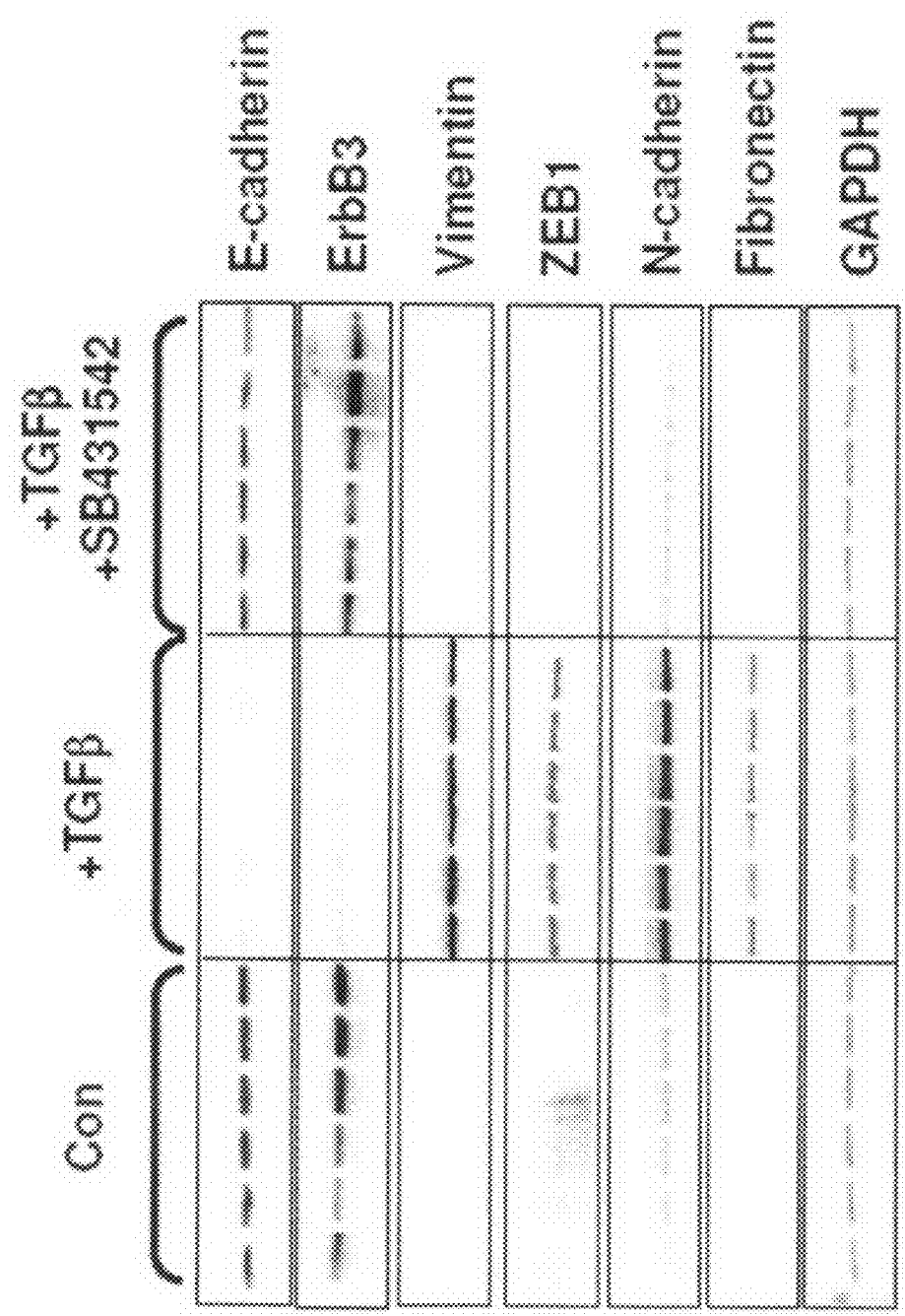
FIG. 1: TGFβ3 induces EMT in H358 NSCLC cells. H358 cells were treated with TGFβ3 (1 nM, 7 days) in the presence or absence of the TGFβ receptor kinase inhibitor SB43 1542. Protein extracts were analyzed by western blot using the indicated antibodies.

The term "cancer" in an animal refers to the presence of cells possessing characteristics typical of cancer-causing cells, such as uncontrolled proliferation, immortality, metastatic potential, rapid growth and proliferation rate, and certain characteristic morphological features. Often, cancer cells will be in the form of a tumor, but such cells may exist alone within an animal, or may circulate in the blood stream as independent cells, such as leukemic cells.

"Cell growth", as used herein, for example in the context of "tumor cell growth", unless otherwise indicated, is used as commonly used in oncology, where the term is principally associated with growth in cell numbers, which occurs by means of cell reproduction (i.e. proliferation) when the rate the latter is greater than the rate of cell death (e.g. by apoptosis or necrosis), to produce an increase in the size of a population of cells, although a small component of that growth may in certain circumstances be due also to an increase in cell size or cytoplasmic volume of individual cells. An agent that inhibits cell growth can thus do so by either inhibiting proliferation or stimulating cell death, or both, such that the equilibrium between these two opposing processes is altered.

"Tumor growth" or "tumor metastases growth", as used herein, unless otherwise indicated, is used as commonly used in oncology, where the term is principally associated with an increased mass or volume of the tumor or tumor metastases, primarily as a result of tumor cell growth.

"Abnormal cell growth", as used herein, unless otherwise indicated, refers to cell growth that is independent of normal regulatory-mechanisms (e.g., loss of contact inhibition). This includes the abnormal growth of: (1) tumor cells (tumors) that proliferate by expressing a mutated tyrosine kinase or overexpression of a receptor tyrosine kinase; (2) benign and malignant cells of other proliferative diseases in which aberrant tyrosine kinase activation occurs; (4) any tumors that proliferate by receptor tyrosine kinases; (5) any tumors that proliferate by aberrant serine/threonine kinase activation; and (6) benign and malignant cells of other proliferative diseases in which aberrant serine/threonine kinase activation occurs.

The term "treating" as used herein, unless otherwise indicated, means reversing, alleviating, inhibiting the progress of, or preventing, either partially or completely, the growth of tumors, tumor metastases, or other cancer-causing or neoplastic cells in a patient. The term "treatment" as used herein, unless otherwise indicated, refers to the act of treating.

The phrase "a method of treating" or its equivalent, when applied to, for example, cancer refers to a procedure or course of action that is designed to reduce or eliminate the number of cancer cells in an animal, or to alleviate the symptoms of a cancer. "A method of treating" cancer or another proliferative disorder does not necessarily mean that the cancer cells or other disorder will, in fact, be eliminated, that the number of cells or disorder will, in fact, be reduced, or that the symptoms of a cancer or other disorder will, in fact, be alleviated. Often, a method of treating cancer will be performed even with a low likelihood of success, but which, given the medical history and estimated survival expectancy of an animal, is nevertheless deemed an overall beneficial course of action.

As used herein, the term "patient" preferably refers to a human in need of treatment with an anticancer agent, and more preferably a human in need of such a treatment to treat cancer or a tumor, or a precancerous condition or lesion. However, the term "patient" can also refer to non-human animals, preferably mammals such as dogs, cats, horses, cows, pigs, sheep and non-human primates, among others, that are in need of treatment with an anticancer agent. The cancer or tumor may be any of those listed herein.

The term "therapeutically effective agent" means a composition that will elicit the biological or medical response of a tissue, system, animal or human that is being sought by the researcher, veterinarian, medical doctor or other clinician.

The term "therapeutically effective amount" or "effective amount" means the amount of the subject compound or combination that will elicit the biological or medical response of a tissue, system, animal or human that is being sought by the researcher, veterinarian, medical doctor or other clinician.

The term "PAK2 kinase" as used herein, unless otherwise indicated, means a polypeptide encoded by the human gene defined as NCBI GeneID: 5062 (also known as p21-activated kinase 2), or a polypeptide encoded by a homologous mammalian PAK2 kinase gene (e.g. GeneID: 460965 (Pan troglodytes), GeneID: 612814 (Canis lupus familiaris), GeneID: 224105 (*Mus musculus*), GeneID: 29432 (*Rattus norvegicus*)), or an active kinase fragment or domain of any of the above.

The term "PAK1 kinase" as used herein, unless otherwise indicated, means a polypeptide encoded by the human gene defined as NCBI GeneID: 5058 (also known as p21/Cdc42/Rac 1-activated kinase 1), or a polypeptide encoded by a homologous mammalian PAK1 kinase gene (e.g. GeneID: 451-439 (Pan troglodytes), GeneID: 607885 (Canis lupus familiaris), GeneID: 18479 (*Mus musculus*), GeneID: 29431 (*Rattus norvegicus*)), or an active kinase fragment or domain of any of the above.

The present invention derives from research that provided methods for determining which tumors will respond most effectively to treatment with protein-tyrosine kinase inhibitors (e.g. Thompson, S. et al. (2005) Cancer Res. 65(20): 9455-9462; Mulvihill, M. J. et al. (2007) Bioorganic & Medicinal Chemistry Letters 17:1091-1097) based on whether the tumor cells have undergone an epithelial to mesenchymal transition ("EMT"; Thiery, J. P. (2002) Nat. Rev. Cancer 2:442-454; Savagner, P. (2001) Bioessays 23:912-923; Kang Y. and Massague, J. (2004) Cell 118:277-279; Julien-Grille, S., et al. Cancer Research 63:2172-2178; Bates, R. C. et al. (2003) Current Biology 13:1721-1727; Lu Z., et al. (2003) Cancer Cell. 4(6):499-515). This research demonstrated that epithelial tumor cells respond well to EGFR and IGF-1R kinase inhibitors, but that after an EMT the resulting mesenchymal-like cells are much less sensitive to such inhibitors. Biomarkers can be used to determine whether tumor cells have undergone an EMT (Thomson, S. et al. (2005) Cancer Res. 65(20):9455-9462). As a result of such work it became apparent that new therapeutic approaches would be necessary to find agents that were capable of inhibiting the transition to or growth of such mesenchymal-like cells, which are thought to be an important element in the invasive and metastatic properties of tumors. The data described herein describes new methods for identifying agents that inhibit EMT, and for treatment of patients with such agents.

The data presented in the Examples herein below demonstrate that specific siRNA inhibitors of the expression of PAK2 kinase are agents that inhibit tumor cells from undergoing an epithelial to mesenchymal transition (EMT), impair tumor cell mobility, and thus inhibit tumorigenicity. Specific siRNA inhibitors of the expression of PAK1 kinase did not have a similar effect, but when used in combination with the siRNA inhibitors of the expression of PAK2 kinase, they augmented the inhibition of EMT. Alternative agents that similarly inhibit the expression of the protein product encoded by the PAK2 gene (or both PAK2 and PAK1 genes), or inhibit the biological activity of the expressed protein (e.g. its phosphotransferase activity), such as antisense molecules, ribozymes, aptamers, or small organic molecule enzyme inhibitors (e.g. protein kinase inhibitors) that are inhibitors of PAK2 kinase in tumor cells, will similarly be agents that inhibit tumor cells from undergoing an epithelial to mesenchymal transition, impair tumor cell mobility, and thus inhibit tumorigenicity, and thus will be effective in the methods of treatment described herein that involve administering a PAK2 inhibitor. The anti-tumor effects of a combination of an EGFR or IGF-1R kinase inhibitor with such an agent that inhibits PAK2 kinase should be superior to the anti-tumor effects of these receptor kinase inhibitors by themselves, since such a combination should effectively inhibit both epithelial and mesenchymal-like tumor cells, and thus co-administration of such agents with EGFR or IGF-1R kinase inhibitors should be effective for treatment of patients with advanced cancers such as NSCL, pancreatic, colon or breast cancers.

Inhibition of the expression of PAK2 kinase does not appear to affect the induction during EMT of some classical mesenchymal biomarkers (e.g. vimentin). Nevertheless, it appears that the effect of inhibition of the expression of PAK2 kinase on epithelial biomarkers is sufficient to inhibit the cells from undergoing a complete EMT, and thus reduce their tumorigenicity.

Accordingly, the present invention provides a method of identifying an agent that inhibits tumor cells from undergoing an epithelial to mesenchymal transition, comprising: providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors and that inhibit tumor cells from undergoing an epithelial to mesenchymal transition. One embodiment of this method comprises, after the step of determining whether the test agent inhibits PAK2 kinase, the additional steps of providing a preparation containing a PAK1 kinase, incubating the preparation with an agent identified as inhibiting PAK2 kinase, under conditions to permit binding of the test agent to the PAK1 kinase; determining whether the agent identified as inhibiting PAK2 kinase also inhibits the PAK1 kinase by detecting a decrease in the phosphotransferase activity of the PAK1 kinase, thus identifying said agents as inhibitors of both PAK1 and PAK2 kinases.

The present invention also provides a method of identifying an agent that inhibits tumor cells from undergoing an epithelial to mesenchymal transition, comprising providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors, determining whether an agent that inhibits PAK2 kinase also inhibits tumor cells from undergoing an epithelial to mesenchymal transition, by contacting a sample of tumor cells with said agent, comparing in said sample of tumor cells induced to undergo EMT, the level of a biomarker whose level is indicative of the EMT status of the tumor cells to the level of the same biomarker in an identical sample of tumor cells induced to undergo EMT but not contacted with the agent that inhibits PAK2 kinase, and thus identifying the agent that inhibits PAK2 kinase as an agent that inhibits tumor cells from undergoing an epithelial to mesenchymal transition. In one embodiment of this method the test agent is a small organic molecule. In another embodiment of this method, the epithelial to mesenchymal transition involves transcriptional repression by the protein Snail.

In any of the methods of this invention, the tumor cells may be induced to undergo EMT using, any agent known to induce EMT for the given tumor cell type. For example, the protein TGF-beta may be employed. "TGFbeta", as used herein means TGFbeta-1, TGFbeta-2, or TGFbeta-3 (Schmierer, B. and Hill, C. (2007) Nat Rev Mol Cell Biol. 8(12):970-82), or heterodimers thereof. The TGF-beta is preferably human, but TGF-beta from other species that are active in promoting EMT in the tumor cells may also be used (e.g. from mouse, rat, pig, rabbit, chicken, bovine). Additional EMT-inducing agents that may be used include for example, the proteins HGF (Lamorte, L. et al (2002) Mol Biol Cell. 13(5): p. 1449-61), Hedgehog (Feldmann, G. et al (2007) Cancer Res. 67(5): p. 2187-96), Wnt (Yook, J. et al (2006) Nat Cell Biol. 8(12): p. 0.1398-406), IL-1 (Chaudhuri, V. et al (2007) J Cutan Pathol. 34(2): p. 146-53), Oncostatin M (Pollack, V. et al (2007) Am J Physiol Renal Physiol. 293(5): p. F1714-26), EGF (Solic, N. and Davies, D. (1997) Exp Cell Res. 234(2): p. 465-76), Amphiregulin (Chung, (2005) E. Exp Cell Res. 309(1): p. 149-60), HB-EGF (Wang, F. et al (2007) Cancer Res. 67(18): p. 8486-93), MSP (Camp, E., (2007) Cancer. 109(6): p. 1030-9), Wnt5a (Dissanayake, S. (2007) J Biol. Chem. 282(23): p. 17259-71, Ripka, S. (2007) Carcinogenesis. 28(6): p. 1178-87), and TNF-alpha (Bates, R. and Mercurio, A. (2003) Mol Biol Cell. 14(5): p. 1790-800). Alternatively, the tumor cells may be engineered to indicibly-express a protein that causes the cells to undergo EMT, e.g. Snail. The inducible expression may be for example, a tet-on or tet-off system in which the level of Snail, and thus EMT induction, can be modulated by the presence or absence of a tetracycline analogue such as doxycycline (e.g. see Guaita, S. et al (2002) J. Biol. Chem. 277(42):39209-39216).

One embodiment of the preceding method of identifying an agent that inhibits tumor cells from undergoing an epithelial to mesenchymal transition comprises, after the step of determining whether the test agent inhibits PAK2 kinase, the additional steps of providing a preparation containing a PAK1 kinase, incubating the preparation with an agent identified as inhibiting PAK2 kinase, under conditions to permit binding of the test agent to the PAK1 kinase; determining whether the agent identified as inhibiting PAK2 kinase also inhibits the PAK1 kinase by detecting a decrease in the phosphotransferase activity of the PAK1 kinase, thus identifying said agents as inhibitors of both PAK1 and PAK2 kinases. Thus, in this embodiment, agents are identified as inhibitors of both PAK2 and PAK1 kinases prior to the step of determining whether an agent that inhibits PAK2 kinase also inhibits tumor cells from undergoing an epithelial to mesenchymal transition when a sample of tumor cells are contacted with said agent. As described herein, inhibition of PAK1 kinase augments the effect on EMT induction produced by inhibition of PAK2 alone, and thus a dual PAK1/PAK2 kinase inhibitor should be more efficacious, and thus preferred.

In any of the methods of the invention described herein the tumor cells for which an agent is sought to inhibit an epithelial to mesenchymal transition (e.g. in a patient with cancer) can be any tumor cells that can undergo an epithelial to mesenchymal transition, including human tumor cells from the major solid tumors, such as NSCLC, head and neck, colorectal, pancreatic, breast and ovarian tumor cells. Further examples of suitable tumor cells are described herein. In the methods described herein of identifying an agent that inhibits tumor cells from undergoing an epithelial to mesenchymal transition, the sample of tumor cells to be tested with inhibitors of PAK2 and/or PAK1 kinase may be cells in culture (e.g. monolayer culture; 3-dimensional cell cultures such as Matrigel™ cultures (Xiang, B. and Muthuswamy, S. (2006) Methods Enzymol. 406: p. 692-701), or soft agar culture, or cells in vivo (e.g. tumor xenografts), and may also be tumor cells from any of the major solid tumors, such as NSCLC, head and neck, colorectal, pancreatic, breast and ovarian tumor cells, or other tumor cells disclosed herein. The sample of tumor cells to be tested with inhibitors of PAK2 and/or PAK1 kinase is preferably of the same tumor type as the tumor cells for which an agent is sought to inhibit an epithelial to mesenchymal transition, though not necessarily so, as such inhibitors are anticipated to be effective on any tumor cell type that can undergo an epithelial to mesenchymal transition. Examples of tumor cells that may be used as the sample of tumor cells include the NSCLC cell line H358, breast cancer cell lines MCF7 (Hiscox, X. (2006) Int J. Cancer. 118(2): p. 290-301), T47D (Jorcyk, C. et al (2006) Cytokine. 33(6): p. 323-36), and MDA-MB-468 (Lester, R. (2007) J. Cell Biol. 178(3): p. 425-36), pancreatic cancer cell lines L3.6pl (Yang, A. et al (2006) Cancer Res. 66(1): p. 46-51), PANC-1, COLO-357, and IMIM-PC1 (Ellenrieder, V. (2001) Cancer Res. 61(10): p. 4222-8), and colon cancer cell lines HT29 (Yang, L. (2006) Cell. 127(1): p. 139-55), LIM 1863 (Bates, R. et al (2004) Exp Cell Res. 299(2):315-24), and KM12L4 (Yang, A. (2006) Clin Cancer Res. 12(14 Pt 1):4147-53).

The preparations described herein containing a PAK2 kinase or a PAK1 kinase can be, for example, a purified enzyme preparation, an isolated immune complex containing the kinase, or a cell expressing the PAK2 or PAK1 kinase. In one embodiment the PAK2 kinase is a polypeptide encoded by a nucleic acid that hybridizes under stringent conditions to the complement of the nucleic acid encoding a polypeptide having an amino acid sequence of SEQ ID NO: 1 (FIG. 9: human PAK2; Genbank Accession No. NP_002568), wherein the stringent conditions comprise incubating at 42° C. in a solution comprising 50% formamide, 5×SSC, and 1% SDS and washing at 65° C. in a solution comprising 0.2×SSC and 0.1% SDS. In one example of this embodiment, the PAK2 polypeptide comprises the amino acid sequence of SEQ ID NO: 1. In another example of this embodiment, the PAK2 polypeptide comprises the amino acid sequence of residues 249-500 of SEQ ID NO: 1 (i.e. a kinase domain fragment). In one embodiment the PAK1 kinase is a polypeptide encoded by a nucleic acid that hybridizes under stringent conditions to the complement of the nucleic acid encoding a polypeptide having an amino acid sequence of SEQ ID NO:3 (FIG. 10: human PAK1; Genbank Accession No. NP_002567), wherein the stringent conditions comprise incubating at 42° C. in a solution comprising 50% formamide, 5×SSC, and 1% SDS and washing at 65° C. in a solution comprising 0.2×SSC and 0.1% SDS. In one example of this embodiment, the PAK1 polypeptide comprises the amino acid sequence of SEQ ID NO:3. In another example of this embodiment, the PAK1 polypeptide comprises the amino acid sequence of residues 269-521 of SEQ ID NO:3 (i.e. a kinase domain fragment). In a further embodiment, the above PAK1 or PAK2 polypeptides can be attached to a heterologous polypeptide sequence, for example to assist in its detection and/or purification (e.g. a FLAG sequence, a GST tag, or several N-terminal histidine residues (e.g. 6-8); e.g. see International Patent Application Publication WO 2006/106326). In an alternative embodiment, the PAK1 or PAK2 polypeptides may be the corresponding animal PAK1 or PAK2 kinases that are homologous to the above-described human PAK1 or PAK2 kinases, from for example a mouse, rat, dog, monkey, rabbit, cow, or pig.

The present invention also provides a method of inhibiting tumor cells from undergoing an epithelial to mesenchymal transition in a mammal in recognized need of such treatment, said method comprising administering to said mammal a pharmaceutical composition comprising an inhibitor of PAK2 kinase, wherein said administering is in an amount effective to inhibit epithelial to mesenchymal transition of tumor cells in said mammal. In one embodiment of this method the inhibitor of PAK2 kinase is also an inhibitor of PAK1 kinase. In an alternative embodiment an inhibitor of PAK1 kinase is additionally administered as a separate compound. In an alternative embodiment, one or more other anti-cancer agents may additionally be administered to said mammal. Such anti-cancer agents include for example EGFR kinase inhibitors, such as erlotinib, and IGF-1R kinase inhibitors, such as OSI-906. Other anti-cancer agents include those additional agents described herein below.

In one embodiment of the preceding method of inhibiting tumor cells from undergoing an epithelial to mesenchymal transition, the kinase inhibitor is an siRNA that inhibits the expression of the PAK2 kinase gene. In one example of this embodiment, the siRNA targets the sequence of SEQ ID NO:3. In an alternative embodiment, the kinase inhibitor is an antisense nucleic acid that inhibits the expression of the PAK2 kinase gene. In an alternative embodiment, the PAK2 kinase inhibitor is a ribozyme that inhibits the expression of the PAK2 kinase gene. In an alternative embodiment, the PAK2 kinase inhibitor is a small organic molecule.

Examples of specific PAK2 and/or PAK1 kinase inhibitors that may be used in practicing the preceding method of inhibiting tumor cells from undergoing an epithelial to mesenchymal transition, and other methods of treatment described herein which specify use of a PAK2 and/or PAK1 kinase inhibitor, include, but are not limited to, indazole compounds, as described in US Patent Application Publications US 2006/0004043 and US 2005/0009876; 2-amido-thiazole-based compounds, as described in US Patent Application Publication US 2006/0052416; quinoloine- and isoquinoline-based compounds, as described in US Patent Application Publication US 2006/0009460; triazole-based compounds, as described in US Patent Application Publication US 2005/0288347; thiophene-based compounds, as described in US Patent Application Publication US 2005/0085531; hexahydro-cyclohepta-pyrrole oxindole compounds, as described in US Patent Application Publications US 2004/0186160; 3-pyrrol-pyridopyrazoles and 3-pyrrolyl-indazoles, as described in US Patent Application Publications US 2004/0092546; and substituted heterocycle compounds, as described in International Patent Application Publication WO 2006/106326.

A method of preparing a composition comprising a chemical compound that inhibits tumor cells from undergoing an epithelial to mesenchymal transition, comprising providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors, determining whether an agent that inhibits PAK2 kinase also inhibits tumor cells from undergoing an epithelial to mesenchymal transition, by contacting a sample of tumor cells with said agent, comparing in said sample of tumor cells induced to undergo EMT, the level of a biomarker whose level is indicative of the EMT status of the tumor cells to the level of the same biomarker in an identical sample of tumor cells induced to undergo EMT but not contacted with the agent that inhibits PAK2 kinase, and thus identifying the agent that inhibits PAK2 kinase as an agent that inhibits tumor cells from undergoing an epithelial to mesenchymal transition, and admixing the test agent so identified with a carrier, thereby preparing said composition. In one embodiment of this method the test agent is a small organic molecule. In another embodiment of this method, the epithelial to mesenchymal transition involves transcriptional repression by the protein Snail.

The present invention also provides a method of identifying an agent that impairs tumor cell mobility, and thus inhibits tumorigenicity, comprising providing a preparation containing a PAK2 kinase, incubating the preparation with a test agent to be screened under conditions to permit binding of the test agent to the kinase; determining whether the test agent inhibits the PAK2 kinase by detecting a decrease in the phosphotransferase activity of the kinase, thus identifying agents that are PAK2 kinase inhibitors, determining whether an agent that inhibits PAK2 kinase also inhibits tumor cell migration, by contacting a sample of tumor cells with said agent, comparing the extent of migration in said sample of tumor cells induced to migrate to the extent of migration in an identical sample of cells induced to migrate but not contacted with the agent that inhibits PAK2 kinase, and thus identifying the agent that inhibits PAK2 kinase as an agent that impairs tumor cell mobility. In one embodiment of this method the test agent is a small organic molecule. In another embodiment the tumor cells are induced to migrate using the protein TGF-beta. Other agants stimulating migration that may be used include, for example, HGF, MSP, EGF and other EGF-family ligands such as amphiregulin and HB-EGF, canonical Wnt ligands, non-canonical Wnt ligand Wnt5a, IL-1 alpha, IL-1beta, TNF-alpha, oncostatin M, Hedgehog-family ligands.

Many biomarkers are known whose level of expression or activity is indicative of the EMT status of tumor cells (e.g. see US Patent Application Publication 2007/0212738; U.S. Patent Application 60/923,463; U.S. Patent Application 60/997,514). Such markers tend to be classified as epithelial or mesenchymal, due to their characteristic association with the particular stage of EMT. Characteristic biomarkers can be, for example, proteins, encoding mRNAs, activity of a gene promoter, level of a transcriptional repressor, or promoter methylation. In any of the methods described herein the biomarker whose expression level is indicative of the EMT status of the sample tumor cells may be an epithelial cell biomarker. Epithelial cell biomarkers include for example E-cadherin, cytokeratin 8, cytokeratin 18, P-cadherin or erbB3. Additional epithelial cell biomarkers include Brk, γ-catenin, α1-catenin, α2-catenin, α3-catenin, connexin 31, plakophilin 3, stratifin 1, laminin alpha-5, and ST14. In any of the methods described herein the biomarker whose expression level is indicative of the EMT status of the sample tumor cells may also be certain mesenchymal cell biomarkers whose level is inhibited by PAK2 kinase inhibition, including for example the transcriptional repressors Snail (NCBI GeneID 6615), Zeb1 (NCBI GeneID 6935), Twist (NCBI GeneID 7291), Sip1 NCBI GeneID 8487), and Slug (NCBI GeneID 6591). Additionally, any other epithelial cell biomarkers known in that art (e.g. see US Patent Application Publication 2007/0212738; U.S. Patent Application 60/923,463; U.S. Patent Application 60/997,514), described herein, or yet to be described, may be used in the methods of the invention described herein. In any of the methods described herein, multiple biomarker level determinations can also be used to assess EMT status, potentially providing a more reliable assessment. For example, an epithelial and a mesenchymal biomarker level may be assessed, the reciprocal changes in each providing internal confirmation that EMT has occurred (e.g. suitable biomarker pairs include E-cadherin/Snail; ErbB3/Snail: E-cadherin/Zeb1.

In an alternative embodiment of any of the methods described herein that include a step of determining the level of a biomarker whose level is indicative of the EMT status of the sample tumor cells, the biomarker can be the activity of a gene promoter that is altered when the tumor cells undergo EMT. Such promoter activity is readily assessed by incorporating a promoter-reporter construct into the tumor cells and measuring reporter activity. In one embodiment, the activity of an epithelial biomarker gene promoter is assessed by inclusion of an epithelial biomarker gene promoter-reporter gene construct into the tumor cells such that said promoter reporter activity can be monitored by reporter gene expression level or activity. For example, the epithelial biomarker gene promoter-reporter gene construct may be an E-cadherin promoter-firefly luciferase construct. In an alternative embodiment, the activity of a mesenchymal biomarker gene promoter, for certain mesenchymal biomarkers whose level is inhibited by PAK2 kinase inhibition (e.g. Snail, Zeb1; see above), is assessed by inclusion of a mesenchymal biomarker gene promoter-reporter gene construct into the tumor cells such that said promoter reporter activity can be monitored by reporter gene expression level or activity. For example, the mesenchymal biomarker gene promoter-reporter gene construct may be a Snail promoter-firefly luciferase construct. The promoter-reporter gene construct may be permantly incorporated into the tumor cells as a stable engineered cell line, or may be transiently expressed, using any of the standard techniques for transferring nucleic acid constructs into cells (e.g. transfection, electroporation). Multiple promoter-reporter gene constructs may also be employed in order to monitor several biomarkers simultaneously, e.g. an E-cadherin promoter-firefly luciferase construct and a Snail promoter-Renilla luciferase construct, in order to, for example, monitor simultaneous repression of the E-cadherin gene and induction of the Snail gene as tumor cells undergo EMT, and the reversal of these steps by inhibition of PAK2 kinase. By using two different reporter genes that can be independently monitored (e.g. two luciferases that produce products that take part in luminescent reactions involving the emission of light of different characteristic wavelengths; e.g. see Hawkins, E. H. et al. (2002) Dual-Glo™ Luciferase Assay System: Convenient dual-reporter measurements in 96- and 384-well plates. *Promega Notes* 81, 22-6; Nieuwenhuijsen B W. et al. (2004) J Biomol Screen. 8, 676-84), both promoters can be monitored simultaneously.

In any of the methods or cell preparations described herein involving a biomarker gene promoter-reporter gene construct in the tumor cells for monitoring biomarker promoter activity by assessing reporter gene expression level, the reporter gene can be, any heterologous gene that expresses a protein whose level is readily determined by measuring expressed protein or enzymic activity. Suitable reporter genes include firefly (*Photinus pyralis*) luciferase, Renilla (*Renilla reniformis*) luciferase, Gaussia (*Gaussia princeps*) luciferase, Green fluorescent proteins (GFPs) and derivatives, and Red Fluoresecnt protein (RFPs) and derivatives, etc. (e.g. see Hawkins, E. H. et al. (2002) Dual-Glo™ Luciferase Assay System: Convenient dual-reporter measurements in 96- and 384-well plates. *Promega Notes* 81, 22-6; Nieuwenhuijsen B W. et al. (2004) J. Biomol. Screen. 8, 676-84; Verhaegen M. and Christopoulos T. K. (2002) Anal. Chem., 74:4378-4385; Tannous, B. A., et al. (2005) Mol. Ther., 11:435-443; Hoffmann, R. M. (2004) Acta Histochemica 106(2):77-87); Hoffmann, R. M. (2008) Methods in Cell Biol. 85:485-495).

In the context of the methods of this invention, epithelial, or certain mesenchymal biomarkers (see above for suitable mesenchymal biomarkers), expressed by a tumor cell can include molecular and cellular markers that indicate the transition state of the tumor cell. In a preferred embodiment the biomarker is an individual marker protein, or its encoding mRNA, characteristic of the particular transition state of the tumor cell, i.e. a tumor cell exhibiting epithelial or mesenchymal characteristics. In an alternative embodiment, in certain circumstances the biomarker may be a characteristic morphological pattern produced in the tumor cell by cellular macromolecules that is characteristic of either an epithelial or mesenchymal condition. Thus, morphometric cell analysis can be used to provide information on epithelial or mesenchymal status of tumor cells. In an additional embodiment the biomarker that indicates the transition state of the tumor cell is methylation of the E-Cadherin gene (CDH1) promoter. CDH1 promoter methylation indicates that tumor cells have undergone an EMT transition.

TABLE 1

Molecular Epithelial Biomarker Gene Identification

| Human Biomarker | NCBI GeneID[1] | NCBI RefSeq[2] |
|---|---|---|
| E-cadherin | 999 | NP_004351 |
| Brk | 5753 | NP_005966 |
| γ-catenin | 3728 | NP_002221 |
| α1-catenin | 1495 | NP_001894 |
| α2-catenin | 1496 | NP_004380 |
| α3-catenin | 29119 | NP_037398 |
| keratin 8 | 3856 | NP_002264 |
| keratin 18 | 3875 | NP_000215 |
| GPR54 | 84634 | NP_115940 |
| KISS1 | 3814 | NP_002247 |

[1] The NCBI GeneID number is a unique identifier of the biomarker gene from the NCBI Entrez Gene database record (National Center for Biotechnology Information (NCBI), U.S. National Library of Medicine, 8600 Rockville Pike, Building 38A, Bethesda, MD 20894; Internet address http://www.ncbi.nlm.nih.gov/).
[2] The NCBI RefSeq (Reference Sequence) is an example of a sequence expressed by the biomarker gene.

Table 1 lists genes coding for examples of epithelial biomarkers that can be used in the practice of the methods of the invention described herein. The epithelial biomarkers can include any product expressed by these genes, including variants thereof, e.g. expressed mRNA or protein, splice variants, co- and post-translationally modified proteins, polymorphic variants etc.

In another embodiment of the methods of this invention the mesenchymal biomarker is methylation of the promoter of a gene whose transcription is repressed as a result of EMT in the tumor cell. In the context of this method high levels of a tumor cell mesenchymal biomarker essentially means readily detectable methylation of the promoter (e.g. a strong signal during detection of a methylation-specific PCR-amplified nucleic acid product derived from a promoter methylation site), whereas low levels of a tumor cell mesenchymal biomarker essentially means no detectable or low methylation of the promoter (e.g. no, or a comparatively weak, signal during detection of a methylation-specific PCR-amplified nucleic acid product derived from a promoter methylation site). In one embodiment of this method the gene whose transcription is repressed as a result of EMT in the tumor cell is the E-Cadherin gene (i.e.CDH1; NCBI GeneID 999). In another embodiment of this method the gene whose transcription is repressed as a result of EMT in the tumor cell is the γ-catenin gene (i.e. NCBI GeneID 3728). In another embodiment of this method the gene whose transcription is repressed as a result of EMT in the tumor cell is an α-catenin gene (e.g. NCBI GeneID 1495, 1496, or 29119). In another embodiment of this method the gene whose transcription is repressed as a result of EMT in the tumor cell is a cytokeratin gene (e.g. NCBI GeneID 3856 (keratin 8) or 3875 (keratin 18)).

Examples of additional epithelial markers that can be used in any of the methods of this invention include phospho-14-3-3 epsilon, 14-3-3 gamma (KCIP-1), 14-3-3 sigma (Stratifin), 14-3-3 zeta/delta,phospho-serine/threonine phosphatase 2A, 4F2hc(CD98 antigen), adenine nucleotide translocator 2, annexin A3, ATP synthase beta chain, phospho-insulin receptor substrate p53/p54, Basigin (CD 147 antigen), phospho-CRK-associated substrate (p130Cas), Bcl-X, phospho-P-cadherin, phospho-calmodulin (CaM), Calpain-2 catalytic subunit, Cathepsin D, Cofilin-1, Calpain small subunit 1, Catenin beta-1, Catenin delta-1 (p120 catenin), Cystatin B, phospho-DAZ-associated protein 1, Carbonyl reductase [NADPH], Diaphanous-related formin 1 (DRF1), Desmoglein-2, Elongation factor 1-delta, phospho-p185erbB2, Ezrin (p81), phospho-focal adhesion kinase 1, phospho-p94-FER (c-FER)., Filamin B, phospho-GRB2-associated binding protein 1, Rho-GDI alpha, phospho-GRB2, GRP 78, Glutathione S-transferase P, 3-hydroxyacyl-CoA dehydrogenase, HSP 90-alpha, HSP70.1, eIF3 p110, eIF-4E, Leukocyte elastase inhibitor, Importin-4, Integrin alpha-6, Integrin beta-4, phospho-Cytokeratin 17, Cytokeratin 19, Cytokeratin 7, Casein kinase I, alpha, Protein kinase C, delta, Pyruvate kinase, isozymes M1/M2,phospho-Erbin, LIM and SH3 domain protein 1 (LASP-1), 4F21c (CD98 light chain), L-lactate dehydrogenase A chain, Galectin-3, Galectin-3 binding protein, phospho-LIN-7 homolog C, MAP (APC-binding protein EB1), Maspin precursor (Protease inhibitor 5), phospho-Met tyrosine kinase (HGF receptor), Mixed-lineage leukemia protein 2, Monocarboxylate transporter 4, phospho-C-Myc binding protein (AMY-1), Myosin-9, Myosin light polypeptide 6, Nicotinamide phosphoribosyltransferase, Niban-like protein (Meg-3), Ornithine aminotransferase, phospho-Occludin, Ubiquitin thiolesterase, PAF acetylhydrolase IB beta subunit, phospho-partitioning-defective 3 (PAR-3), phospho-programmed cell death 6-interacting protein, phospho-Programmed cell death protein 6, Protein disulfide-isomerase, phospho-plakophilin-2, phospho-plakophilin-3, Protein phosphatase 1, Peroxiredoxin 5, Proteasome activator complex subunit 1, Prothymosin alpha, Retinoic acid-induced protein 3, phospho-DNA repair protein REV1, Ribonuclease inhibitor, RuvB-like 1, S-100P, S-100L, Calcyclin, S100C, phospho-Sec23A, phospho-Sec23B, *Lysosome* membrane protein II (LIMP II), p60-Src, phospho-Amplaxin (EMS1), SLP-2, Gamma-synuclein, Tumor calcium signal transducer 1, Tumor calcium signal transducer 2, Transgelin-2, Transaldolase, Tubulin beta-2 chain, Translationally controlled (TCTP), Tissue transglutaminase, Transmembrane protein Tmp21, Ubiquitin-conjugating enzyme E2 N, UDP-glucosyltransferase 1, phospho-p61-Yes, phospho-Tight junction protein ZO-1, AHNAK (Desmoyokin), phospho-ATP synthase beta chain, phospho-ATP synthase delta, Cold shock domain protein E1, Desmoplakin III, Plectin 1, phospho-Nectin 2 (CD112 antigen), phospho-p185-Ron, phospho-SHC1, E-cadherin, Brk, γ-catenin, α1-catenin, α2-catenin, α3-catenin, keratin 8, keratin 18, connexin 31, plakophilin 3, stratafin 1, laminin alpha-5 and ST14, and other epithelial biomarkers known in the art (see for example, US Patent Application Publication 2007/0212738; U.S. Patent Application 60/923,463; U.S. Patent Application 60/997,514). Where the epithelial biomarker is a phospho-"protein" the extent of phosphorylation of the protein rather than the level of the protein per se is the parameter that is altered after EMT. The altered level of phosphorylation of these proteins is also understood to be due to changes in the level of phosphorylation of one or more tyrosine residues of the protein protein (US Patent Application Publication 2007/0212738). Substrates of PAK1 and/or PAK2 kinases that have been implicated in EMT may also be used as biomarkers (Kumar, R. et al. (2006) Nature Reviews Cancer 6, 459-471).

The biomarkers in the above list of epithelial biomarkers have been identified as being altered in expression level (or phosphorylation level for phospho-"proteins") after EMT (see for example, US Patent Application Publication 2007/0212738, the contents of which are incorporated herein by reference; US Published Application 2006/0211060 (filed Mar. 16, 2006); Thomson, S. et al. (2005) Cancer Res. 65(20) 9455-9462; and Yauch, R. L. et al. (2005) Clin. Can. Res. 11(24) 8686-8698).

In the methods of this invention, biomarker expression level can be assessed relative to a control molecule whose expression level remains constant throughout EMT, or when comparing tumor cells expressing either epithelial or mesenchymal transition states as indicated by molecular biomarkers (e.g. a "housekeeping" gene, such as GAPDH, β-actin, tubulin, or the like). Biomarker expression level can also be assessed relative to the other type of tumor cell biomarker (i.e. epithelial compared to mesenchymal), or to the biomarker level in non-tumor cells of the same tissue, or another cell or tissue source used as an assay reference.

In the methods of this invention, the level of an epithelial or mesenchymal biomarker expressed by a tumor cell can be assessed by using any of the standard bioassay procedures known in the art for determination of the level of expression of a gene, including for example ELISA, RIA, immunopreciptation, immunoblotting, immunofluorescence microscopy, immunohistochemistry (IHC), RT-PCR, in situ hybridization, cDNA microarray, or the like, as described in more detail below. In an embodiment of any of these methods, their use is coupled with a method to isolate a particular cell population, e.g. laser capture microdissection (LCM). In an additional embodiment, FACS analysis can be used with immunofluorescence biomarker (e.g. E-cadherin) labeling to isolate and quantify cell populations expressing different epithelial or mesenchymal biomarkers, and thus for example the percentage of cells that have undergone an EMT can be estimated (e.g. see Xu, Z. et al. (2003) Cell Research 13(5):343-350).

In the methods of this invention, the expression level of a tumor cell epithelial or mesenchymal biomarker in vivo is preferably assessed by assaying a tumor biopsy. In one embodiment the biopsy comprises samples taken from multiple areas of the tumor, or a method (e.g. core needle biopsy) that samples different areas of the tumor, thus ensuring that when the tumor is of a heterogeneous nature with respect to the types of cells it contains, that a representative biopsy is obtained. In an alternative embodiment, given that a tumor may be heterogeneous with respect to the EMT status of the cells it contains, the methods of this invention are preferably applied separately to different cell types (e.g. using IHC, or an analysis method coupled with a step to isolate a particular cell population). Alternatively, by employing cell surface epithelial and/or mesenchymal biomarker antibodies (e.g. to E-cadherin), FACS analysis can be used to isolate and quantify the numbers of tumor cells at different stages of EMT.

However, in an alternative embodiment, expression level of the tumor cell biomarker can be assessed in bodily fluids or excretions containing detectable levels of biomarkers originating from the tumor or tumor cells. Bodily fluids or excretions useful in the present invention include blood, urine, saliva, stool, pleural fluid, lymphatic fluid, sputum, ascites, prostatic fluid, cerebrospinal fluid (CSF), or any other bodily secretion or derivative thereof. By blood it is meant to include whole blood, plasma, serum or any derivative of blood. Assessment of tumor epithelial or mesenchymal biomarkers in such bodily fluids or excretions can sometimes be preferred in circumstances where an invasive sampling method is inappropriate or inconvenient.

For assessment of tumor cell epithelial or mesenchymal biomarker expression, tumor samples containing tumor cells, or proteins or nucleic acids produced by these tumor cells, may be used in the methods of the present invention. In these embodiments, the level of expression of the biomarker can be assessed by assessing the amount (e.g. absolute amount or concentration) of the marker in a tumor cell sample, e.g., a tumor biopsy obtained from an animal, or another sample containing material derived from the tumor (e.g. blood, serum, urine, or other bodily fluids or excretions as described herein above). The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, tumor biopsies may also be subjected to post-collection preparative and storage techniques, e.g. fixation.

Determination of epithelial or mesenchymal biomarker levels in in vivo studies can be assessed by a number of different approaches, including direct analysis of proteins that segregate as epithelial related (e.g. E-cadherin) or mesenchymal related (e.g. Zeb1) biomarkers. An advantage of this approach is that EMT markers are read directly, and the relative amounts of cell populations expressing epithelial or mesenchymal biomarkers can readily be examined and quantified, by for example FACS analysis (e.g. see Xu, Z. et al. (2003) Cell Research 13(5):343-350). However, this approach also requires sufficient quantities of cells or tissue in order to perform an analysis (e.g. immunohistochemistry). Sufficient quantities of tissue may be difficult to obtain from certain procedures such as FNA (fine needle aspiration). Core biopsies provide larger amounts of tissue, but are sometimes not readily available. Alternatively, these EMT biomarkers could be evaluated based upon the expression level of their encoding RNA transcripts using a quantitative PCR based approach. An advantage of this approach is that very few tumor cells are required for this measurement, and it is very likely that sufficient material may be obtained via an FNA. However, here the transcript levels for a given biomarker may be derived from both tumor cells as well as infiltrating stromal cells from the tumor. Given that stromal cells also express mesenchymal cell markers, this may obscure detection of the EMT status for tumor cells. Use of in situ hybridization (e.g. FISH) or tissue microdisection may be useful here to overcome this potential limitation.

Given that the expression level of E-cadherin is a hallmark of the EMT status for a tumor cell, EMT may also be evaluated based upon the methylation status of the E-cadherin promoter, as described herein. Methylation silences transcription, and so a high level of methylation correlates with a mesenchymal-like state. A potential benefit of this approach is that, like measurement of transcript levels, measuring the methylation status of DNA would likely require very little material. Sufficient material could likely be obtained from an FNA and would not require a core biopsy. Additionally, since this approach involves evaluation of DNA and not RNA, it is likely to be a more stable read-out over time, such as during medium or long term storage of a sample.

In the methods of the invention, one can detect expression of biomarker proteins having at least one portion which is displayed on the surface of tumor cells which express it. It is a simple matter for the skilled artisan to determine whether a marker protein, or a portion thereof, is exposed on the cell surface. For example, immunological methods may be used to detect such proteins on whole cells, or well known computer-based sequence analysis methods may be used to predict the presence of at least one extracellular domain (i.e. including both secreted proteins and proteins having at least one cell-surface domain). Expression of a marker protein having at least one portion which is displayed on the surface of a cell which expresses it may be detected without necessarily lysing the tumor cell (e.g. using a labeled antibody which binds specifically with a cell-surface domain of the protein).

Expression of a biomarkers described in this invention may be assessed by any of a wide variety of well known methods for detecting expression of a transcribed nucleic acid or protein. Non-limiting examples of such methods include immunological methods for detection of secreted, cell-surface, cytoplasmic, or nuclear proteins, protein purification methods, protein function or activity assays, nucleic acid hybridization methods, nucleic acid reverse transcription methods, and nucleic acid amplification methods.

In one embodiment, expression of a biomarker is assessed using an antibody (e.g. a radio-labeled, chromophore-labeled, fluorophore-labeled, or enzyme-labeled antibody), an antibody derivative (e.g. an antibody conjugated with a substrate or with the protein or ligand of a protein-ligand pair {e.g. biotin-streptavidin}), or an antibody fragment (e.g. a single-chain antibody, an isolated antibody hypervariable domain, etc.) which binds specifically with a biomarker protein or fragment thereof, including a biomarker protein which has undergone either all or a portion of post-translational modifications to which it is normally subjected in the tumor cell (e.g. glycosylation, phosphorylation, methylation etc.).

In another embodiment, expression of a biomarker is assessed by preparing mRNA/cDNA (i.e. a transcribed polynucleotide) from tumor cells, and by hybridizing the mRNA/cDNA with a reference polynucleotide which is a complement of a biomarker nucleic acid, or a fragment thereof. cDNA can, optionally, be amplified using any of a variety of polymerase chain reaction methods prior to hybridization with the reference polynucleotide. Expression of one or more biomarkers can likewise be detected using quantitative PCR to assess the level of expression of the biomarker(s). Alternatively, any of the many known methods of detecting mutations or variants (e.g. single nucleotide polymorphisms, deletions, etc.) of a biomarker of the invention may be used to detect occurrence of a biomarker in tumor cells.

In a related embodiment, a mixture of transcribed polynucleotides obtained from the sample is contacted with a substrate having fixed thereto a polynucleotide complementary to or homologous with at least a portion (e.g. at least 7, 10, 15, 20, 25, 30, 40, 50, 100, 500, or more nucleotide residues) of a biomarker nucleic acid. If polynucleotides complementary to or homologous with are differentially detectable on the substrate (e.g. detectable using different chromophores or fluorophores, or fixed to different selected positions), then the levels of expression of a plurality of biomarkers can be assessed simultaneously using a single substrate (e.g. a "gene chip" microarray of polynucleotides fixed at selected positions). When a method of assessing biomarker expression is used which involves hybridization of one nucleic acid with another, it is preferred that the hybridization be performed under stringent hybridization conditions.

When a plurality of biomarkers of the invention are used in the methods of the invention, the level of expression of each biomarker in tumor cells can be compared with the normal level of expression of each of the plurality of biomarkers in non-cancerous cells of the same type, either in a single reaction mixture (i.e. using reagents, such as different fluorescent probes, for each biomarker) or in individual reaction mixtures corresponding to one or more of the biomarkers.

The level of expression of a biomarker in normal (i.e. non-cancerous) human cells can be assessed in a variety of ways. In one embodiment, this normal level of expression is assessed by assessing the level of expression of the biomarker in cells which appears to be non-cancerous, and then comparing this normal level of expression with the level of expression in the tumor cells.

An exemplary method for detecting the presence or absence of a biomarker protein or nucleic acid in a biological sample (e.g. tumor cells) involves obtaining a biological sample and contacting the biological sample with a compound or an agent capable of detecting the polypeptide or nucleic acid (e.g., mRNA, genomic DNA, or cDNA). The detection methods of the invention can thus be used to detect mRNA, protein, cDNA, or genomic DNA, for example, in a biological sample in vitro as well as in vivo. For example, in vitro techniques for detection of mRNA include Northern hybridizations and in situ hybridizations. In vitro techniques for detection of a biomarker protein include enzyme linked immunosorbent assays (ELISAs), Western blots, immunoprecipitations and immunofluorescence. In vitro techniques for detection of genomic DNA include Southern hybridizations. In vivo techniques for detection of mRNA include polymerase chain reaction (PCR), Northern hybridizations and in situ hybridizations. Furthermore, in vivo techniques for detection of a biomarker protein include introducing into a subject a labeled antibody directed against the protein or fragment thereof. For example, the antibody can be labeled with a radioactive marker whose presence and location in a subject can be detected by standard imaging techniques.

A general principle of such diagnostic and prognostic assays involves preparing a sample or reaction mixture that may contain a biomarker, and a probe, under appropriate conditions and for a time sufficient to allow the biomarker and probe to interact and bind, thus forming a complex that can be removed and/or detected in the reaction mixture. These assays can be conducted in a variety of ways.

For example, one method to conduct such an assay would involve anchoring the biomarker or probe onto a solid phase support, also referred to as a substrate, and detecting target biomarker/probe complexes anchored on the solid phase at the end of the reaction. In one embodiment of such a method, a sample from a subject, which is to be assayed for presence and/or concentration of biomarker, can be anchored onto a carrier or solid phase support. In another embodiment, the reverse situation is possible, in which the probe can be anchored to a solid phase and a sample from a subject can be allowed to react as an unanchored component of the assay.

There are many established methods for anchoring assay components to a solid phase. These include, without limitation, biomarker or probe molecules which are immobilized through conjugation of biotin and streptavidin. Such biotinylated assay components can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). In certain embodiments, the surfaces with immobilized assay components can be prepared in advance and stored.

Other suitable carriers or solid phase supports for such assays include any material capable of binding the class of molecule to which the biomarker or probe belongs. Well-known supports or carriers include, but are not limited to, glass, polystyrene, nylon, polypropylene, nylon, polyethylene, dextran, amylases, natural and modified celluloses, polyacrylamides, gabbros, and magnetite.

In order to conduct assays with the above mentioned approaches, the non-immobilized component is added to the solid phase upon which the second component is anchored. After the reaction is complete, uncomplexed components may be removed (e.g., by washing) under conditions such that any complexes formed will remain immobilized upon the solid-phase. The detection of biomarker/probe complexes anchored to the solid phase can be accomplished in a number of methods outlined herein.

In one embodiment, the probe, when it is the unanchored assay component, can be labeled for the purpose of detection and readout of the assay, either directly or indirectly, with detectable labels discussed herein and which are well-known to one skilled in the art.

It is also possible to directly detect biomarker/probe complex formation without further manipulation or labeling of either component (biomarker or probe), for example by utilizing the technique of fluorescence energy transfer (i.e. FET, see for example, Lakowicz et al., U.S. Pat. No. 5,631,169; Stavrianopoulos, et al., U.S. Pat. No. 4,868,103). A fluorophore label on the first, 'donor' molecule is selected such that, upon excitation with incident light of appropriate wavelength, its emitted fluorescent energy will be absorbed by a fluorescent label on a second 'acceptor' molecule, which in turn is able to fluoresce due to the absorbed energy. Alternately, the 'donor' protein molecule may simply utilize the natural fluorescent energy of tryptophan residues. Labels are chosen that emit different wavelengths of light, such that the 'acceptor' molecule label may be differentiated from that of the 'donor'. Since the efficiency of energy transfer between the labels is related to the distance separating the molecules, spatial relationships between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another embodiment, determination of the ability of a probe to recognize a biomarker can be accomplished without labeling either assay component (probe or biomarker) by utilizing a technology such as real-time Biomolecular Interaction Analysis (BIA) (see, e.g., Sjolander, S, and Urbanic-zky, C., 1991, Anal. Chem. 63:2338-2345 and Szabo et al., 1995, Curr. Opin. Struct. Biol. 5:699-705). As used herein, "BIA" or "surface plasmon resonance" is a technology for studying biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal which can be used as an indication of real-time reactions between biological molecules.

Alternatively, in another embodiment, analogous diagnostic and prognostic assays can be conducted with biomarker and probe as solutes in a liquid phase. In such an assay, the complexed biomarker and probe are separated from uncomplexed components by any of a number of standard techniques, including but not limited to: differential centrifugation, chromatography, electrophoresis and immunoprecipitation. In differential centrifugation, biomarker/probe complexes may be separated from uncomplexed assay components through a series of centrifugal steps, due to the different sedimentation equilibria of complexes based on their different sizes and densities (see, for example, Rivas, G., and Minton, A. P., 1993, Trends Biochem Sci. 18(8):284-7). Standard chromatographic techniques may also be utilized to separate complexed molecules from uncomplexed ones. For example, gel filtration chromatography separates molecules based on size, and through the utilization of an appropriate gel filtration resin in a column format, for example, the relatively larger complex may be separated from the relatively smaller uncomplexed components. Similarly, the relatively different charge properties of the biomarker/probe complex as compared to the uncomplexed components may be exploited to differentiate the complex from uncomplexed components, for example through the utilization of ion-exchange chromatography resins. Such resins and chromatographic techniques are well known to one skilled in the art (see, e.g., Heegaard, N.H., 1998, J. Mol. Recognit. Winter 11(1-6):141-8; Hage, D. S., and Tweed, S. A. J. Chromatogr B Biomed Sci Appl 1997 Oct. 10; 699(1-2):499-525). Gel electrophoresis may also be employed to separate complexed assay components from unbound components (see, e.g., Ausubel et al., ed., Current Protocols in Molecular Biology, John Wiley & Sons, New York, 1987-1999). In this technique, protein or nucleic acid complexes are separated based on size or charge, for example. In order to maintain the binding interaction during the electrophoretic process, non-denaturing gel matrix materials and conditions in the absence of reducing agent are typically preferred. Appropriate conditions to the particular assay and components thereof will be well known to one skilled in the art.

In a particular embodiment, the level of biomarker mRNA can be determined both by in situ and by in vitro formats in a biological sample using methods known in the art. The term "biological sample" is intended to include tissues, cells, biological fluids and isolates thereof, isolated from a subject, as well as tissues, cells and fluids present within a subject. Many expression detection methods use isolated RNA. For in vitro methods, any RNA isolation technique that does not select against the isolation of mRNA can be utilized for the purification of RNA from tumor cells (see, e.g., Ausubel et al., ed., Current Protocols in Molecular Biology, John Wiley & Sons, New York 1987-1999). Additionally, large numbers of tissue samples can readily be processed using techniques well known to those of skill in the art, such as, for example, the single-step RNA isolation process of Chomczynski (1989, U.S. Pat. No. 4,843,155).

The isolated mRNA can be used in hybridization or amplification assays that include, but are not limited to, Southern- or Northern analyses, polymerase chain reaction analyses and probe arrays. One preferred diagnostic method for the detection of mRNA levels involves contacting the isolated mRNA with a nucleic acid molecule (probe) that can hybridize to the mRNA encoded by the gene being detected. The nucleic acid probe can be, for example, a full-length cDNA, or a portion thereof, such as an oligonucleotide of at least 7, 15, 30, 50, 100, 250 or 500 nucleotides in length and sufficient to specifically hybridize under stringent conditions to a mRNA or genomic DNA encoding a biomarker of the present invention. Other suitable probes for use in the diagnostic assays of the invention are described herein. Hybridization of an mRNA with the probe indicates that the biomarker in question is being expressed.

In one format, the mRNA is immobilized on a solid surface and contacted with a probe, for example by running the isolated mRNA on an agarose gel and transferring the mRNA from the gel to a membrane, such as nitrocellulose. In an alternative format, the probe(s) are immobilized on a solid surface and the mRNA is contacted with the probe(s), for example, in an Affymetrix gene chip array. A skilled artisan can readily adapt known mRNA detection methods for use in detecting the level of mRNA encoded by the biomarkers of the present invention.

An alternative method for determining the level of mRNA biomarker in a sample involves the process of nucleic acid amplification, e.g., by RT-PCR (the experimental embodiment set forth in Mullis, 1987, U.S. Pat. No. 4,683,202), ligase chain reaction (Barany, 1991, Proc. Natl. Acad. Sci. USA, 88:189-193), self sustained sequence replication (Guatelli et al., 1990, Proc. Natl. Acad. Sci. USA 87:1874-1878), transcriptional amplification system (Kwoh et al., 1989, Proc. Natl. Acad. Sci. USA 86:1173-1177), Q-Beta Replicase (Lizardi et al., 198.8, Bio/Technology 6:1197), rolling circle replication (Lizardi et al., U.S. Pat. No. 5,854,033) or any other nucleic acid amplification method, followed by the detection of the amplified molecules using techniques well known to those of skill in the art. These detection schemries are especially useful for the detection of nucleic acid molecules if such molecules are present in very low numbers. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and flank a region from about 50 to 200 nucleotides in length. Under appropriate conditions and with appropriate reagents, such primers permit the amplification of a nucleic acid molecule comprising the nucleotide sequence flanked by the primers.

For in situ methods, mRNA does not need to be isolated from the tumor cells prior to detection. In such methods, a cell or tissue sample is prepared/processed using known histological methods. The sample is then immobilized on a support, typically a glass slide, and then contacted with a probe that can hybridize to mRNA that encodes the biomarker.

As an alternative to making determinations based on the absolute expression level of the biomarker, determinations may be based on the normalized expression level of the biomarker. Expression levels are normalized by correcting the absolute expression level of a biomarker by comparing its expression to the expression of a gene that is not a biomarker, e.g., a housekeeping gene that is constitutively expressed. Suitable genes for normalization include housekeeping genes such as the actin gene, or epithelial cell-specific genes. This normalization allows the comparison of the expression level in one sample, e.g., a tumor cell sample, to another sample, e.g., a non-tumor sample, or between samples from different sources, or between samples before and after inductuion of EMT.

Alternatively, the expression level can be provided as a relative expression level. To determine a relative expression level of a biomarker (e.g. a mesenchymal biomarker), the level of expression of the biomarker is determined for 10 or more samples of normal versus cancer cell isolates, preferably 50 or more samples, prior to the determination of the expression level for the sample in question. The mean expression level of each of the genes assayed in the larger number of samples is determined and this is used as a baseline expression level for the biomarker. The expression level of the biomarker determined for the test sample (absolute level of expression) is then divided by the mean expression value obtained for that biomarker. This provides a relative expression level.

In another embodiment of the present invention, a biomarker protein is detected. A preferred agent for detecting biomarker protein of the invention is an antibody capable of binding to such a protein or a fragment thereof, preferably an antibody with a detectable label. Antibodies can be polyclonal, or more preferably, monoclonal. An intact antibody, or a fragment or derivative thereof (e.g., Fab or F(ab').sub.2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin.

Proteins from tumor cells can be isolated using techniques that are well known to those of skill in the art. The protein isolation methods employed can, for example, be such as those described in Harlow and Lane (Harlow and Lane, 1988, Antibodies: A Laboratory Manual, Cold Spring Harbor Laboratory Press, Cold Spring Harbor, N.Y.).

A variety of formats can be employed to determine whether a sample contains a protein that binds to a given antibody. Examples of such formats include, but are not limited to, enzyme immunoassay (EIA), radioimmunoassay (RIA), Western blot analysis and enzyme linked immunoabsorbant assay (ELISA). A skilled artisan can readily adapt known protein/antibody detection methods for use in determining whether tumor cells express a biomarker of the present invention.

In one format, antibodies, or antibody fragments or derivatives, can be used in methods such as Western blots or immunofluorescence techniques to detect the expressed proteins. In such uses, it is generally preferable to immobilize either the antibody or proteins on a solid support. Suitable solid phase supports or carriers include any support capable of binding an antigen or an antibody. Well-known supports or carriers include glass, polystyrene, polypropylene, polyethylene, dextran, nylon, amylases, natural and modified celluloses, polyacrylamides, gabbros, and magnetite.

One skilled in the art will know many other suitable carriers for binding antibody or antigen, and will be able to adapt such support for use with the present invention. For example, protein isolated from tumor cells can be run on a polyacrylamide gel electrophoresis and immobilized onto a solid phase support such as nitrocellulose. The support can then be washed with suitable buffers followed by treatment with the detectably labeled antibody. The solid phase support can then be washed with the buffer a second time to remove unbound antibody. The amount of bound label on the solid support can then be detected by conventional means.

For ELISA assays, specific binding pairs can be of the immune or non-immune type. Immune specific binding pairs are exemplified by antigen-antibody systems or hapten/anti-hapten systems. There can be mentioned fluorescein/anti-fluorescein, dinitrophenyl/anti-dinitrophenyl, biotin/anti-biotin, peptide/anti-peptide and the like. The antibody member of the specific binding pair can be produced by customary methods familiar to those skilled in the art. Such methods involve immunizing an animal with the antigen member of the specific binding pair. If the antigen member of the specific binding pair is not immunogenic, e.g., a hapten, it can be covalently coupled to a carrier protein to render it immunogenic. Non-immune binding pairs include systems wherein the two components share a natural affinity for each other but are not antibodies. Exemplary non-immune pairs are biotin-streptavidin, intrinsic factor-vitamin $B_{12}$, folic acid-folate binding protein and the like.

A variety of methods are available to covalently label antibodies with members of specific binding pairs. Methods are selected based upon the nature of the member of the specific binding pair, the type of linkage desired, and the tolerance of the antibody to various conjugation chemistries. Biotin can be covalently coupled to antibodies by utilizing commercially available active derivatives. Some of these are biotin-N-hydroxy-succinimide which binds to amine groups on proteins; biotin hydrazide which binds to carbohydrate moieties, aldehydes and carboxyl groups via a carbodiimide coupling; and biotin maleimide and iodoacetyl biotin which bind to sulfhydryl groups. Fluorescein can be coupled to protein amine groups using fluorescein isothiocyanate. Dinitrophenyl groups can be coupled to protein amine groups using 2,4-dinitrobenzene sulfate or 2,4-dinitrofluorobenzene. Other standard methods of conjugation can be employed to couple monoclonal antibodies to a member of a specific binding pair including dialdehyde, carbodiimide coupling, homofunctional crosslinking, and heterobifunctional crosslinking. Carbodiimide coupling is an effective method of coupling carboxyl groups on one substance to amine groups on another. Carbodiimide coupling is facilitated by using the commercially available reagent 1-ethyl-3-(dimethyl-aminopropyl)-carbodiimide (EDAC).

Homobifunctional crosslinkers, including the bifunctional imidoesters and bifunctional N-hydroxysuccinimide esters, are commercially available and are employed for coupling amine groups on one substance to amine groups on another. Heterobifunctional crosslinkers are reagents which possess different functional groups. The most common commercially available heterobifunctional crosslinkers have an amine reactive N-hydroxysuccinimide ester as one functional group, and a sulfhydryl reactive group as the second functional group. The most common sulfhydryl reactive groups are maleimides, pyridyl disulfides and active halogens. One of the functional groups can be a photoactive aryl nitrene, which upon irradiation reacts with a variety of groups.

The detectably-labeled antibody or detectably-labeled member of the specific binding pair is prepared by coupling to a reporter, which can be a radioactive isotope, enzyme, fluorogenic, chemiluminescent or electrochemical materials. Two commonly used radioactive isotopes are $^{125}I$ and $^{3}H$. Standard radioactive isotopic labeling procedures include the chloramine T, lactoperoxidase and Bolton-Hunter methods for $^{125}I$ and reductive methylation for $^{3}H$. The term "detectably-labeled" refers to a molecule labeled in such a way that it can be readily detected by the intrinsic enzymic activity of the label or by the binding to the label of another component, which can itself be readily detected.

Enzymes suitable for use in this invention include, but are not limited to, horseradish peroxidase, alkaline phosphatase, β-galactosidase, glucose oxidase, luciferases, including firefly, Renilla and Gaussia, β-lactamase, urease, green fluorescent protein (GFP) and lysozyme. Enzyme labeling is facilitated by using dialdehyde, carbodiimide coupling, homobifunctional crosslinkers and heterobifunctional crosslinkers as described above for coupling an antibody with a member of a specific binding pair.

The labeling method chosen depends on the functional groups available on the enzyme and the material to be labeled, and the tolerance of both to the conjugation conditions. The labeling method used in the present invention can be one of, but not limited to, any conventional methods currently employed including those described by Engvall and Pearlmann, Immunochemistry 8, 871 (1971), Avrameas and Ternynck, Immunochemistry 8, 1175 (1975), Ishikawa et al., J. Immunoassay 4(3):209-327 (1983) and Jablonski, Anal. Biochem. 148:199 (1985).

Labeling can be accomplished by indirect methods such as using spacers or other members of specific binding pairs. An example of this is the detection of a biotinylated antibody with unlabeled streptavidin and biotinylated enzyme, with streptavidin and biotinylated enzyme being added either sequentially or simultaneously. Thus, according to the present invention, the antibody used to detect can be detectably-labeled directly with a reporter or indirectly with a first member of a specific binding pair. When the antibody is coupled to a first member of a specific binding pair, then detection is effected by reacting the antibody-first member of a specific binding complex with the second member of the binding pair that is labeled or unlabeled as mentioned above.

Moreover, the unlabeled detector antibody can be detected by reacting the unlabeled antibody with a labeled antibody specific for the unlabeled antibody. In this instance "detectably-labeled" as used above is taken to mean containing an epitope by which an antibody specific for the unlabeled antibody can bind. Such an anti-antibody can be labeled directly or indirectly using any of the approaches discussed above. For example, the anti-antibody can be coupled to biotin which is detected by reacting with the streptavidin-horseradish peroxidase system discussed above.

In one embodiment of this invention biotin is utilized. The biotinylated antibody is in turn reacted with streptavidin-horseradish peroxidase complex. Orthophenylenediamine, 4-chloro-naphthol, tetramethylbenzidine (TMB), ABTS, BTS or ASA can be used to effect chromogenic detection.

In one immunoassay format for practicing this invention, a forward sandwich assay is used in which the capture reagent has been immobilized, using conventional techniques, on the surface of a support. Suitable supports used in assays include synthetic polymer supports, such as polypropylene, polystyrene, substituted polystyrene, e.g. aminated or carboxylated polystyrene, polyacrylamides, polyamides, polyvinylchloride, glass beads, agarose, or nitrocellulose.

Tumor cells in any of the methods described herein may be tumor cells from any of the following tumors or cancers: NSCL, breast, colon, or pancreatic cancer, lung cancer, bronchioloalveolar cell lung cancer, bone cancer, skin cancer, cancer of the head or neck, cutaneous or intraocular melanoma, uterine cancer, ovarian cancer, rectal cancer, cancer of the anal region, stomach cancer, gastric cancer, uterine cancer, carcinoma of the fallopian tubes, carcinoma of the endometrium, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the ureter, cancer of the kidney, renal cell carcinoma, carcinoma of the renal pelvis, mesothelioma, hepatocellular cancer, biliary cancer, chronic or acute leukemia, lymphocytic lymphomas, neoplasms of the central nervous system (CNS), spinal axis tumors, brain stem glioma, glioblastoma multiforme, astrocytomas, schwannomas, ependymomas, medulloblastomas, meningiomas, squamous cell carcinomas, pituitary adenomas, including refractory versions of any of the above cancers, or a combination of one or more of the above cancers. The tumor cells may be human tumor cells, or tumor cells from another animal (e.g. dog, cat, bovine, horse, pig, mouse, rat etc.).

The term "refractory" as used herein is used to define a cancer for which treatment (e.g. chemotherapy drugs, biological agents, and/or radiation therapy) has proven to be ineffective. A refractory cancer tumor may shrink, but not to the point where the treatment is determined to be effective. Typically however, the tumor stays the same size as it was before treatment (stable disease), or it grows (progressive disease).

In any of the methods of the invention described herein, determination of the phosphotransferase activity of PAK1 or PAK2, in for example, in vitro assays of purified enzyme, immune complexes containing the kinase, tumor cells in culture, or in tumor cells in vivo (e.g. tumor xenografts), can be assessed by any of the many methods known and currently used in the art, or by new methods yet to be invented.

The phosphotranferase activity of PAK1 or PAK2 may be determined when using in vitro assays of purified enzyme by a standard kinase assay, in which incorporation of $^{32}$P-phosphate into a peptide substrate from radio-labelled ATP is determined after adsorption onto phosphocellulose paper (e.g. see PAK2 assays in US Patent Application Publication US 2006/0004043 or US 2005/0009876). Alternatively, SPA assays may be used for determination of the incorporation of $^{32}$P phosphate into a biotinylated peptide substrate (e.g. see PAK1 and PAK2 kinase assays in International Patent Application Publication WO 2006/106326). In addition, in for example immune complex kinase assays of PAK1 or PAK2 kinase, using myelin basic protein as a substrate, SDS-PAGE electrophoresis and autoradiography be be used for determination of the incorporation of $^{32}$P-phosphate into the substrate (e.g. see Wilkes, M. C. et al. (2003) Mol. Cell. Biol. 23:8878-8889). Non-isotopic kinase assays may also be used, where phosphate incorporation into a peptide substrate is determined using an antibody specific for the phospho-peptide. For example, the phosphotranferase activity of PAK1 or PAK2 may be determined using a sandwich ELISA assay in which a first antibody reagent is specific to a PAK1 or PAK2 substrate peptide and a second antibody reagent is specific to one or more PAK1 or PAK2 phosphorylation sites on the substrate peptide. The first antibody reagent is typically adsorbed onto a surface (e.g. a plate or dish, e.g. a 96-well plate), phosphorylated PAK1 or PAK2 substrate peptide adsorbed onto the surface by contacting with the first antibody, and the phosphorylation level of the adsorbed substrate is quantitated by contacting with a labeled second antibody reagent that is specific to one or more of the phosphorylation sites. The first antibody reagent may be replaced with an agent such as streptavidin if the peptide substrate is biotinylated (e.g. see HTScan® PAK1 Kinase Assay K1t #7633, or HTScan® PAK2 Kinase Assay Kit #7636, Cell Signaling Technology, Danvers, Mass. 01923).

When the preparation containing PAK1 or PAK2 is a sample of cells, phosphotranferase activity of PAK1 or PAK2 may be determined by monitoring phosphorylation of a protein substrate in the cells (e.g. PAK1 phosphorylation of histone H3, Li et al (2002) EMBO Reports 3(8):767-773; PAK2 phosphorylation of Merlin (Kissil, J. (2002) J Biol. Chem. 277(12): p. 10394-9), or MLCK (Goeckeler, Z. (2000) J Biol Chem. 275(24): p. 18366-74). The level of phosphorylation of the substrate may be determined by electrophoretic separation of the proteins from the cell sample and immunoblot analysis using an antibody reagent specific to one or more PAK1 or PAK2 phosphorylation sites on the substrate. Alternatively, the level of phosphorylation of the substrate is determined using an immunostaining procedure with an antibody reagent that is specific to one or more of the phosphorylation sites on the substrate. The immunostaining procedure may be immunofluorescent detection of phosphorylated substrate protein, using for example cultured cells in a flask or plate, or cell smears from tissue samples, biopsies or needle aspirates. Alternatively, the immunostaining procedure may be immunohistochemical detection of phosphorylated substrate, using for example cell smears from tissue samples, biopsies or needle aspirates, or tissue sections that have been fixed to preserve the tissue structure, e.g. by freezing, or by paraformaldehyde fixation and paraffin embedding. Standard methods for cell or tissue fixation, binding of antibody reagents, and labeling or staining can be employed in these immunostaining procedures (e.g. see Using Antibodies, A Laboratory Manual, edited by Harlow, E. and Lane, D., 1999, Cold Spring Harbor Laboratory Press (e.g. ISBN 0-87969-544-7), particularly chapters 5 and 6 on staining cells and tissues). In the above methods the cells may be engineered to express increased levels of Pak1 or Pak2, and/or substrate proteins for either, in order to improve the sensitivity of such assays.

The present invention also provides a method for treating tumors or tumor metastases in a patient, comprising administering to said patient simultaneously or sequentially a therapeutically effective amount of a combination of an anti-cancer agent that preferentially inhibits epithelial tumor cells, and an inhibitor of PAK2 kinase, wherein said administering is in an amount effective to inhibit epithelial tumor cell growth in said mammal, and to inhibit EMT in said epithelial tumor cells. Examples of anti-cancer agents that preferentially inhibit epithelial tumor cells include EGFR kinase inhibitors (e.g. erlotinib), IGF-1R kinase inhibitors (e.g. OSI-906), and HER-3 inhibitors. Such combination treatments are advantageous over single agent treatments with anti-cancer agents that preferentially inhibit epithelial tumor cells, as tumor cells that may undergo an EMT are additionally targeted with a PAK2 kinase inhibitor, and thus the processes of tumor invasion and metastasis are more effectively inhibited. In one embodiment of this method, the inhibitor of PAK2 kinase also inhibits PAK1 kinase.

In a further embodiment of any of the above methods where an EGFR or IGF-1R kinase inhibitor may be employed, the patient to be treated is tested prior to treatment using a diagnostic assay to determine the sensitivity of tumor cells to an EGFR or IGF-1R kinase inhibitor. Any method known in the art that can determine the sensitivity of the tumor cells of a patient to an EGFR or IGF-1R kinase inhibitor can be employed. For example, a method to determine a patient's likely responsiveness to an EGFR or IGF-1R kinase inhibitor can comprise assessing whether the tumor cells have undergone an epithelial-mesenchymal transition (EMT), by for example determining the expression level of one or more tumor cell epithelial and/or mesenchymal biomarkers, thus identifying the patient as one who is less likely or not likely to demonstrate an effective response to treatment with an EGFR or IGF-1R kinase inhibitor as a single agent if their tumor cells have undergone an EMT (e.g. see Thompson, S. et al. (2005) Cancer Res. 65(20):9455-9462 and US Published Patent Application US-2006-0211060-A1, both incorporated herein by reference; Mulvihill, M. J. et al. (2007) Bioorganic & Medicinal Chemistry Letters 17:1091-1097). For example, the expression level of one or more tumor cell epithelial biomarkers E-cadherin, Brk, γ-catenin, α1-catenin, α2-catenin, α3-catenin, keratin 8, keratin 18, connexin 31, plakophilin 3, stratifin 1, laminin alpha-5, or ST14 can be assessed, a high level indicating that the tumor cells have probably not undergone an EMT. Similarly, the expression level of one or more tumor cell mesenchymal biomarkers, as indicated herein above (e.g. Snail), can be assessed, a high level indicating that the tumor cells have probably undergone an EMT. Other methods that may be utilized to assess the sensitivity of the tumor cells of a patient to an EGFR kinase inhibitor include determining the presence of mutant forms of EGFR known to confer an enhanced sensitivity to EGFR kinase inhibitors. Direct determination in a tumor cell biopsy, or cells derived therefrom, of the sensitivity of a patients tumor cells to an EGFR or IGF-1R kinase inhibitor may also be employed.

For any methods described herein where an EGFR kinase inhibitor is used, an example of a preferred EGFR kinase inhibitor is erlotinib, including pharmacologically acceptable salts or polymorphs thereof. In these methods one or more additional anti-cancer agents or treatments can be co-administered simultaneously or sequentially with the combination therapy that includes the EGFR kinase inhibitor, as judged to be appropriate by the administering physician given the prediction of the likely responsiveness of the patient to the EGFR kinase inhibitor combination, or response to initial therapy, in combination with any additional circumstances pertaining to the individual patient.

For any methods described herein where an IGF-1R kinase inhibitor is used, an example of a preferred EGFR kinase inhibitor is OSI-906, including pharmacologically acceptable salts or polymorphs thereof. In these methods one or more additional anti-cancer agents or treatments can be co-administered simultaneously or sequentially with the combination therapy that includes the IGF-1R kinase inhibitor, as judged to be appropriate by the administering physician given the prediction of the likely responsiveness of the patient to the IGF-1R kinase inhibitor combination, or response to initial therapy, in combination with any additional circumstances pertaining to the individual patient.

Accordingly, the present invention provides a method for treating tumors or tumor metastases in a patient, comprising the steps of diagnosing a patient's likely responsiveness to an EGFR or IGF-1R kinase inhibitor, and administering to said patient simultaneously or sequentially a therapeutically effective amount of a combination of an EGFR or IGF-1R kinase inhibitor and an inhibitor of PAK2 kinase. In one embodiment of this method, the inhibitor of PAK2 kinase also inhibits PAK1 kinase.

The present invention also provides a method for treating tumors or tumor metastases in a patient, comprising the steps of diagnosing a patient's likely responsiveness to an EGFR or IGF-1R kinase inhibitor, identifying the patient as one who has tumor or tumor metastases cells which have undergone an EMT and that are relatively insensitive to an EGFR or IGF-1R kinase inhibitor as a single agent, and thus likely to show an enhanced response to a combination of an EGFR or IGF-1R kinase inhibitor and an inhibitor of a PAK2 kinase, and administering to said patient simultaneously or sequentially a therapeutically effective amount of a combination of an EGFR or IGF-1R kinase inhibitor and an inhibitor of PAK2 kinase. In one embodiment of this method, the inhibitor of PAK2 kinase also inhibits PAK1 kinase.

This invention also provides a method for treating abnormal cell growth of cells in a patient, comprising administering to said patient simultaneously or sequentially a therapeutically effective amount of a combination of an EGFR or IGF-1R kinase inhibitor and an inhibitor of PAK2 kinase. In one embodiment of this method, the inhibitor of PAK2 kinase also inhibits PAK1 kinase.

It will be appreciated by one of skill in the medical arts that the exact manner of administering to said patient of a therapeutically effective amount of a combination of an EGFR or IGF-1R kinase inhibitor and an inhibitor of PAK2 kinase following a diagnosis of a patient's likely responsiveness to an EGFR or IGF-1R kinase inhibitor will be at the discretion of the attending physician. The mode of administration, including dosage, combination with other anti-cancer agents, timing and frequency of administration, and the like, may be affected by the diagnosis of a patient's likely responsiveness to an EGFR or IGF-1R kinase inhibitor, as well as the patient's condition and history. Thus, even patients diagnosed with tumors predicted to be relatively sensitive to an EGFR or IGF-1R kinase inhibitor as a single agent may still benefit from treatment with a combination of an EGFR or IGF-1R kinase inhibitor and an inhibitor of PAK2 kinase, optionally in combination with other anti-cancer agents, or other agents that may alter a tumor's sensitivity to EGFR or IGF-1R kinase inhibitors. Inclusion of inhibitors of EMT may serve a prophylactic role and prevent the migration of tumor cells to other organs, and thus potentially inhibit tumor invastion and/or metastasis.

In one embodiment of the combination treatment methods of this invention, the inhibitor of PAK2 kinase is administered at the same time as the EGFR or IGF-1R kinase inhibitor. In another embodiment of the methods of this invention, the inhibitor of PAK2 kinase is administered prior to the EGFR or IGF-1R kinase inhibitor. In another embodiment of the methods of this invention, the inhibitor of inhibitor of PAK2 kinase is administered after the EGFR or IGF-1R kinase inhibitor. In another embodiment of the methods of this invention, the inhibitor of PAK2 kinase is pre-administered prior to administration of a combination of an EGFR or IGF-1R kinase inhibitor and the inhibitor of PAK2 kinase.

The present invention further provides a method for treating tumors or tumor metastases in a patient, comprising administering to the patient simultaneously or sequentially a therapeutically effective amount of a combination of an EGFR or IGF-1R kinase inhibitor and an inhibitor of PAK2 kinase, and in addition, one or more other cytotoxic, chemotherapeutic, or anti-cancer agents, or compounds that enhance the effects of such agents. In the context of this invention, other anticancer agents includes, for example, other cytotoxic, chemotherapeutic or anti-cancer agents, or compounds that enhance the effects of such agents, antihormonal agents, angiogenesis inhibitors, tumor cell pro-apoptotic or apoptosis-stimulating agents, signal transduction inhibitors, anti-proliferative agents, anti-HER2 antibody or an immunotherapeutically active fragment thereof, anti-proliferative agents, COX II (cyclooxygenase II) inhibitors, and agents capable of enhancing antitumor immune responses.

In the context of this invention, other cytotoxic, chemotherapeutic or anti-cancer agents, or compounds that enhance the effects of such agents, include, for example: alkylating agents or agents with an alkylating action, such as cyclophosphamide (CTX; e.g. CYTOXAN®), chlorambucil (CHL; e.g. LEUKERAN®), cisplatin (CisP; e.g. PLATINOL®) busulfan (e.g. MYLERAN®), melphalan, carmustine (BCNU), streptozotocin, triethylenemelamine (TEM), mitomycin C, and the like; anti-metabolites, such as methotrexate (MTX), etoposide (VP16; e.g. VEPESID®), 6-mercaptopurine (6 MP), 6-thiocguanine (6TG), cytarabine (Ara-C), 5-fluorouracil (5-FU), capecitabine (e.g. XELODA®), dacarbazine (DTIC), and the like; antibiotics, such as actinomycin D, doxorubicin (DXR; e.g. ADRIAMYCIN®), daunorubicin (daunomycin), bleomycin, mithramycin and the like; alkaloids, such as vinca alkaloids such as vincristine (VCR), vinblastine, and the like; and other antitumor agents, such as paclitaxel (e.g. TAXOL®) and pactitaxel derivatives, the cytostatic agents, glucocorticoids such as dexamethasone (DEX; e.g. DECADRON®) and corticosteroids such as prednisone, nucleoside enzyme inhibitors such as hydroxyurea, amino acid depleting enzymes such as asparaginase, leucovorin and other folic acid derivatives, and similar, diverse antitumor agents. The following agents may also be used as additional agents: arnifostine (e.g. ETHYOL®), dactinomycin, mechlorethamine (nitrogen mustard), streptozocin, cyclophosphamide, lomustine (CCNU), doxorubicin lipo (e.g. DOXIL®), gemcitabine (e.g. GEMZAR®), daunorubicin lipo (e.g. DAUNOXOME®), procarbazine, mitomycin, docetaxel (e.g. TAXOTERE®), aldesleukin, carboplatin, oxaliplatin, cladribine, camptothecin, CPT 11 (irinotecan), 10-hydroxy 7-ethyl-camptothecin (SN38), floxuridine, fludarabine, ifosfamide, idarubicin, mesna, interferon beta, interferon alpha, mitoxantrone, topotecan, leuprolide, megestrol, melphalan, mercaptopurine, plicamycin, mitotane, pegaspargase, pentostatin, pipobroman, plicamycin, tamoxifen, teniposide, testolactone, thioguanine, thiotepa, uracil mustard, vinorelbine, chlorambucil.

As used herein, the term "anti-hormonal agent" includes natural or synthetic organic or peptidic compounds that act to regulate or inhibit hormone action on tumors. Antihormonal agents include, for example: steroid receptor antagonists, anti-estrogens such as tamoxifen, raloxifene, aromatase inhibiting 4(5)-imidazoles, other aromatase inhibitors, 42-hydroxytamoxifen, trioxifene, keoxifene, LY 117018, onapristone, and toremifene (e.g. FARESTON®); anti-androgens such as flutamide, nilutamide, bicalutamide, leuprolide, and goserelin; and pharmaceutically acceptable salts, acids or derivatives of any of the above; agonists and/or antagonists of glycoprotein hormones such as follicle stimulating hormone (FSH), thyroid stimulating hormone (TSH), and luteinizing hormone (LH) and LHRH (leuteinizing hormone-releasing hormone); the LHRH agonist goserelin acetate, commercially available as ZOLADEX® (AstraZeneca); the LHRH antagonist D-alaninamide N-acetyl-3-(2-naphthalenyl)-D-alanyl-4-chloro-D-phenylalanyl-3-(3-pyridinyl)-D-alanyl-L-seryl-N6-(3-pyridinylcarbonyl)-L-lysyl-N6-(3-pyridinylcarbonyl)-D-lysyl-L-leucyl-N6-(1-methylethyl)-L-lysyl-L-proline (e.g ANTIDE®, Ares-Serono); the LHRH antagonist ganirelix acetate; the steroidal anti-androgens cyproterone acetate (CPA) and megestrol acetate, commercially available as MEGACE® (Bristol-Myers Oncology); the nonsteroidal anti-androgen flutamide (2-methyl-N-[4,20-nitro-3-(trifluoromethyl) phenylpropanamide), commercially available as EULEXIN® (Schering Corp.); the non-steroidal anti-androgen nilutamide, (5,5-dimethyl-3-[4-nitro-3-(trifluoromethyl-4'-nitrophenyl)-4,4-dimethyl-imidazolidine-dione); and antagonists for other non-permissive receptors, such as antagonists for RAR, RXR, TR, VDR, and the like.

Anti-angiogenic agents include, for example: VEGFR inhibitors, such as SU-5416 and SU-6668 (Sugen Inc. of South San Francisco, Calif., USA), or as described in, for example International Application Nos. WO 99/24440, WO 99/62890, WO 95/21613, WO 99/61422, WO 98/50356, WO 99/10349, WO 97/32856, WO 97/22596, WO 98/54093, WO 98/02438, WO 99/16755, and WO 98/02437, and U.S. Pat. Nos. 5,883,113, 5,886,020, 5,792,783, 5,834,504 and 6,235,764; VEGF inhibitors such as IM862 (Cytran Inc. of Kirkland, Wash., USA); angiozyme, a synthetic ribozyme from Ribozyme (Boulder, Colo.) and Chiron (Emeryville, Calif.); and antibodies to VEGF, such as bevacizumab (e.g. AVASTIN™, Genentech, South San Francisco, Calif.), a recombinant humanized antibody to VEGF; integrin receptor antagonists and integrin antagonists, such as to $\alpha_v\beta_3$, $\alpha_v\beta_5$ and $\alpha_v\beta_6$ integrins, and subtypes thereof, e.g. cilengitide (EMD 121974), or the anti-integrin antibodies, such as for example $\alpha_v\beta_3$ specific humanized antibodies (e.g. VITAXIN®); factors such as IFN-alpha (U.S. Pat. Nos. 41530,901, 4,503,035, and 5,231,176); angiostatin and plasminogen fragments (e.g. kringle 1-4, kringle 5, kringle 1-3 (O'Reilly, M. S. et al. (1994) Cell 79:315-328; Cao et al. (1996) J. Biol. Chem. 271: 29461-29467; Cao et al. (1997) J. Biol. Chem. 272:22924-22928); endostatin (O'Reilly, M. S. et al. (1997) Cell 88:277; and International Patent Publication No. WO 97/15666); thrombospondin (TSP-1; Frazier, (1991) Curr. Opin. Cell Biol. 3:792); platelet factor 4 (PF4); plasminogen activator/urokinase inhibitors; urokinase receptor antagonists; heparinases; fumagillin analogs such as TNP-4701; suramin and suramin analogs; angiostatic steroids; bFGF antagonists; flk-1 and flt-1 antagonists; anti-angiogenesis agents such as MMP-2 (matrix-metalloproteinase 2) inhibitors and MMP-9 (matrix -metalloproteinase 9) inhibitors. Examples of useful matrix metalloproteinase inhibitors are described in International Patent Publication Nos. WO 96/33172, WO 96/27583, WO 98/07697, WO 98/03516, WO 98/34918, WO 98/34915, WO 98/33768, WO 98/30566, WO 90/05719, WO 99/52910, WO 99/52889, WO 99/29667, and WO 99/07675, European Patent Publication Nos. 818,442, 780,386, 1,004,578, 606,046, and 931,788; Great Britain Patent Publication No. 9912961, and U.S. Pat. Nos. 5,863,949 and 5,861,510. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e. MMP-1, MMP-3, MMP-4, MMP-5, MMP-6, MMP-7, MMP-8, MMP-10, MMP-11, MMP-12, and MMP-13).

Signal transduction inhibitors include, for example: erbB2 receptor inhibitors, such as organic molecules, or antibodies that bind to the erbB2 receptor, for example, trastuzumab (e.g. HERCEPTIN®); inhibitors of other protein tyrosine-kinases, e.g. imitinib (e.g. GLEEVEC®); ras inhibitors; raf inhibitors; MEK inhibitors; mTOR inhibitors; cyclin dependent kinase inhibitors; protein kinase C inhibitors; and PDK-1 inhibitors (see Dancey, J. and Sausville, E. A. (2003) Nature Rev. Drug Discovery 2:92-313, for a description of several examples of such inhibitors, and their use in clinical trials for the treatment of cancer).

ErbB2 receptor inhibitors include, for example: ErbB2 receptor inhibitors, such as GW-282974 (Glaxo Wellcome plc), monoclonal antibodies such as AR-209 (Aronex Pharmaceuticals Inc. of The Woodlands, Tex., USA) and 2B-1 (Chiron), and erbB2 inhibitors such as those described in International Publication Nos. WO 98/02434, WO 99/35146, WO 99/35132, WO 98/02437, WO 97/13760, and WO 95/19970, and U.S. Pat. Nos. 5,587,458, 5,877,305, 6,465,449 and 6,541,481.

Antiproliferative agents include, for example. Inhibitors of the enzyme farnesyl protein transferase and inhibitors of the receptor tyrosine kinase PDGFR, including the compounds disclosed and claimed in U.S. Pat. Nos. 6,080,769, 6,194,438, 6,258,824, 6,586,447, 6,071,935, 6,495,564, 6,150,377, 6,596,735 and 6,479,513 and International Patent Publication WO 01/40217. Antiproliferative agents also include inhibitors of the receptor tyrosine kinases IGF-1R and FGFR.

Examples of useful COX-II inhibitors include alecoxib (e.g. CELEBREX™), valdecoxib, and rofecoxib. Agents capable of enhancing antitumor immune responses include, for example: CTLA4 (cytotoxic lymphocyte antigen 4) antibodies (e.g. MDX-CTLA4), and other agents capable of blocking CTLA4. Specific CTLA4 antibodies that can be used in the present invention include those described in U.S. Pat. No. 6,682,736.

The use of the cytotoxic and other anticancer agents described above in chemotherapeutic regimens is generally well characterized in the cancer therapy arts, and their use herein falls under the same considerations for monitoring tolerance and effectiveness and for controlling administration routes and dosages, with some adjustments. For example, the actual dosages of the cytotoxic agents may vary depending upon the patient's cultured cell response determined by using histoculture methods. Generally, the dosage will be reduced compared to the amount used in the absence of additional other agents.

Typical dosages of an effective cytotoxic agent can be in the ranges recommended by the manufacturer, and where indicated by in vitro responses or responses in animal models, can be reduced by up to about one order of magnitude concentration or amount. Thus, the actual dosage will depend upon the judgment of the physician, the condition of the patient, and the effectiveness of the therapeutic method based on the in vitro responsiveness of the primary cultured malignant cells or histocultured tissue sample, or the responses observed in the appropriate animal models.

The present invention further provides a method for treating tumors or tumor metastases in a patient, comprising administering to the patient simultaneously or sequentially a therapeutically effective amount of a combination of an EGFR or IGF-1R kinase inhibitor and an inhibitor of PAK2 kinase, and in addition treatment with radiation or a radiopharmaceutical.

The source of radiation can be either external or internal to the patient being treated. When the source is external to the patient, the therapy is known as external beam radiation therapy (EBRT). When the source of radiation is internal to the patient, the treatment is called brachytherapy (BT). Radioactive atoms for use in the context of this invention can be selected from the group including, but not limited to, radium, cesium-137, iridium-192, americium-241, gold-198, cobalt-57, copper-67, technetium-99, iodine-123, iodine-131, and indium-111. Where the EGFR or IGF-1R kinase inhibitor according to this invention is an antibody, it is also possible to label the antibody with such radioactive isotopes.

Radiation therapy is a standard treatment for controlling unresectable or inoperable tumors and/or tumor metastases. Improved results have been seen when radiation therapy has been combined with chemotherapy. Radiation therapy is based on the principle that high-dose radiation delivered to a target area will result in the death of reproductive cells in both tumor and normal tissues. The radiation dosage regimen is generally defined in terms of radiation absorbed dose (Gy), time and fractionation, and must be carefully defined by the oncologist. The amount of radiation a patient receives will depend on various considerations, but the two most important are the location of the tumor in relation to other critical structures or organs of the body, and the extent to which the tumor has spread. A typical course of treatment for a patient undergoing radiation therapy will be a treatment schedule over a 1 to 6 week period, with a total dose of between 10 and 80 Gy administered to the patient in a single daily fraction of about 1.8 to 2.0 Gy, 5 days a week. In a preferred embodiment of this invention there is synergy when tumors in human patients are treated with the combination treatment of the invention and radiation. In other words, the inhibition of tumor growth by means of the agents comprising the combination of the invention is enhanced when combined with radiation, optionally with additional chemotherapeutic or anticancer agents. Parameters of adjuvant radiation therapies are, for example, contained in International Patent Publication WO 99/60023.

The present invention further provides a method for inhibiting the occurrence of metastases in a patient after treatment to remove or destroy the cells in a primary tumor by chemotherapy and/or surgery comprising administering to said patient a pharmaceutical composition comprising an inhibitor of PAK2 kinase, wherein said administering is in an amount effective to inhibit EMT and migration of tumor cells, and thus the occurrence of metastases. In one embodiment of this method the inhibitor of PAK2 kinase is also an inhibitor of PAK1 kinase. In an alternative embodiment an inhibitor of PAK1 kinase is additionally administered as a separate compound. In an alternative embodiment, one or more other anti-cancer agents may additionally be administered to said mammal. Such anti-cancer agents include for example EGFR kinase inhibitors, such as erlotinib, and IGF-1R kinase inhibitors, such as OSI-906. Other anti-cancer agents may include any of those additional agents described herein.

Additionally, the present invention provides a pharmaceutical composition comprising a combination of an EGFR or IGF-1R kinase inhibitor and an inhibitor of PAK2 kinase in a pharmaceutically acceptable carrier. In one embodiment the PAK2 kinase inhibitor is also an inhibitor of PAK1 kinase.

For purposes of the present invention, "co-administration of" and "co-administering" an EGFR kinase inhibitor (or IGF-1R kinase inhibitor) and an inhibitor of PAK2 kinase (both components referred to hereinafter as the "two active agents") refer to any administration of the two active agents, either separately or together, where the two active agents are administered as part of an appropriate dose regimen designed to obtain the benefit of the combination therapy. Thus, the two active agents can be administered either as part of the same pharmaceutical composition or in separate pharmaceutical compositions. The mesenchymal-like cell kinase inhibitor can be administered prior to, at the same time as, or subsequent to administration of the EGFR or IGF-1R kinase inhibitor, or in some combination thereof. Where the EGFR or IGF-1R kinase inhibitor is administered to the patient at repeated intervals, e.g., during a standard course of treatment, the mesenchymal-like cell kinase inhibitor can be administered prior to, at the same time as, or subsequent to, each administration of the EGFR or IGF-1R kinase inhibitor, or some combination thereof, or at different intervals in relation to the EGFR or IGF-1R kinase inhibitor treatment, or in a single dose prior to, at any time during, or subsequent to the course of treatment with the EGFR or IGF-1R kinase inhibitor.

The EGFR or IGF-1R-kinase inhibitor, or inhibitor of PAK2 kinase, will typically be administered to the patient in a dose regimen that provides for the most effective treatment of the cancer (from both efficacy and safety perspectives) for which the patient is being treated, as known in the art, and as disclosed, e.g. in International Patent Publication No. WO 01/34574. In conducting the treatment method of the present invention, the EGFR or IGF-1R kinase inhibitor, or inhibitor of PAK2 kinase, can be administered in any effective manner known in the art, such as by oral, topical, intravenous, intraperitoneal, intramuscular, intra-articular, subcutaneous, intranasal, intra-ocular, vaginal, rectal, or intradermal routes, depending upon the type of cancer being treated, the type of kinase inhibitor being used (for example, small molecule, antibody, RNAi, ribozyme or antisense construct), and the medical judgement of the prescribing physician as based, e.g., on the results of published clinical studies.

The amount of EGFR or IGF-1R kinase inhibitor, or inhibitor of PAK2 kinase, administered, and the timing of kinase inhibitor administration, will depend on the type (species, gender, age, weight, etc.) and condition of the patient being treated, the severity of the disease or condition being treated, and on the route of administration. For example, small molecule kinase inhibitors can be administered to a patient in doses ranging from 0.001 to 100 mg/kg of body weight per day or per week in single or divided doses, or by continuous infusion (see for example, International Patent Publication No. WO 01/34574). In particular, erlotinib HCl can be administered to a patient in doses ranging from 5-200 mg per day, or 100-1600 mg per week, in single or divided doses, or by continuous infusion. A preferred dose is 150 mg/day. Antibody-based kinase inhibitors, or antisense, RNAi or ribozyme constructs, can be administered to a patient in doses ranging from 0.1 to 100 mg/kg of body weight per day or per week in single or divided doses, or by continuous infusion. In some instances, dosage levels below the lower limit of the aforesaid range may be more than adequate, while in other cases still larger doses may be employed without causing any harmful side effect, provided that such larger doses are first divided into several small doses for administration throughout the day.

The EGFR or IGF-1R kinase inhibitor, and inhibitor of PAK2 kinase, can be administered either separately or together by the same or different routes, and in a wide variety of different dosage forms. For example, the EGFR or IGF-1R kinase inhibitor is preferably administered orally or parenterally. The inhibitor of PAK2 kinase is preferably administered orally or parenterally. Where the EGFR kinase inhibitor is erlotinib HCl (TARCEVA®), oral administration is preferable. Both the EGFR or IGF-1R kinase inhibitors and inhibitor of PAK2 kinase can be administered in single or multiple doses. In one embodiment, the inhibitor of PAK2 kinase is administered first as a pretreatment, followed by administration of the combination of both agents (EGFR or IGF-1R kinase inhibitor and the inhibitor of PAK2 kinase, either separately or combined together in one formulation.

The EGFR or IGF-1R kinase inhibitor, or inhibitor of PAK2 kinase, can be administered with various pharmaceutically acceptable inert carriers in the form of tablets, capsules, lozenges, troches, hard candies, powders, sprays, creams, salves, suppositories, jellies, gels, pastes, lotions, ointments, elixirs, syrups, and the like. Administration of such dosage forms can be carried out in single or multiple doses. Carriers include solid diluents or fillers, sterile aqueous media and various non-toxic organic solvents, etc. Oral pharmaceutical compositions can be suitably sweetened and/or flavored.

The EGFR or IGF-1R kinase inhibitor, or inhibitor of PAK2 kinase, can be combined together with various pharmaceutically acceptable inert carriers in the form of sprays, creams, salves, suppositories, jellies, gels, pastes, lotions, ointments, and the like. Administration of such dosage forms can be carried out in single or multiple doses. Carriers include solid diluents or fillers, sterile aqueous media, and various non-toxic organic solvents, etc.

All formulations comprising proteinaceous EGFR or IGF-1R kinase inhibitors, should be selected so as to avoid denaturation and/or degradation and loss of biological activity of the inhibitor.

Methods of preparing pharmaceutical compositions comprising an EGFR kinase inhibitor are known in the art, and are described, e.g. in International Patent Publication No. WO 01/34574. Methods of preparing pharmaceutical compositions comprising an IGF-1R kinase inhibitor are known in the art. In view of the teaching of the present invention, methods of preparing pharmaceutical compositions comprising both an EGFR or IGF-1R kinase kinase inhibitor and an inhibitor of PAK2 kinase, will be apparent from the above-cited publications and from other known references, such as Remington's Pharmaceutical Sciences, Mack Publishing Company, Easton, Pa., 18$^{th}$ edition (1990).

For oral administration of EGFR or IGF-1R kinase inhibitors, or inhibitor of PAK2 kinase, tablets containing one or both of the active agents are combined with any of various excipients such as, for example, micro-crystalline cellulose, sodium citrate, calcium carbonate, dicalcium phosphate and glycine, along with various disintegrants such as starch (and preferably corn, potato or tapioca starch), alginic acid and certain complex silicates, together with granulation binders like polyvinyl pyrrolidone, sucrose, gelatin and acacia. Additionally, lubricating agents such as magnesium stearate, sodium lauryl sulfate and talc are often very useful for tableting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the EGFR or IGF-1R kinase inhibitors, or inhibitor of PAK2 kinase, may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration of either or both of the active agents, solutions in either sesame or peanut oil or in aqueous propylene glycol may be employed, as well as sterile aqueous solutions comprising the active agent or a corresponding water-soluble salt thereof. Such sterile aqueous solutions are preferably suitably buffered, and are also preferably rendered isotonic, e.g., with sufficient saline or glucose. These particular aqueous solutions are especially suitable for intravenous, intramuscular, subcutaneous and intraperitoneal injection purposes. The oily solutions are suitable for intra-articular, intramuscular and subcutaneous injection purposes. The preparation of all these solutions under sterile conditions is readily accomplished by standard pharmaceutical techniques well known to those skilled in the art. Any parenteral formulation selected for administration of proteinaceous kinase inhibitors should be selected so as to avoid denaturation and loss of biological activity of the inhibitor.

Additionally, it is possible to topically administer either or both of the active agents, by way of, for example, creams, lotions, jellies, gels, pastes, ointments, salves and the like, in accordance with standard pharmaceutical practice. For example, a topical formulation comprising an EGFR or IGF-1R kinase inhibitor, or inhibitor of PAK2 kinase, in about 0.1% (w/v) to about 5% (w/v) concentration can be prepared.

For veterinary purposes, the active agents can be administered separately or together to animals using any of the forms and by any of the routes described above. In a preferred embodiment, the EGFR or IGF-1R kinase inhibitor, or inhibitor of PAK2 kinase, is administered in the form of a capsule, bolus, tablet, liquid drench, by injection or as an implant. As an alternative, the kinase inhibitor can be administered with the animal feedstuff, and for this purpose a concentrated feed additive or premix may be prepared for a normal animal feed. The kinase inhibitors can also be administered in the form of liquid drench, by injection, or as an implant. Such formulations are prepared in a conventional manner in accordance with standard veterinary practice.

The present invention further provides a kit comprising a single container comprising both an EGFR (or IGF-1R) kinase inhibitor, and inhibitor of PAK2 kinase. The present invention further provides a kit comprising a first container comprising an EGFR (or IGF-1R) kinase inhibitor and a second container comprising an inhibitor of PAK2 kinase. In a preferred embodiment, the kit containers may further include a pharmaceutically acceptable carrier. The kit may further include a sterile diluent, which is preferably stored in a separate additional container. The kit may further include a package insert comprising printed instructions directing the use of the combined treatment as a method for treating cancer. The kit may also comprise additional containers comprising additional anti-cancer agents, agents that enhances the effect of such agents, or other compounds that improve the efficacy or tolerability of the treatment.

As used herein, the term "EGFR kinase inhibitor" refers to any EGFR kinase inhibitor that is currently known in the art or that will be identified in the future, and includes any chemical entity that, upon administration to a patient, results in inhibition of a biological activity associated with activation of the EGF receptor in the patient, including any of the downstream biological effects otherwise resulting from the binding to EGFR of its natural ligand. Such EGFR kinase inhibitors include any agent that can block EGFR activation or any of the downstream biological effects of EGFR activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the EGF receptor, thereby making the receptor inaccessible to its natural ligand so that its normal biological activity is prevented or reduced. Alternatively, such an inhibitor can act by modulating the dimerization of EGFR polypeptides, or interaction of EGFR polypeptide with other proteins, or enhance ubiquitination and endocytotic degradation of EGFR. EGFR kinase inhibitors include but are not limited to low molecular weight inhibitors, antibodies or antibody fragments, peptide or RNA aptamers, antisense constructs, small inhibitory RNAs (i.e. RNA interference by dsRNA; RNAi), and ribozymes. In a preferred embodiment, the EGFR kinase inhibitor is a small organic molecule or an antibody that binds specifically to the human EGFR.

EGFR kinase-inhibitors include, for example quinazoline EGFR kinase inhibitors, pyrido-pyrimidine BGFR kinase inhibitors, pyrimido-pyrimidine BGFR kinase inhibitors, pyrrolo-pyrimidine EGFR kinase inhibitors, pyrazolo-pyrimidine EGFR kinase inhibitors, phenylamino-pyrimidine EGFR kinase inhibitors, oxindole EGFR kinase inhibitors, indolocarbazole EGFR kinase inhibitors, phthalazine EGFR kinase inhibitors, isoflavone EGFR kinase inhibitors, quinalone EGFR kinase inhibitors, and tyrphostin EGFR kinase inhibitors, such as those described in the following patent publications, and all pharmaceutically acceptable salts and solvates of said EGFR kinase inhibitors: International Patent Publication Nos. WO 96/33980, WO 96/30347, WO 97/30034, WO 97/30044, WO 97/38994, WO 97/49688, WO 98/02434, WO 97/38983, WO 95/19774, WO 95/19970, WO 97/13771, WO 98/02437, WO 98/02438, WO 97/32881, WO 98/33798, WO 97/32880, WO 97/3288, WO 97/02266, WO 97/27199, WO 98/07726, WO 97/34895, WO 96/31510, WO 98/14449, WO 98/14450, WO 98/14451, WO 95/09847, WO 97/19065, WO 98/17662, WO 99/35146, WO 99/35132, WO 99/07701, and WO 92/20642; European Patent Application Nos. EP 520722, EP 566226, EP 787772, EP 837063, and EP 682027; U.S. Pat. Nos. 5,747,498, 5,789,427, 5,650,415, and 5,656,643; and German Patent Application No. DE 19629652. Additional non-limiting examples of low molecular weight EGFR kinase inhibitors include any of the EGFR kinase inhibitors described in Traxler, P., 1998, Exp. Qpin. Ther. Patents 8(12):1599-1625.

Specific preferred examples of low molecular weight EGFR kinase inhibitors that can be used according to the present invention include [6,7-bis(2-methoxyethoxy)-4-quinazolin-4-yl]-(3-ethynylphenyl) amine (also known as OSI-774, erlotinib, or TARCEVA® (erlotinib HCl); OSI Pharmaceuticals/Genentech/Roche) (U.S. Pat. No. 5,747,498; International Patent Publication No. WO 01/34574, and Moyer, J. D. et al. (1997) Cancer Res. 57:4838-4848); CI-1033 (formerly known as PD183805; Pfizer) (Sherwood et al., 1999, Proc. Am. Assoc. Cancer Res. 40:723); PD-158780 (Pfizer); AG-1478 (University of California); CGP-59326 (Novartis); PKI-166 (Novartis); EKB-569 (Wyeth); GW-2016 (also known as GW-572016 or lapatinib ditosylate; GSK); and gefitinib (also known as ZD1839 or IRESSA™; Astrazeneca) (Woodburn et al., 1997, Proc. Am. Assoc. Cancer Res. 38:633). A particularly preferred low molecular weight EGFR kinase inhibitor that can be used according to the present invention is [6,7-bis(2-methoxyethoxy)-4-quinazolin-4-yl]-(3-ethynylphenyl) amine (i.e. erlotinib), its hydrochloride salt (i.e. erlotinib HCl, TARCEVA®), or other salt forms (e.g. erlotinib mesylate).

EGFR kinase inhibitors also include, for example multi-kinase inhibitors that have activity on EGFR kinase, i.e. inhibitors that inhibit EGFR kinase and one or more additional kinases. Examples of such compounds include the EGFR and HER2 inhibitor CI-1033 (formerly known as PD183805; Pfizer); the EGFR and HER2 inhibitor GW-2016 (also known as GW-572016 or lapatinib ditosylate; GSK); the EGFR and JAK 2/3 inhibitor AG490 (a tyrphostin); the EGFR and HER2 inhibitor ARRY-334543 (Array BioPharma); BIBW-2992, an irreversible dual EGFR/HER2 kinase inhibitor (Boehringer Ingelheim Corp.); the EGFR and HER2 inhibitor EKB-569 (Wyeth); the VEGF-R2 and EGFR inhibitor ZD6474 (also known as ZACTIMA™; AstraZeneca Pharmaceuticals), and the EGFR and HER2 inhibitor BMS-599626 (Bristol-Myers Squibb).

Antibody-based EGFR kinase inhibitors include any anti-EGFR antibody or antibody fragment that can partially or completely block EGFR activation by its natural ligand. Non-limiting examples of antibody-based EGFR kinase inhibitors include those described in Modjtahedi, H., et al., 1993, Br. J. Cancer 67:247-253; Teramoto, T., et al., 1996, Cancer 77:639-645; Goldstein et al., 1995, Clin. Cancer Res. 1:1311-1318; Huang, S. M., et al., 1999, Cancer Res. 15:59(8):1935-40; and Yang, X., et al., 1999, Cancer Res. 59:1236-1243. Thus, the EGFR kinase inhibitor can be the monoclonal antibody Mab E7.6.3 (Yang, X. D. et al. (1999) Cancer Res. 59:1236-43), or Mab C225 (ATCC Accession No. HB-8508), or an antibody or antibody fragment having the binding specificity thereof. Suitable monoclonal antibody EGFR kinase inhibitors include, but are not limited to, IMC-C225 (also known as cetuximab or ERBITUX™; Imclone Systems), ABX-EGF (Abgenix), EMD 72000 (Merck KgaA, Darmstadt), RH3 (York Medical Bioscience Inc.), and MDX-447 (Medarex/Merck KgaA).

EGFR kinase inhibitors for use in the present invention can alternatively be peptide or RNA aptamers. Such aptamers can for example interact with the extracellular or intracellular domains of EGFR to inhibit EGFR kinase activity in cells. An aptamer that interacts with the extracellular domain is preferred as it would not be necessary for such an aptamer to cross the plasma membrane of the target cell. An aptamer could also interact with the ligand for EGFR (e.g. EGF, TGF-α), such that its ability to activate EGFR is inhibited. Methods for selecting an appropriate aptamer are well known in the art. Such methods have been used to select both peptide and RNA aptamers that interact with and inhibit EGFR family members (e.g. see Buerger, C. et al. et al. (2003) J. Biol. Chem. 278: 37610-37621; Chen, C-H. B. et al. (2003) Proc. Natl. Acad.

Sci. 100:9226-9231; Buerger, C. and Groner, B. (2003) J. Cancer Res. Clin. Oncol. 129(12):669-675. Epub 2003 Sep. 11.).

EGFR kinase inhibitors for use in the present invention can alternatively be based on antisense oligonucleotide constructs. Anti-sense oligonucleotides, including anti-sense RNA molecules and anti-sense DNA molecules, would act to directly block the translation of EGFR mRNA by binding thereto and thus preventing protein translation or increasing mRNA degradation, thus decreasing the level of EGFR kinase protein, and thus activity, in a cell. For example, antisense oligonucleotides of at least about 15 bases and complementary to unique regions of the mRNA transcript sequence encoding EGFR can be synthesized, e.g., by conventional phosphodiester techniques and administered by e.g., intravenous injection or infusion. Methods for using antisense techniques for specifically inhibiting gene expression of genes whose sequence is known are well known in the art (e.g. see U.S. Pat. Nos. 6,566,135; 6,566,131; 6,365,354; 6,410,323; 6,107,091; 6,046,321; and 5,981,732).

Small inhibitory RNAs (siRNAs) can also function as EGFR kinase inhibitors for use in the present invention. EGFR gene expression can be reduced by contacting the tumor, subject or cell with a small double stranded RNA (dsRNA), or a vector or construct causing the production of a small double stranded RNA, such that expression of EGFR is specifically inhibited (i.e. RNA interference or RNAi). Methods for selecting an appropriate dsRNA or dsRNA-encoding vector are well known in the art for genes whose sequence is known (e.g. see Tuschi, T., et al. (1999) Genes Dev. 13(24): 3191-3197; Elbashir, S. M. et al. (2001) Nature 411:494-498; Hannon, G. J. (2002) Nature 418:244-251; McManus, M. T. and Sharp, P. A. (2002) Nature Reviews Genetics 3:737-747; Bremmelkamp, T. R. et al. (2002) Science 296:550-553; U.S. Pat. Nos. 6,573,099 and 6,506,559; and International Patent Publication Nos. WO 01/36646, WO 99/32619, and WO 01/68836).

Ribozymes can also function as EGFR kinase inhibitors for use in the present invention. Ribozymes are enzymatic RNA molecules capable of catalyzing the specific cleavage of RNA. The mechanism of ribozyme action involves sequence specific hybridization of the ribozyme molecule to complementary target RNA, followed by endonucleolytic cleavage. Engineered hairpin or hammerhead motif ribozyme molecules that specifically and efficiently catalyze endonucleolytic cleavage of EGFR mRNA sequences are thereby useful within the scope of the present invention. Specific ribozyme cleavage sites within any potential RNA target are initially identified by scanning the target molecule for ribozyme cleavage sites, which typically include the following sequences, GUA, GUU, and GUC. Once identified, short RNA sequences of between about 15 and 20 ribonucleotides corresponding to the region of the target gene containing the cleavage site can be evaluated for predicted structural features, such as secondary structure, that can render the oligonucleotide sequence unsuitable. The suitability of candidate targets can also be evaluated by testing their accessibility to hybridization with complementary oligonucleotides, using, e.g., ribonuclease protection assays.

Both antisense oligonucleotides and ribozymes useful as EGFR kinase inhibitors can be prepared by known methods. These include techniques for chemical synthesis such as, e.g., by solid phase phosphoramadite chemical synthesis. Alternatively, anti-sense RNA molecules can be generated by in vitro or in vivo transcription of DNA sequences encoding the RNA molecule. Such DNA sequences can be incorporated into a wide variety of vectors that incorporate suitable RNA polymerase promoters such as the T7 or SP6 polymerase promoters. Various modifications to the oligonucleotides of the invention can be introduced as a means of increasing intracellular stability and half-life. Possible modifications include but are not limited to the addition of flanking sequences of ribonucleotides or deoxyribonucleotides to the 5' and/or 3' ends of the molecule, or the use of phosphorothioate or 2'-O-methyl rather than phosphodiesterase linkages within the oligonucleotide backbone.

As used herein, the term "IGF-1R kinase inhibitor" refers to any IGF-1R kinase inhibitor that is currently known in the art or that will be identified in the future, and includes any chemical entity that, upon administration to a patient, results in inhibition of a biological activity associated with activation of the IGF-1 receptor in the patient, including any of the downstream biological effects otherwise resulting from the binding to IGF-1R of its natural ligand. Such IGF-1R kinase inhibitors include any agent that can block IGF-1R activation or any of the downstream biological effects of IGF-1R activation that are relevant to treating cancer in a patient. Such an inhibitor can act by binding directly to the intracellular domain of the receptor and inhibiting its kinase activity. Alternatively, such an inhibitor can act by occupying the ligand binding site or a portion thereof of the IGF-1 receptor, thereby making the receptor inaccessible to its natural ligand so that its normal biological activity is prevented or reduced. Alternatively, such an inhibitor can act by modulating the dimerization of IGF-1R polypeptides, or interaction of IGF-1R polypeptide with other proteins, or enhance ubiquitination and endocytotic degradation of IGF-1R. An IGF-1R kinase inhibitor can also act by reducing the amount of IGF-1 available to activate IGF-1R, by for example antagonizing the binding of IGF-1 to its receptor, by reducing the level of IGF-1, or by promoting the association of IGF-1 with proteins other than IGF-1R such as IGF binding proteins (e.g. IGFBP3). IGF-1R kinase inhibitors include but are not limited to low molecular weight inhibitors, antibodies or antibody fragments, antisense constructs, small inhibitory RNAs (i.e. RNA interference by dsRNA; RNAi), and ribozymes. In a preferred embodiment, the IGF-1R kinase inhibitor is a small organic molecule or an antibody that binds specifically to the human IGF-1R.

IGF-1R kinase inhibitors include, for example imidazopyrazine IGF-1R kinase inhibitors, azabicyclic amine inhibitors, quinazoline IGF-1R kinase inhibitors, pyrido-pyrimidine IGF-1R kinase inhibitors, pyrimido-pyrimidine IGF-1R kinase inhibitors, pyrrolo-pyrimidine IGF-1R kinase inhibitors, pyrazolo-pyrimidine IGF-1R kinase inhibitors, phenylamino-pyrimidine IGF-1R kinase inhibitors, oxindole IGF-1R kinase inhibitors, indolocarbazole IGF-1R kinase inhibitors, phthalazine IGF-1R kinase inhibitors, isoflavone IGF-1R kinase inhibitors, quinalone IGF-1R kinase inhibitors, and tyrphostin IGF-1R kinase inhibitors, and all pharmaceutically acceptable salts and solvates of such IGF-1R kinase inhibitors.

Examples of IGF-1R kinase inhibitors include those in International Patent Publication No. WO 05/097800, that describes azabicyclic amine derivatives, International Patent Publication No. WO 05/037836, that describes imidazopyrazine IGF-1R kinase inhibitors, International Patent Publication Nos. WO 03/018021 and WO 03/018022, that describe pyrimidines for treating IGF-1R related disorders, International Patent Publication Nos. WO 02/102804 and WO 02/102805, that describe cyclolignans and cyclolignans as IGF-1R inhibitors, International Patent Publication No. WO 02/092599, that describes pyrrolopyrimidines for the treatment of a disease which responds to an inhibition of the IGF-1R tyrosine kinase, International Patent Publication No. WO 01/72751, that describes pyrrolopyrimidines as tyrosine kinase inhibitors, and in International Patent Publication No. WO. 00/71129, that describes pyrrolotriazine inhibitors of kinases, and in International Patent Publication No. WO 97/28161, that describes pyrrolo[2,3-d]pyrimidines and their use as tyrosine kinase inhibitors, Parrizas, et al., which describes tyrphostins with in vitro and in vivo IGF-1R inhibitory activity (Endocrinology, 138:1427-1433 (1997)), International Patent Publication No. WO 00/35455, that describes heteroaryl-aryl ureas as IGF-1R inhibitors, International Patent Publication No. WO 03/048133, that describes pyrimidine derivatives as modulators of IGF-1R, International Patent Publication No. WO 03/024967, WO 03/035614, WO 03/035615, WO 03/035616, and WO 03/035619, that describe chemical compounds with inhibitory effects towards kinase proteins, International Patent Publication No. WO 03/068265, that describes methods and compositions for treating hyperproliferative conditions, International Patent Publication No. WO 00/17203, that describes pyrrolopyrimidines as protein kinase inhibitors, Japanese Patent Publication No. JP 07/133,280, that describes a cephem compound, its production and antimicrobial composition, Albert, A. et al., *Journal of the Chemical Society*, 11: 1540-1547 (1970), which describes pteridine studies and pteridines unsubstituted in the 4-position, and A. Albert et al., *Chem. Biol. Pteridines Proc. Int. Symp.*, 4th, 4: 1-5 (1969) which describes a synthesis of pteridines (unsubstituted in the 4-position) from pyrazines, via 3-4-dihydropteridines.

Additional, specific examples of IGF-1R kinase inhibitors that can be used according to the present invention include h7C10 (Centre de Recherche Pierre Fabre), an IGF-1 antagonist; EM-164 (ImmunoGen Inc.), an IGF-1R modulator; CP-751871 (Pfizer Inc.), an IGF-1 antagonist; lanreotide (Ipsen), an IGF-1 antagonist; IGF-1R oligonucleotides (Lynx Therapeutics Inc.); IGF-1 oligonucleotides (National Cancer Institute); IGF-1R protein-tyrosine kinase inhibitors in development by Novartis (e.g. NVP-AEW541, Garcia-Echeverria, C. et al. (2004) Cancer Cell 5:231-239; or NVP-ADW742, Mitsiades, C. S. et al. (2004) Cancer Cell 5:221-230); IGF-1R protein-tyrosine kinase inhibitors (Ontogen Corp); OSI-906 (OSI Pharmaceuticals); AG-1024 (Camirand, A. et al. (2005) Breast Cancer Research 7:R570—R579 (DOI 10.1186/bcr1028); Camirand, A. and Pollak, M. (2004) Brit. J. Cancer 90:1825-1829; Pfizer Inc.), an IGF-1 antagonist; the tyrphostins AG-538 and I-OMe-AG 538; BMS-536924, a small molecule inhibitor of IGF-1R; PNU-145156E (Pharmacia & Upjohn SpA), an IGF-1 antagonist; BMS 536924, a dual IGF-1R and IR kinase inhibitor (Bristol-Myers Squibb); AEW541 (Novartis); GSK621659A (Glaxo Smith-Kline); INSM-18 (Insmed); and XL-228 (Exelixis).

Antibody-based IGF-1R kinase inhibitors include any anti-IGF-1R antibody or antibody fragment that can partially or completely block IGF-1R activation by its natural ligand. Antibody-based IGF-1R kinase inhibitors also include any anti-IGF-1 antibody or antibody fragment that can partially or completely block IGF-1R activation. Non-limiting examples of antibody-based IGF-1R kinase inhibitors include those described in Larsson, O. et al (2005) Brit. J. Cancer 92:2097-2101 and Ibrahim, YH and Yee, D. (2005) Clin. Cancer Res. 11:944s-950s; or being developed by Imclone (e.g. IMC-A12), or AMG-479, an anti-IGF-1R antibody (Amgen); R1507, an anti-IGF-1R antibody (Genmab/Roche); AVE-1642, an anti-IGF-1R antibody (Immunogen/Sanofi-Aventis); MK 0646 or h7C10, an anti-IGF-1R antibody (Merck); or antibodies being develop by Schering-Plough Research Institute (e.g. SCH 717454 or 19D12; or as described in US Patent Application Publication Nos. US 2005/0136063 A1 and US 2004/0018191 A1). The IGF-1R kinase inhibitor can be a monoclonal antibody, or an antibody or antibody fragment having the binding specificity thereof.

The present invention also encompasses the use of a combination of an EGFR (or IGF-1R) kinase inhibitor, and an inhibitor of PAK2 kinase, for the manufacture of a medicament for the treatment of tumors or tumor metastases in a patient in need thereof, wherein each inhibitor in the combination can be administered to the patient either simultaneously or sequentially. The present invention also encompasses the use of a synergistically effective combination of an EGFR (or IGF-1R) kinase inhibitor, and an inhibitor of PAK2 kinase, for the manufacture of a medicament for the treatment of tumors or tumor metastases in a patient in need thereof, wherein each inhibitor in the combination can be administered to the patient either simultaneously or sequentially. In an embodiment of any of the above uses, some of the cells of the tumors or tumor metastases have low sensitivity or are relatively insensitive to growth inhibition by EGFR (or IGF1R) kinase inhibitors (e.g. erlotinib (or OSI-906)) as single agents, such as epithelial cells that have undergone an EMT and have acquired mesenchymal characteristics (e.g. like H460 or Calu6 tumor cells). In an alternative embodiment of any of the above uses the present invention also encompasses the use of a combination of an EGFR (or IGF-1R) kinase inhibitor, and an inhibitor of PAK2 kinase in combination with another anti-cancer agent or agent that enhances the effect of such an agent for the manufacture of a medicament for the treatment of tumors or tumor metastases in a patient in need thereof, wherein each inhibitor in the combination can be administered to the patient either simultaneously or sequentially. In this context, the other anti-cancer agent or agent that enhances the effect of such an agent can be any of the agents listed above that can be added to the EGFR (or IGF-1R) kinase inhibitor combinations when treating patients.

The invention also encompasses a pharmaceutical composition that is comprised of a combination of an EGFR (or IGF-1R) kinase inhibitor and an inhibitor of PAK2 kinase in combination with a pharmaceutically acceptable carrier.

Preferably the composition is comprised of a pharmaceutically acceptable carrier and a non-toxic therapeutically effective amount of a combination of an EGFR (or IGF-1R) kinase inhibitor, and an inhibitor of PAK2 kinase (including pharmaceutically acceptable salts of each component thereof).

Moreover, within this preferred embodiment, the invention encompasses a pharmaceutical composition for the treatment of disease, the use of which results in the inhibition of growth of neoplastic cells, benign or malignant tumors, or metastases, comprising a pharmaceutically acceptable carrier and a non-toxic therapeutically effective amount of a combination of an EGFR (or IGF-1R) kinase inhibitor, and an inhibitor of PAK2 kinase (including pharmaceutically acceptable salts of each component thereof).

The term "pharmaceutically acceptable salts" refers to salts prepared from pharmaceutically acceptable non-toxic bases or acids. When a compound of the present invention is acidic, its corresponding salt can be conveniently prepared from pharmaceutically acceptable non-toxic bases, including inorganic bases and organic bases. Salts derived from such inorganic bases include aluminum, ammonium, calcium, copper (cupric and cuprous), ferric, ferrous, lithium, magnesium, manganese (manganic and manganous), potassium, sodium, zinc and the like salts. Particularly preferred are the ammonium, calcium, magnesium, potassium and sodium salts. Salts derived from pharmaceutically acceptable organic non-toxic bases include salts of primary, secondary, and tertiary amines, as well as cyclic amines and substituted amines such as naturally occurring and synthesized substituted amines. Other pharmaceutically acceptable organic non-toxic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine; glucosamine, histidine, hydrabamine, isopropylamine, lysine, methylglucamine, morpholine, piperazine, piperidine, polyamine resins, procaine, purines, theobromine, triethylameine, trimethylamine, tripropylamine, tromethamine and the like.

When a compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Particularly preferred are citric, hydrobromic, hydrochloric, maleic, phosphoric, sulfuric and tartaric acids.

The pharmaceutical compositions of the present invention comprise a combination of an EGFR (or IGF-1R) kinase inhibitor, and an inhibitor of PAK2 kinase (including pharmaceutically acceptable salts of each component thereof) as active ingredients, a pharmaceutically acceptable carrier and optionally other therapeutic ingredients or adjuvants. Other therapeutic agents may include those cytotoxic, chemotherapeutic or anti-cancer agents, or agents which enhance the effects of such agents, as listed above. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

In practice, the compounds represented by the combination of an EGFR (or IGF-1R) kinase inhibitor, and an inhibitor of PAK2 kinase (including pharmaceutically acceptable salts of each component thereof) of this invention can be combined as the active ingredient in intimate admixture with a pharmaceutical carrier according to conventional pharmaceutical compounding techniques. The carrier may take a wide variety of forms depending on the form of preparation desired for administration, e.g. oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, a combination of an EGFR (or IGF-1R) kinase inhibitor, and an inhibitor of PAK2 kinase (including pharmaceutically acceptable salts of each component thereof) may also be administered by controlled release means and/or delivery devices. The combination compositions may be prepared by any of the methods of pharmacy. In general, such methods include a step of bringing into association the active ingredients with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

Thus, the pharmaceutical compositions of this invention may include a pharmaceutically acceptable carrier and a combination of an EGFR (or IGF-1R) kinase inhibitor, and an inhibitor of PAK2 kinase (including pharmaceutically acceptable salts of each component thereof). A combination of an EGFR (or IGF-1R) kinase inhibitor, and an inhibitor of PAK2 kinase (including pharmaceutically acceptable salts of each component thereof), can also be included in pharmaceutical compositions in combination with one or more other therapeutically active compounds. Other therapeutically active compounds may include those cytotoxic, chemotherapeutic or anti-cancer agents, or agents which enhance the effects of such agents, as listed above.

Thus in one embodiment of this invention, a pharmaceutical composition can comprise a combination of an EGFR (or IGF-1R) kinase inhibitor, and an inhibitor of PAK2 kinase in combination with an anticancer agent, wherein said anticancer agent is a member selected from the group consisting of alkylating drugs, antimetabolites, microtubule inhibitors, podophyllotoxins, antibiotics, nitrosoureas, hormone therapies, kinase inhibitors, activators of tumor cell apoptosis, and antiangiogenic agents.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

In preparing the compositions for oral dosage form, any convenient pharmaceutical media may be employed. For example, water, glycols, oils, alcohols, flavoring agents, preservatives, coloring agents, and the like may be used to form oral liquid preparations such as suspensions, elixirs and solutions; while carriers such as starches, sugars, microcrystalline cellulose, diluents, granulating agents, lubricants, binders, disintegrating agents, and the like may be used to form oral solid preparations such as powders, capsules and tablets. Because of their ease of administration, tablets and capsules are the preferred oral dosage units whereby solid pharmaceutical carriers are employed. Optionally, tablets may be coated by standard aqueous or nonaqueous techniques.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably contains from about 0.05 mg to about 5 g of the active ingredient.

For example, a formulation intended for the oral administration to humans may contain from about 0.5 mg to about 5 g of active agent, compounded with an appropriate and convenient amount of carrier material that may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical sue such as, for example, an aerosol, cream, ointment, lotion, dusting powder, or the like. Further, the compositions can be in a form suitable for use in transdermal devices. These formulations may be prepared, utilizing a combination of an EGFR (or IGF-1R) kinase inhibitor, and an inhibitor of PAK2 kinase (including pharmaceutically acceptable salts of each component thereof) of this invention, via conventional processing methods. As an example, a cream or ointment is prepared by admixing hydrophilic material and water, together with about 5 wt % to about 10 wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a combination of an EGFR (or IGF-1R) kinase inhibitor, and an inhibitor of PAK2 kinase (including pharmaceutically acceptable salts of each component thereof) may also be prepared in powder or liquid concentrate form.

Dosage levels for the compounds of the combination of this invention will be approximately as described herein, or as described in the art for these compounds. It is understood, however, that the specific dose level for any particular patient will depend upon a variety of factors including the age, body weight, general health, sex, diet, time of administration, route of administration, rate of excretion, drug combination and the severity of the particular disease undergoing therapy.

This invention will be better understood from the Experimental Details that follow. However, one skilled in the art will readily appreciate that the specific methods and results discussed are merely illustrative of the invention as described more fully in the claims which follow thereafter, and are not to be considered in any way limited thereto.

Experimental Details

Materials and Methods

Drugs/compounds: Human recombinant mature TGF-beta3 was prepared and purified at OSI Pharmaceuticals using standard techniques.

PAK2 siRNA: target sequence (SEQ ID NO:2; 5'-GCGAC-CGGAUCAUACGAAAUCAAUU-3'; position 690). This was purchased from Invitrogen (duplex 1 of PAK2 Validated Stealth™ DuoPak).

PAK1 siRNA: sequence (SEQ ID NO:4; 5'-GAUGAGAAAUACCAGCACUAUGAUU-3'; position 406). This was purchased from Invitrogen (duplex 2 of PAK1 Validated Stealth™ DuoPak). TGFBRI inhibitor SB431542 was purchased from Sigma-Aldrich, St. Louis, Mo.; (product #S4317).

Cell lines: The human cancer cell lines H358 and HCT116 were purchased from the American Type Culture Collection (ATCC), and were grown in media as prescribed by the ATCC, containing 10% FCS. The HCT116/tet-on/Snail-Flag cell line was generated by transfecting HCT116 cells with two plasmids, one (pcDNA6-rtTA2S-M2) coding for the reverse tetracycline trans-activator protein rtTA2S-M2 (Urlinger, S. (2000) et al Proc Natl Acad Sci USA. 97(14): p. 7963-8) and blasticidin resistance gene, and the other (pTet-tTS, Clontech) coding for the tetracycline trans-silencer protein tTS. A 10:1 ratio of PTet-tTS to pcDNA6-rtTA2S-M2 was used in the transfection and stable clones were selected in media containing blasticidin. Blasticidin-resistant clones were tested for inducibility by doxycycline after transient transfection with the Tet-responsive luciferase reporter plasmid pTRE2-Luc (Clontech). One clone that gave ~10-fold induction of luciferase with doxycycline was used in follow-up transfection with a plasmid (pTRE2pur-Snail-Flag) coding for the Snail-Flag gene under the control of a Tet-regulated promoter. Selection in puromycin-containing media yielded several stable clones. One that showed low basal expression of the Snail-Flag transgene and good induction by doxycycline was used in experiments described herein.

siRNA knockdown and TGFβ3 treatment: For PAK1 and PAK2 siRNA knockdown in H358 cells, cells were seeded at a density of $5\times10^4$ cells/well in 6-well dishes. Next day, the cells were transfected using Lipofectamine 2000 (Invitrogen, 11668-019) with 62.5 nM PAK1 (Invitrogen; validated stealth siRNAduplex2, 12936-54) 62.5 nM PAK2 (Invitrogen; validated stealth siRNA duplex 1, 12936-55), 62.5 nM PAK1 & 62.5 nM PAK2 siRNA, or 62.5 nM negative control (Invitrogen, 12935-300) according to the manufacturer's instructions. Transfection reagent was replaced 4 hours post transfection with fresh media. The cells were re-transfected as above 48 hrs after initial transfection. 4 hours post-transfection, the transfection reagent was replaced with fresh media plus or minus 10 nM TGFβ3.

For siRNA knockdown in HCT116/tet-on/Snail-Flag cells, cells were seeded at a density of $2.5\times10^4$ cells/well in 6-well dishes and transfected the next day. Transfection conditions were similar to those of H358 cells. Twenty four hours post transfection Doxycycline was added at a concentration of 0.5 ug/ml to induce the expression of Snail.

Western blot analysis: For western blot analysis in H358 cells, cells were harvested 72 hrs after the addition of TGFβ3 addition (5 and 3 days after first and second siRNA transfections). For western blot analysis in HCT116/tet-on/Snail-Flag cells, cells were harvested 24 hours after Dox addition. Lysis was achieved with RIPA buffer (Sigma, Saint Louis, Mo.; R0278) containing Protease Inhibitor Cocktail (Sigma, P8340), Phosphatase Inhibitor Cocktail 1 (Sigma, P2850) and Cocktail 2 (Sigma, P5726). Cell lysates were cleared of insoluble material by centrifugation at 15,000×g for 5 minutes at 4° C. Protein concentrations were measured in the resultant supernatant using the BCA protein analysis kit (Promega, Madison Wis.; 23225). 15 ug total lysate was used for SDS-PAGE followed by immunoblotting with the appropriate antibodies. The following antibodies were used: E-cadherin (Cell Signaling, Beverly, Mass.; 3195), vimentin (BD Biosciences, San Jose, Calif.; 550513), ErbB3 (Santa Cruz Biotechnology, Santa Cruz, Calif.; sc285), PAK1 (Cell Signaling, 2062), PAK2 (Cell Signaling, 2068), Flag (Sigma, F3165), ZEB1 (Santa Cruz, sc25388), N-Cadherin (Santa Cruz, sc7939), Fibronection (BD, 610078), β-action (Sigma, A1978).

RNA isolation and TaqMan analysis: For TaqMan analysis, total RNA was isolated 72 hours after TGFβ3 treatment of H358 cells (5 and 3 days after first and second siRNA transfections). SuperArray's (SuperArray Bioscience Corp. Frederick, Md. 21704, USA) Total RNA Isolation Kit (GA-013) was used. Subsequently first strand cDNAs were made using RT PCR Array First Strand Kit (SuperArray; C-02). Quantitative-RT-PCR analyses were performed using Taqman Gene Expression Assays (Applied Biosystems, Foster City, Calif.) for PAK1, PAK2, Zeb1, and Snail.

H358 transient transfections: H358 cells were seeded at a density of 2×10$^6$ cells/dish in 10-cm dishes. After 24 hrs, the cells were co-transfected using Fugene 6 (Roche, 11814443001) with pcDNA5-TO-Snail-Flag and one of the following plasmids: pcDNA3.2, pcNDA3.2-PAK1, pcDNA3.2-PAK1-L107F, or pcDNA3.2-PAK1-AID. Transfection reagent was removed 4 hrs post transfection and replaced with growth media. After 72 hrs, cells were harvested via scraping in media, washed once in PBS, and lysed with NucBuster™ Protein Extraction Kit (Novagen, Madison, Wis.; 71183-3). Resulting nuclear and cytoplasmic fractions were used for SDS-PAGE followed by immunoblotting.

H358 wound healing assay: H358 cells were seeded and transfected twice with siRNA as described above. 7 days after initial cell plating, the cells were trypsinized and re-plated at a density of 0.4×10$^6$ cell per well in 12-well plates with or without addition of 10 nM TGFβ3. At 24 hrs, a pipet tip was used to scratch a line across the center of the well. Media was replaced with or without addition of 10 M TGFβ3. Cells were photographed with Nikon® phase contrast microscope 24 hrs after scratching.

Results

We set out to investigate the role of PAK kinases in TGFβ-mediated EMT in H358 NSCLC cells. FIG. 1 shows that H358 cells respond to TGFβ3 by downregulating the expression of epithelial markers (E-cadherin and ErbB3) and upregulating that of mesenchymal markers (vimentin, N-cadherin, and fibronectin). These changes correlate with an increase in the protein levels of the EMT driver ZEB1 (FIG. 1).

Figure 2:
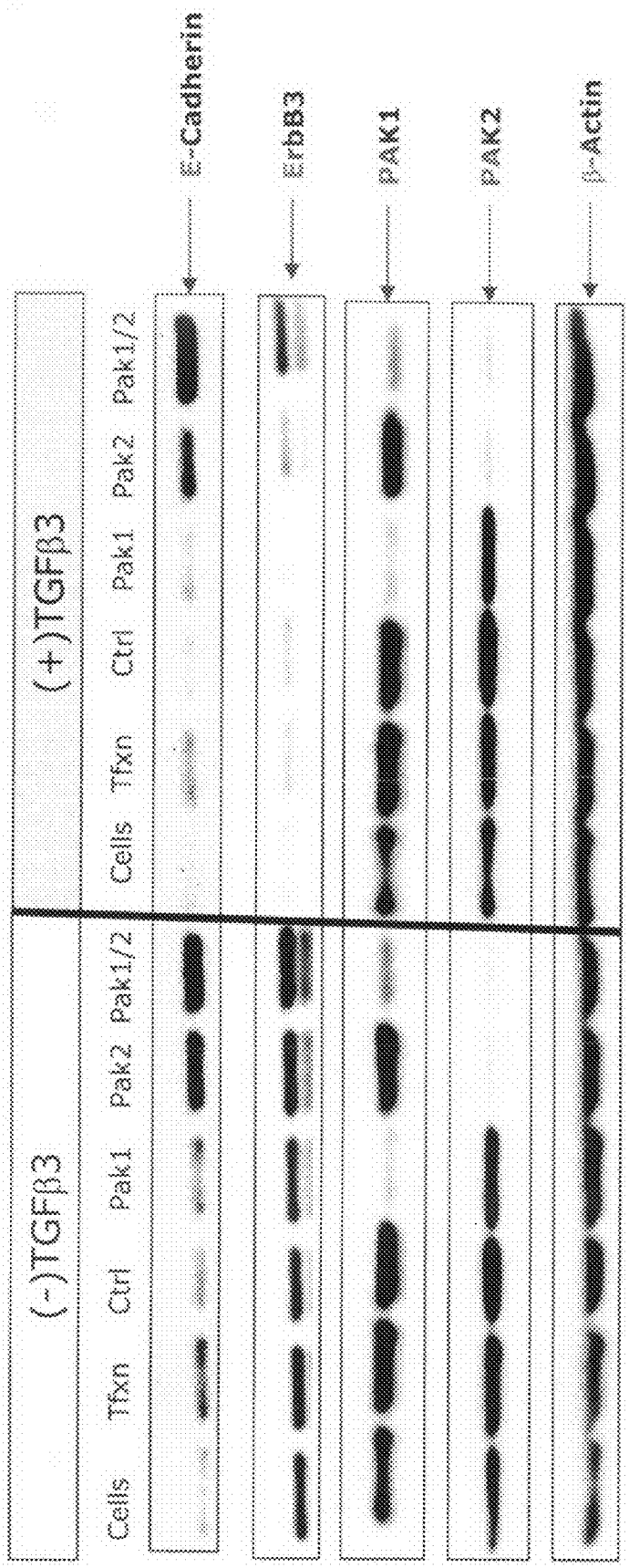
FIG. 2: PAK2 siRNA knockdown blocks TGFβ3-mediated downregulation of epithelial markers; PAK1 knockdown augments the PAK2 effect. PAK1, PAK2, and control (Ctrl) siRNAs were transfected into H358 cells with lipofectamine transfection reagent on days 1 and 3 after cell plating. TGFβ3 was then added to cells on day 3 and incubation continued for additional 72 hours before cell lysis. Protein extracts were analyzed by Western blot using the indicated antibodies. First two lanes in each panel represent untreated cells (Cells) and cells treated with lipofectamine only (Tfxn) respectively.

Since PAK1 has been reported to modulate the function of Snail via Ser-246 phosphorylation [Yang, Z., et al., Cancer Res, 2005. 65(8): p. 3179-84] and Snail is a known driver of ZEB1 expression [Guaita, S., et al., J Biol Chem, 2002. 277 (42): p. 39209-16], we asked whether knockdown of PAK1 or its close homolog PAK2 would impact the EMT changes in the TGFβ-treated H358 cells. FIG. 2 clearly shows that efficient knockdown of PAK2 but not PAK1 blocks TGFβ3-mediated reduction in protein levels of the epithelial markers E-cadherin and ErbB3. Though PAK1 knockdown on its own was not enough to prevent epithelial marker downregulation, it did augment the effect observed with PAK2 knockdown (FIG. 2); both E-cadherin and ErbB3 protein levels are higher in the double knockdown than in the siPAK2 sample.

Figure 3:
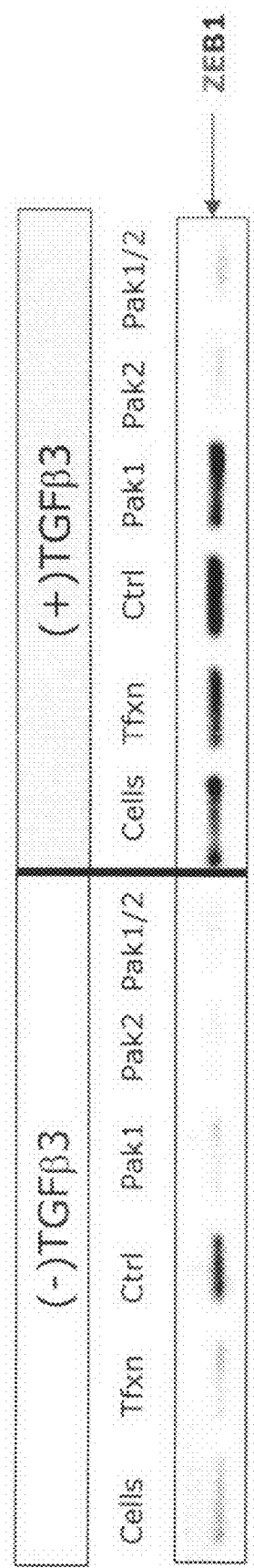
FIG. 3: PAK2 knockdown prevents ZEB1 protein accumulation downstream of TGFβ3. Protein extracts from cells treated as in FIG. 2 were analyzed for ZEB1 protein by western blotting.
Figure 4:
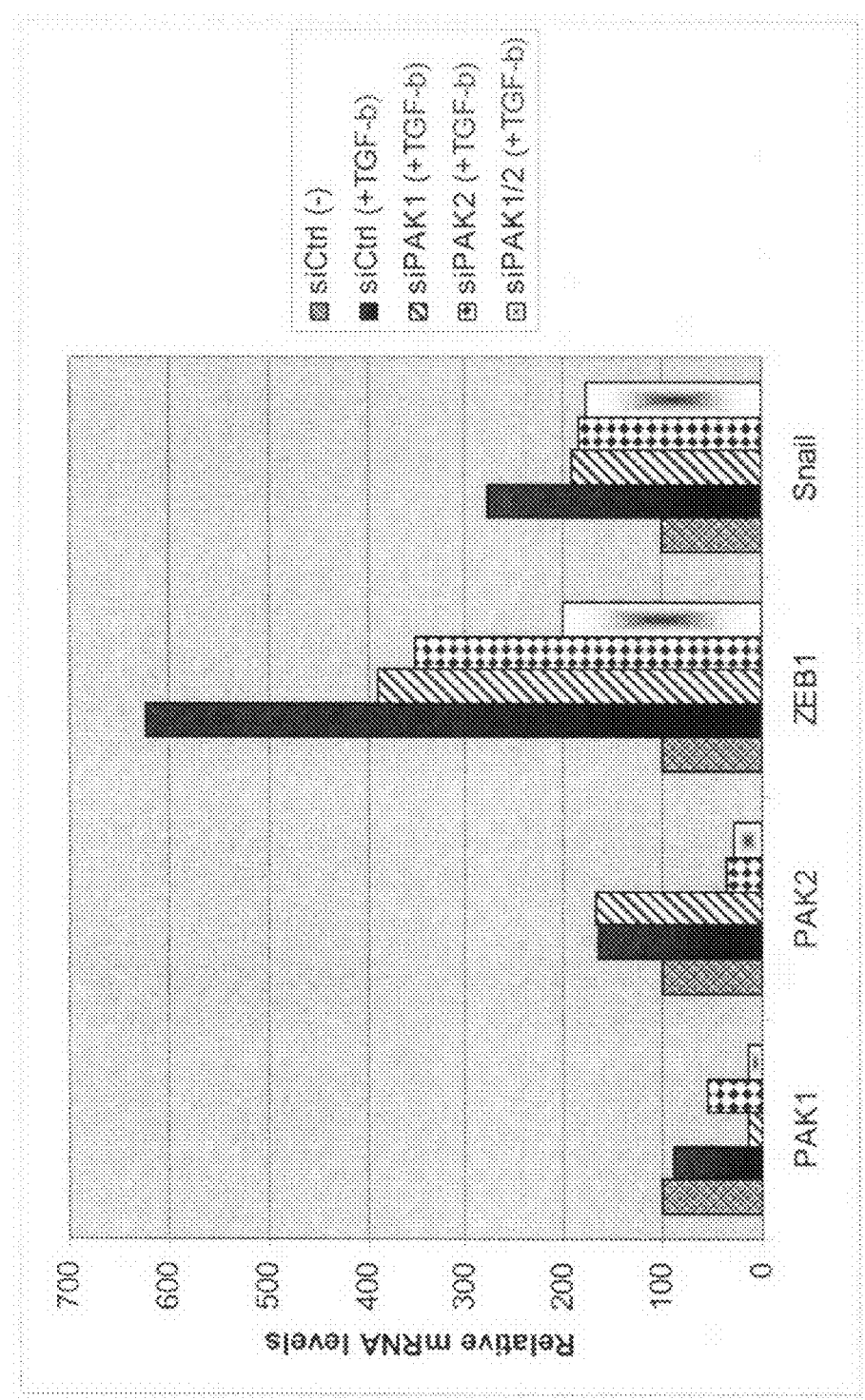
FIG. 4: Block of epithelial gene downregulation by PAK2 siRNA results in part from the inhibition of TGFβ3-mediated transcriptional upregulation of Snail and ZEB1. siRNA transfections and TGFβ3 treatment were conducted as in FIG. 2. Total RNA isolation was done at 72 hours post-TGFβ3 treatment. RNA was reverse transcribed into first strand cDNA then analyzed by quantitative PCR with the appropriate TaqMan probes. mRNA levels for each of the analyzed genes were normalized to that in the siCtrl sample, which was set at 100%.

When ZEB1 protein levels were examined in the same samples, it became evident that the dominant role of PAK2 on epithelial marker regulation correlates with its ability to maintain ZEB1 protein level (FIG. 3). PAK2 knockdown reduced basal ZEB1 protein level in untreated H358 cells. Moreover, PAK2 but not PAK1 knockdown resulted in almost complete attenuation of the increase in ZEB1 elicited by TGFβ3 (FIG. 3). However, when RNA levels of ZEB1 are examined PAK1 and PAK2 seemed to have a similar effect on ZEB1 mRNA induction by TGFβ3; both reduced induction from 6 to 3-4 fold (FIG. 4). This would indicate that PAK2 exerts an additional post-transcriptional effect on ZEB1, either at the levels of translation or stability. PAK1 and PAK2 also reduce the mRNA induction of Snail to similar extents (from ~2.8-fold to ~1.8-fold). Treatment with both siRNAs simultaneously has no additional effect on Snail mRNA but seems to additively reduce the ZEB1 induction level (to ~2-fold) (FIG. 4).

Figure 5:
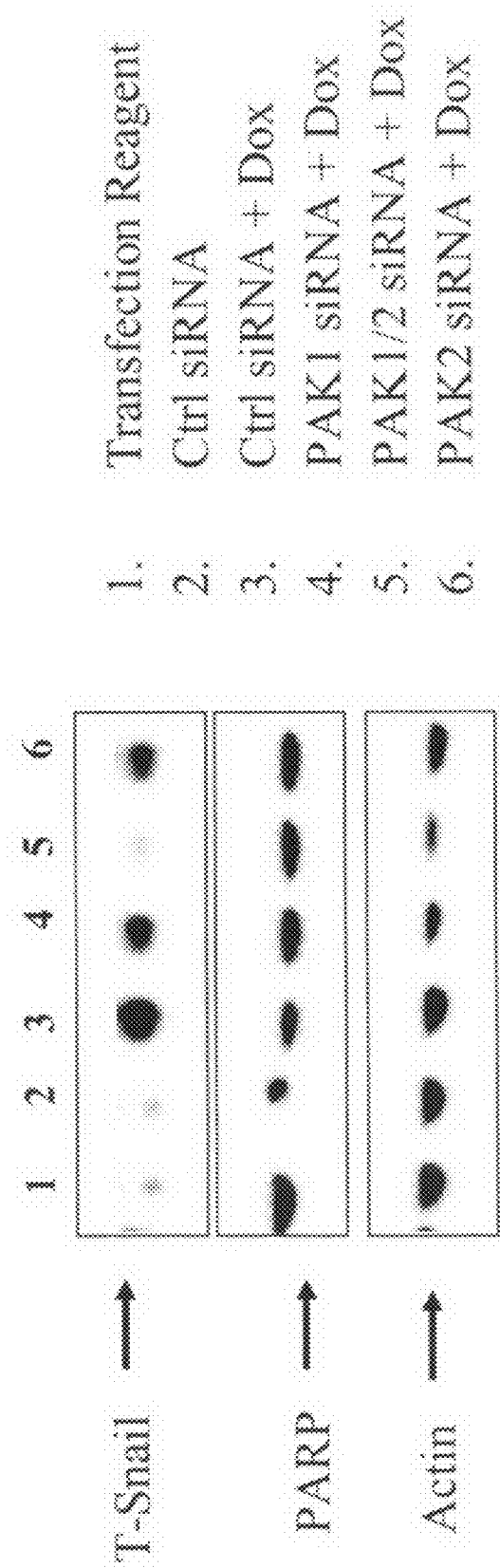
FIG. 5: PAK1/2 knockdown reduces Snail protein levels in the nucleus. HCT116/tet-on/Snail-Flag cells were transfected with siRNAs against PAK1, PAK2, PAK1/2, or with a control siRNA. Forty eight hours after transfection, Snail expression was induced with doxycycline. Snail protein levels in the nuclear compartment were analyzed by western blotting 24 hours post induction.
Figure 6:
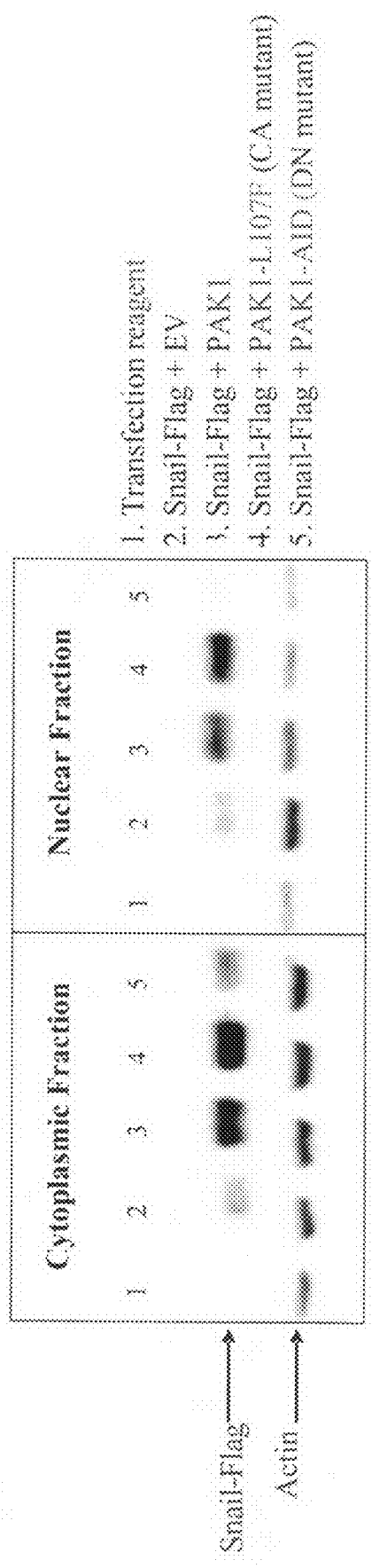
FIG. 6: PAK1 overexpression increases Snail protein levels in the cytoplasmic and nuclear compartments. H358 cells were transfected with a Snail-Flag expression plasmid along with pcDNA3.2 plasmids containing no insert (lane 2), wild-type PAK1 (lane 3), a constitutively active mutant of PAK1 (PAK1-L107F; lane 4), or the dominant negative autoinhibitory domain (PAK1-AID; lane 5).

The fact that PAK1 was able to augment the effects of PAK2 on EMT marker changes despite the fact that it did not seem to enhance PAK2's effect on Snail mRNA accumulation led us to investigate the effect of PAK1 on Snail protein levels. Knockdown of either PAK1 or PAK2 in Snail-expressing HCT116/tet-on/Snail-Flag cells caused slight reductions in Snail protein levels in the nucleus (FIG. 5; lanes 4 and 6) while the double knockdown sample showed a much more pronounced reduction (FIG. 5; lane 5). Conversely overexpression of either wildtype or constitutively active PAK1 in H358 cells, co-transfected with a Snail expression plasmid, led to an enhanced accumulation of the Snail protein (FIG. 6; lanes 3 and 4). A PAK1 fragment (PAK1-AID) expressing amino acids 83-149 of human PAK1 and lacking the kinase domain did not seem to have an enhancing effect (FIG. 6; lane 5), hence implicating PAK's kinase domain in the enhancement of Snail protein accumulation.

Figure 7:
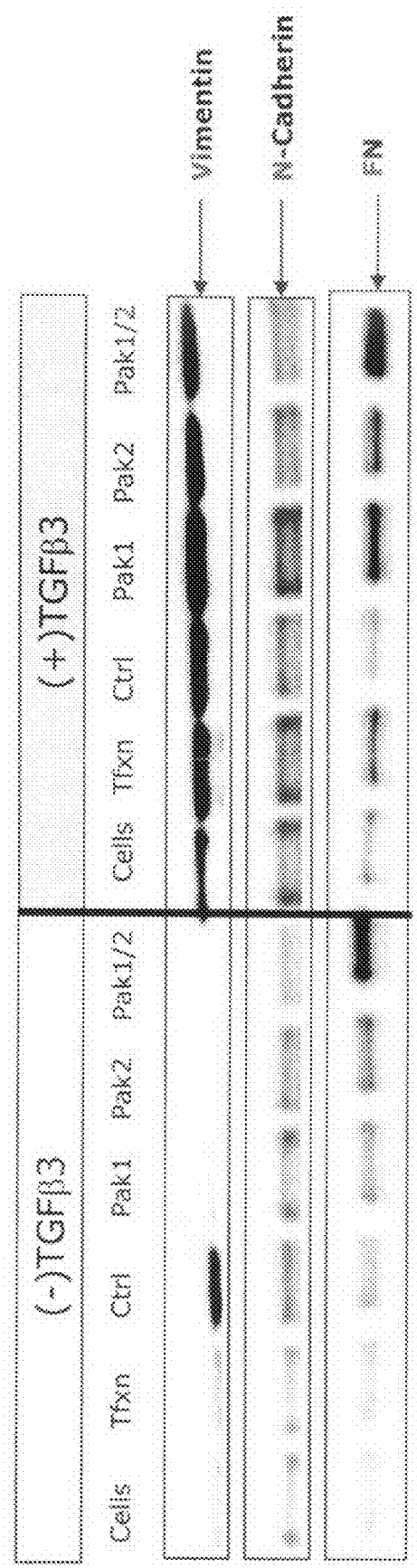
FIG. 7: PAK1 and PAK2 knockdown have minimal to no effect on mesenchymal marker expression. Protein extracts from same samples as in FIG. 2 were analyzed by western blotting for expression of mesenchymal vimentin, N-cadherin, and fibronectin.
Figure 8:
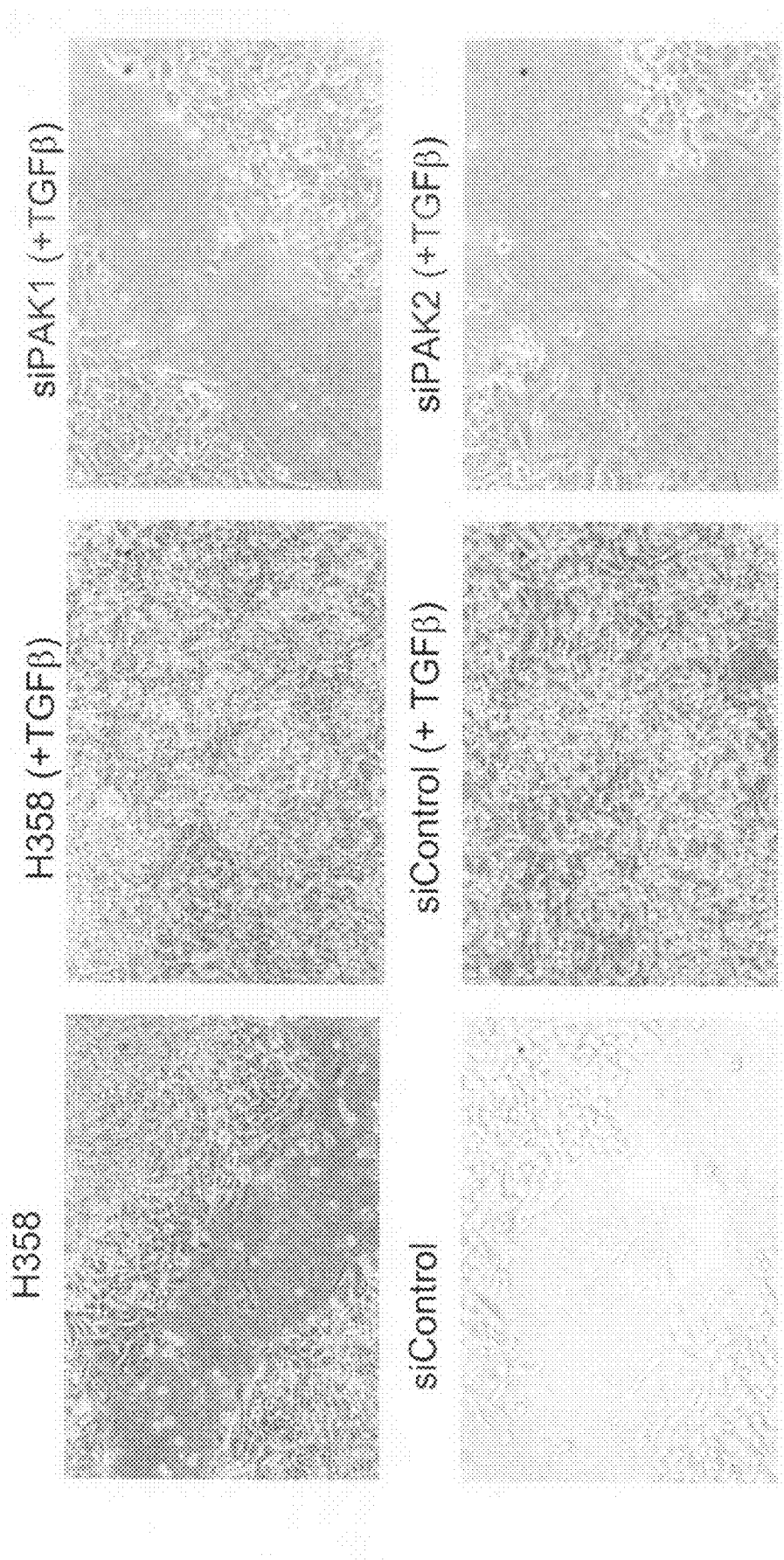
FIG. 8: Knockdown of either PAK1 or PAK2 impairs TGFβ3-induced H358 cell migration. H358 cells transfected with different siRNAs were plated at a confluent density, treated with TGFβ3 then scratched with a pipet tip. Cell migration was monitored 24 hours later.

Though PAK kinase inhibition by siRNA knockdown impacted the downregulation of epithelial markers by TGFβ3, it did not have an effect on mesenchymal marker expression such as vimentin- and N-cadherin (FIG. 7) while slightly upregulating that of fibronectin (FIG. 7). It is not evident apriori whether the phenotype of the resulting H358 cancer cells coexpressing epithelial and mesenchymal markers would be more similar to epithelial-like parental H358 or mesenchymal-like TGFβ3-converted cells. We therefore conducted a scratch migration assay on cells treated with TGFβ3 and transfected with either control siRNA or siRNAs targeting PAK1, PAK2, or both. We found that knockdown of either PAK1 or PAK2 impairs the ability of cells to migrate into the scratch in reponse to TGFβ signaling (FIG. 8). The effect on cell migration likely reflect the fact that PAK kinases phosphorylate and regulate the function of vimentin [Li, Q. F., et al., J Biol Chem, 2006. 281(45): p. 34716-24] and of many proteins with roles in actin cytoskeletal remodeling and cell motility [Kumar, R., et al., p21-activated kinases in cancer. Nat Rev Cancer, 2006. 6(6): p. 459-71].

Significance of the Data:

The importance of PAK1/2 in the EMT process via modulation of Snail and ZEB1 makes these two kinase attractive targets for small molecule inhibitors that would impede EMT downstream of many pathophysiological stimuli. As mentioned in the background, Snail has been demonstrated to function downstream of many such stimuli that induce EMT (TGFb, HGF, Wnt, and Shh). Moreover ZEB1, which can induce EMT downstream of Snail or independently, is similarly up regulated by many extracellular stimuli such as TGFβ [Shirakihara, T., et al. Mol Biol Cell, 2007. 18(9): p. 3533-44], TNFβ [Chua, H. L., et al., Oncogene, 2007. 26(5): p. 711-24], PGE2 [Dohadwala, M., et al., Cancer Res, 2006.66 (10): p. 5338-45], and thymosin β4 [Huang, H. C., et al., Oncogene, 2007. 26(19): p. 2781-90].

PAK1 was previously implicated in Snail phosphorylation [Yang, Z., et al. Cancer Res, 2005. 65(8): p. 3179-84]—this phosphorylation was shown to be important for localization of Snail to nuclear compartment in MCF7 cells. What we show here is that PAK1 activity is important for accumulation of the Snail protein. PAK2 on the other hand had never been implicated in the regulation of EMT. Our results highlight an important role for PAK2 in tonic downregulation of E-cadherin expression and in TGFβ3-mediated downregulation of E-cadherin and other epithelial markers. We also show that PAK2 activity is critical for the increase in ZEB1 protein level elicited by TGFβ3; this effect is partly due to an effect on transcript level but also likely involves a post-transcriptional function.

We therefore propose that a PAK2 inhibitor but preferably a PAK1/2 dual inhibitor will impede EMT progression downstream of TGFβ ligands and other EMT stimuli through the Snail-ZEB1 axis. It is also expected that such inhibitors will upregulate the expression of E-cadherin in epithelial-like cancer cells. Such upregulation would be expected to enhance cell adhesion through increased expression of E-cadherin and translocation of β-catenin from the nucleus to the cell membrane, and hence inhibit the tumorigenicity of epithelial-like cancer cells [Kapitanovic, S., et al., Exp Mol Pathol, 2006. 80(1): p. 91-6].

Abbreviations

EGF, epidermal growth factor; EGFR, epidermal growth factor receptor; EMT, epithelial-to-mesenchymal transition; MET, mesenchymal-to-epithelial transition; NSCL, non-small cell lung; NSCLC, non-small cell lung cancer; HNSCC, head and neck squamous cell carcinoma; CRC, colorectal cancer; MBC, metastatic breast cancer; Brk, Breast tumor kinase (also known as protein tyrosine kinase 6 (PTK6)); FCS, fetal calf serum; LC, liquid chromatography; MS, mass spectrometry; IGF-1, insulin-like growth factor-1; TGFα, transforming growth factor alpha; HB-EGF, heparin-binding epidermal growth factor; LPA, lysophosphatidic acid; $IC_{50}$, half maximal inhibitory concentration; pY, phosphotyrosine; wt, wild-type; PI3K, phosphatidyl inositol-3 kinase; GAPDH, glyceraldehyde 3-phosphate dehydrogenase; MAPK, mitogen-activated protein kinase; PDK-1,3-Phosphoinositide-Dependent Protein Kinase 1; Akt, also known as protein kinase B, is the cellular homologue of the viral oncogene v-Akt; mTOR, mammalian target of rapamycin; 4EBP1, eukaryotic translation initiation factor-4E (mRNA cap-binding protein) Binding Protein-1, also known as PHAS-I; p70S6K, 70 kDa ribosomal protein-S6 kinase; eIF4E, eukaryotic translation initiation factor-4E (mRNA cap-binding protein); Raf, protein kinase product of Raf oncogene; MEK, ERK kinase, also known as mitogen-activated protein kinase kinase; ERK, Extracellular signal-regulated protein kinase, also known as mitogen-activated protein kinase; PTEN, "Phosphatase and Tensin homologue deleted on chromosome 10", a phosphatidylinositol phosphate phosphatase; pPROTEIN, phospho-PROTEIN, "PROTEIN" can be any protein that can be phosphorylated, e.g. EGFR, ERK, S6 etc; PBS, Phosphate-buffered saline; TGI, tumor growth inhibition; WFI, Water for Injection; SDS, sodium dodecyl sulfate; ErbB2, "v-erb-b2 erythroblastic leukemia viral oncogene homolog 2", also known as HER-2; ErbB3, "v-erb-b2 erythroblastic leukemia viral oncogene homolog 3", also known as HER-3; ErbB4, "v-erb-b2 erythroblastic leukemia viral oncogene homolog 4", also known as HER-4; FGFR, Fibroblast Growth Factor Receptor; DMSO, dimethyl sulfoxide; HGF, hepatocyte growth factor; Wnt, wingless-type MMTV integration site family, member 1; IL-1, interleukin 1; HB-EGF, heparin-binding EGF-like growth factor; MSP, macrophage-stimulating protein; Wnt5a, wingless-type MMTV integration site family, member 5a; Shh, sonic hedgehog; TNF-alpha, transforming growth factor-α.

Incorporation by Reference

All patents, published patent applications and other references disclosed herein are hereby expressly incorporated herein by reference.

In addition, the sequence listing submitted to the USPTO on Jul. 24, 2009, in the ASCII text file "OS-10085$_{13}$ ST25.txt", created Jul. 23, 2009, size 10KB, consisting of four sequences, is hereby incorporated by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of identifying an agent that inhibits tumor cells from undergoing an epithelial to mesenchymal transition, comprising providing a preparation containing a p21-activated kinase 2 (PAK2kinase), incubating the preparation with a test agent to be screened under conditions to permit binding of the test agent to the kinase;

determining whether the test agent inhibits the PAK2 kinase by detecting a decrease in the phosphotransferase activity of the kinase, thus identifying agents that are PAK2 kinase inhibitors, determining whether an agent thus identified as a PAK2 kinase inhibitor, inhibits tumor cells from undergoing an epithelial to mesenchymal transition (EMT), by contacting a sample of tumor cells with said PAK2 kinase inhibitor, contacting the tumor cells with a factor known to induce an EMT in the tumor cells, determining whether the tumor cells have undergone an EMT by determining whether there is an increase in an epithelial biomarker and/or a decrease in a mesenchymal biomarker selected from the group consisting of Snail, Zeb1, Twist, Sip1, and Slug in the tumor cells relative to an identical sample of tumor cells contacted with the EMT inducing factor but not contacted with said PAK2 kinase inhibitor, and thus identifying whether said PAK2 kinase inhibitor is an agent that inhibits tumor cells from undergoing an epithelial to mesenchymal transition.

2. The method of claim 1, comprising after the step of determining whether the test agent inhibits PAK2 kinase, and prior the step of determining whether an agent identified as a PAK2 kinase inhibitor also inhibits tumor cells from undergoing an EMT, the additional steps of:

providing a preparation containing a PAK1 kinase, incubating the preparation with an agent identified as inhibiting PAK2 kinase, under conditions to permit binding of the test agent to the PAK1 kinase;

determining whether the agent identified as inhibiting PAK2 kinase also inhibits the PAK1 kinase by detecting a decrease in the phosphotransferase activity of the PAK1 kinase, thus identifying said agents as inhibitors of both PAK1 and PAK2 kinases.

3. The method of claim 1, wherein the tumor cells for which an agent is sought to inhibit an epithelial to mesenchymal transition are selected from NSCLC, head and neck, colorectal, pancreatic, breast and ovarian tumor cells.

4. The method of claim 1, wherein the preparation containing a PAK2 kinase is a purified enzyme preparation, an isolated immune complex containing the PAK2 kinase, or a cell expressing the PAK2 kinase.

5. The method of claim 1, wherein the PAK2 kinase is a polypeptide encoded by a nucleic acid that hybridizes under stringent conditions to the complement of the nucleic acid encoding a polypeptide having an amino acid sequence of SEQ ID NO:1, wherein the stringent conditions comprise incubating at 42° C. in a solution comprising 50% formamide, 5x SSC, and 1% SDS and washing at 65° C. in a solution comprising 0.2×SSC and 0.1% SDS.

6. The method of claim 5, wherein the PAK2 polypeptide comprises a polypeptide having the amino acid sequence of SEQ ID NO:1.

7. The method of claim 1, wherein the test agent is a small organic molecule.

8. The method of claim 1, wherein the epithelial to mesenchymal transition in the tumor cell samples is induced by TGF-beta, HGF, Hedgehog, Wnt, IL-1, EGF, amphiregulin, HB-EGF, MSP, Wnt5a, or TNF-alpha.

9. The method of claim 1, wherein the epithelial biomarker is selected from the group consisting of E-cadherin, cytokeratin 8, cytokeratin 18, P-cadherin, erbB3, Brk, γ-catenin, α1-catenin, α2-catenin, α3-catenin, connexin 31, plakophilin 3, stratifin 1, laminin alpha-5, and ST14.

10. A method of preparing a composition comprising a chemical compound that inhibits tumor cells from undergoing an epithelial to mesenchymal transition, comprising providing a preparation containing a PAK2 kinase, incubating the preparation with a test agent to be screened under conditions to permit binding of the test agent to the kinase;

determining whether the test agent inhibits the PAK2 kinase by detecting a decrease in the phosphotransferase activity of the kinase, thus identifying agents that are PAK2 kinase inhibitors, determining whether an agent thus identified as a PAK2 kinase inhibitor, inhibits tumor cells from undergoing an epithelial to mesenchymal transition (EMT), by contacting a sample of tumor cells with said PAK2 kinase inhibitor, contacting the tumor cells with a factor known to induce an EMT in the tumor cells, determining whether the tumor cells have undergone an EMT by determining whether there is an increase in an epithelial biomarker and/or a decrease in a mesenchymal biomarker selected from the group consisting of Snail, Zeb1, Twist, Sip1, and Slug in the tumor cells relative to an identical sample of tumor cells contacted with the EMT inducing factor but not contacted with said PAK2 kinase inhibitor, and thus identifying whether said PAK2 kinase inhibitor is an agent that inhibits tumor cells from undergoing an epithelial to mesenchymal transition, and admixing a PAK2 kinase inhibitor so identified with a carrier, thereby preparing said composition.

11. The method of claim 10, wherein the epithelial biomarker is selected from the group consisting of E-cadherin, cytokeratin 8, cytokeratin 18, P-cadherin, erbB3, Brk, γ-catenin, α1-catenin, α2-catenin, α3-catenin, connexin 31, plakophilin 3, stratifin 1, laminin alpha-5, and ST14.

12. A method of identifying an agent that impairs tumor cell mobility, and thus inhibits tumorigenicity, comprising providing a preparation containing a PAK2 kinase, incubating the preparation with a test agent to be screened under conditions to permit binding of the test agent to the kinase;

determining whether the test agent inhibits the PAK2 kinase by detecting a decrease in the phosphotransferase activity of the kinase, thus identifying agents that are PAK2 kinase inhibitors, determining whether an agent thus identified as a PAK2 kinase inhibitor, inhibits tumor cell migration, by contacting a sample of tumor cells with said PAK2 kinase inhibitor, comparing the extent of migration in said sample of tumor cells induced to migrate by addition of a migration-inducing factor, to the extent of migration in an identical sample of tumor cells induced to migrate but not contacted with said PAK2 kinase inhibitor, and thus identifying whether said PAK2 kinase inhibitor, is an agent that impairs tumor cell mobility.

13. The method of claim 12, wherein the migration-inducing factor is selected from the group consisting of TGF-beta, HGF, MSP, EGF, amphiregulin, HB-EGF, a canonical Wnt ligand, a non-canonical Wnt ligand, Wnt5a, IL-lalpha, IL-1beta, TNF-alpha, oncostatin M, and a hedgehog-family ligand.

* * * * *